(12) United States Patent
Sahadevan

(10) Patent No.: US 8,915,833 B1
(45) Date of Patent: Dec. 23, 2014

(54) IMAGE GUIDED INTRAOPERATIVE SIMULTANEOUS SEVERAL PORTS MICROBEAM RADIATION THERAPY WITH MICROFOCUS X-RAY TUBES

(76) Inventor: Velayudhan Sahadevan, Beckley, WV (US)

( * ) Notice: Subject to any disclaimer, the term of this patent is extended or adjusted under 35 U.S.C. 154(b) by 336 days.

(21) Appl. No.: 12/929,770

(22) Filed: Feb. 15, 2011

(51) Int. Cl.
*A61B 17/52* (2006.01)
*A61N 5/00* (2006.01)

(52) U.S. Cl.
USPC ........................................ 600/1; 600/2; 600/9

(58) Field of Classification Search
USPC ................ 600/9–15; 250/341.7, 492.3, 494.1
See application file for complete search history.

(56) References Cited

U.S. PATENT DOCUMENTS

| | | | |
|---|---|---|---|
| 3,714,486 A | 1/1973 | McCrary | |
| 5,090,043 A | 2/1992 | Parker et al. | |
| 5,153,900 A | 10/1992 | Nomikos | |
| 5,165,093 A | 11/1992 | Miller et al. | |
| 5,339,347 A * | 8/1994 | Slatkin et al. | 378/65 |
| 5,428,658 A | 6/1995 | Oettinger | |
| 5,566,221 A | 10/1996 | Smith | |
| 5,729,583 A | 3/1998 | Tang et al. | |
| 5,748,699 A | 5/1998 | Smith | |
| 5,854,822 A | 12/1998 | Chornenky et al. | |
| 6,108,402 A | 8/2000 | Chornenky | |
| 6,134,300 A | 10/2000 | Trebes et al. | |
| 6,289,079 B1 | 9/2001 | Chornenky et al. | |
| 6,319,188 B1 | 11/2001 | Lovoi | |
| 6,324,257 B1 | 11/2001 | Halavee | |
| 6,364,526 B2 * | 4/2002 | Ivan et al. | 378/198 |
| 6,415,016 B1 | 7/2002 | Chornenky et al. | |
| 6,438,206 B1 | 8/2002 | Shinar et al. | |
| 6,477,233 B1 | 11/2002 | Ribbing et al. | |
| 6,487,272 B1 | 11/2002 | Kutsuzawa | |
| 6,553,096 B1 | 4/2003 | Zhou et al. | |
| 6,580,940 B2 | 6/2003 | Gutman | |
| 6,623,418 B2 | 9/2003 | Smith | |
| 6,661,875 B2 | 12/2003 | Greenwald et al. | |
| 6,718,012 B2 | 4/2004 | Ein-Gal | |
| 6,721,392 B1 | 4/2004 | Dinsmore | |

(Continued)

OTHER PUBLICATIONS

E.A. Dilmanian, T.M. Button, G. Le Duc, N. Zhong, L.A. Pena, J. A.L. Smith, S.R. Martinez, T. Bacarian, J. Tammam, B. Ren, P.M. Farmer, J. Kalef-Exra, P.L. Micca, M.M. Nawrocky, J.A. Niederer, F.P. Recksiek, A. Fuchs, E.M. Rosen, "Response of rat intracranial 9L gliosarcoma to microbeam radiation therapy," Neuro-Oncology, Jan. 2002, pp. 26-38.*

(Continued)

*Primary Examiner* — Jacqueline Cheng
*Assistant Examiner* — Eileen Foley

(57) ABSTRACT

A microbeam intraoperative, 10-50 kilovoltage radiation therapy system with multiple simultaneous microfocus X-ray sources and method for image guided, microsecond duration, 100 to 1,000 Gy microbeam radiation therapies with dose rate ranging from 1,000 to 20,000 Gy per second and RBE closer to high LET with minimal toxicity to normal tissue is provided. Dismountable coronal, sagital and transverse half-circle gantry sections are assembled on to a surgical table for mounting the microfocus X-ray sources for intraoperative radiosurgery. A stereotactic breast core biopsy system is adapted for combined breast biopsy, positron emission tomography and computerized tomography with phase-contrast imaging. Cosmetic whole breast preserving electronic brachytherapy is combined with stereotactic core biopsy. The low dose valley regions of the intersecting microbeams at the tumor site are filled with scattered and characteristic radiation from high Z-element that is bound or implanted into the tumor.

9 Claims, 39 Drawing Sheets

(56) References Cited

U.S. PATENT DOCUMENTS

| | | | |
|---|---|---|---|
| 6,771,737 | B2 | 8/2004 | Kerslick et al. |
| 6,799,075 | B1 | 9/2004 | Chornenky et al. |
| 6,891,177 | B1* | 5/2005 | Kraft et al. ............ 250/505.1 |
| 6,987,835 | B2 | 1/2006 | Lovoi |
| 7,194,063 | B2 | 3/2007 | Dilmanian et al. |
| 7,643,610 | B2 | 1/2010 | Dilmanian |
| 7,746,979 | B2 | 6/2010 | Dilmanian et al. |
| 7,771,117 | B2 | 8/2010 | Kim et al. |
| 7,835,492 | B1 | 11/2010 | Sahadevan |
| 2001/0038680 | A1 | 11/2001 | Davidson |
| 2005/0033108 | A1* | 2/2005 | Sawyer ........................ 600/9 |
| 2006/0160662 | A1* | 7/2006 | Munnia ......................... 482/1 |
| 2009/0080604 | A1* | 3/2009 | Shores et al. ................ 378/37 |
| 2009/0088663 | A1* | 4/2009 | Miller et al. ................ 600/566 |
| 2009/0182312 | A1* | 7/2009 | Gertner et al. ................ 606/4 |
| 2009/0185660 | A1 | 7/2009 | Zou et al. |
| 2009/0245468 | A1 | 10/2009 | Zou et al. |
| 2009/0304157 | A1 | 12/2009 | Fuerst et al. |
| 2010/0160775 | A1* | 6/2010 | Pankratov et al. .......... 600/427 |
| 2010/0329413 | A1* | 12/2010 | Zhou et al. ................... 378/4 |

OTHER PUBLICATIONS

U.S. Appl. No. 60/790,192, filed Apr. 6, 2006, Velayudhan Sahadevan.

U.S. Appl. No. 11/784,398, filed Apr. 5, 2007, Velayudhan Sahadevan.

U.S. Appl. No. 11/974,876, filed Oct. 15, 2007, Velayudhan Sahadevan.

U.S. Appl. No. 60/872,117, filed Nov. 30, 2006, Velayudhan Sahadevan.

U.S. Appl. No. 60/927,622, filed May 3, 2007, Velayudhan Sahadevan.

U.S. Appl. No. 12/151,014, filed May 3, 2008, Velayudhan Sahadevan.

U.S. Appl. No. 12/459,120, filed Jun. 25, 2009, Velayudhan Sahadevan.

U.S. Appl. No. 12/655,825, filed Jan. 7, 2010, Velayudhan Sahadevan.

U.S. Appl. No. 12/799,949, filed May 6, 2010, Velayudhan Sahadevan.

Brenner, D.J., Leu C.S., Betty, J.F., Shefer R.E., Clinical biological effectiveness of low energy x-rays emitted by miniature x-ray devices. Phys Med boil, 44: 323-333, 1999.

Thermo Electron Corporation, KM 12506E-A MicroFocus x-ray tube 125 kV, End Widow, catalog, Thermo Electron Corporation, 320 El Pueblo Road, Scotts Valley, CA, USA 95066.

Serduc R et al,: High-Precision Radiosurgical Dose Delivery by—PLoS One, 2010; 5(2): e9028, Published online Feb. 3, 2010, doi: 10.1371/journal.pone.0009028.

Denardo S.J. et al, Tumor targeted radioisotope therapy, p. 1610, in Text book of Radiation Oncology; ed. Steven A. Liebel and Theodore L. Phillips, 2004, Saunders.

Denardo S.J. et al, Tumor targeted radioisotope therapy, p. 1619, in Text book of Radiation Oncology; ed. Steven A. Liebel and Theodore L. Phillips, 2004, Saunders.

Hass-Kogan et al, Gene-targeted therapy, p. 1597, in Text book of Radiation Oncology; ed. Steven A. Liebel and Theodore L. Phillips, 2004, Saunders.

(and 56)Chang S and Zhou O., Carbon nanotube field emission . . . slides, Internet.; Schreiberet al-.,—microirradiation,system: Radiation Research 171, 332-341, 2009.

C. C. Park et al, (ASTRO) Emerging Technology Committee Report on Electronic Brachytherapy: Int. J. Radiation Oncology Biol. Phys. 2010:76: 963- 972.

Schreiber E. C., Chang S. X., Monte Carlo simulation of an X-ray Pixel beam Microirradiation system: Radiation Research 171, pp. 332-341, 2009.

Price K. M. et al., Microbeam studies of the bystander response: J Radiat Res (Tokyo), Mar. 2009 ; 50 (Suppl A): A1-A6.

Galderisi U et al., Stem cell and bran cancer: Cell death and Differentiation, vol. 13, pp. 5-11, 2006.

Khan F. M.: Multiple Fields, in the Physics of Radiation Therapy, p. 213-216 Khan, F. M.(ed), 2003, Lippencott Williams & Wilkins, Philadelphia.

Lehnert A, Dor Wolfgang, Lessmann E. and Palwelke, J. RBE of 10 kV X rays determined for the human mammary epithelial cell line MCF-12A. Radiation research 169, 330-336.

Hall, E.J., The time at which oxygen acts an . . . , p. 92-96, Fig. 6.2 p. 93, in Radiobiology for the Radiologist, Fifth Edition, Lippencott, William and Wilkins, 2000.

Hall, E.J., The time at which oxygen acts . . . , p. 92-96, Fig. 6.4, 6.5 p. 95, in Radiobiology for the Radiologist, Fifth Edition, Lippencott, William and Wilkins, 2000.

Grabau D. A. et al., Needle biopsy of breast cancer. Appearance of tumor cells along the needle track. Eur. J. Surg Oncol 1993; 19 (2): pp. 192-194.

Youngson B. J., Epithelial displacement in surgical breast specimens following needle procedures. TM American J of Surgical Pathology 1994, 18 (9): 896-903.

(Target-A trial: an international, prospective, randomized, non-inferiority phase 3 trial, Lancet vol. 376, issue 9735, pp. 91-102, Jul. 10, 2010(66).

Kimple R. J. et al., Cosmetic—accelerated partial breast irradiation before surgical excision—: Int. J Rad Oncol Phys Apr. 13, 2010, (electronic pre-publication).

Wentz F. et al., Intraoperative radiotherapy—boost—low-kilovoltage X-rays,Int. J Radiation Oncology Biol. Phys. vol. 77, No. 5, pp. 1309-1314, 2010.

Slatkin P et al Subacute neuropathlogical effects of microplanar beams of X-rays from a synchrotron wiggler: Proc. Natl. Acad. Sci. USA, 92, pp. 8783-8787, Sep. 1995.

Roukos D. H. et al, Commentary, Breast-conserving surgery and risk of positive margins in breast cancer; Gastric Breast Cancer ntwo. center vol. 2 (1) Jan./May 2003,Table 1.

Viani G. A. et al., Breast-conserving surgery with or without radiotherapy—ductal carcinoma in situ: a meta-analysis . . . ; Radiation Oncology 2007, pp. 2-28.

Friedman et al., Recursive partitioning—high and low risk for ipsilateral tumor recurrence after breast conservingsurgery and radiation , J Clin Oncol 20: 4015-4021.

Sartor C. I., and Tepper J. E., Randomized trial of breast irradiation schedules after lumpectomy—lymph node negative breast , J Natl Cancer Inst, 2002,94 (15): 1114-1115.

Hepel J.T. et al., Toxicity—conformal radiation therapy accelerated partial breast irradiation, Int. J. Radiation Oncology Biol. Phys. 75, No. 5, p. 1290-1296, 2009.

Jagsi R. et al., Unac. cosmesis—intensity modulated radiation therapy—. accelerated partial breast irradiation Int. J. Radiation Oncology Biol. Phys. 76, pp. 71-78, 2010.

Vaidya J. et al., Targeted intraoperative radiotherapy for breast cancer (Target-A trial)—Lancet vol. 376, issue 9735, pp. 91-102, Jul. 10, 2010.

Miller R and Thomadsen B., Brachytherapy physics: everything you need to know—issues: AAPM 51st Annual Meeting, Jul. 26-30, 2009, Anaheim Convention Center, Anaheim, Califor.

Herskind C., et.al., Sphere of Equivalance-a novel target volume—intraoperative low-energy X-rays: Int. J. Radiation Oncology Biol. Phys. 72, No. 5, pp. 1575-1581,2008.

Khan F. M. : High Dose Rate Brachytherapy, in the Physics of Radiation Therapy, p. 521; Khan, F. M.(ed), 2003, Lippencott Williams & Wilkins, Philadelphia.

Hall, E.J., Repair of Radiation Damage,—Dose-Rate Effect, p. 70-73, Fig. 5.3 p. 70, in Radiobiology for the Radiologist, Fifth Edition, Lippencott, William and Wilkins, 2000.

(56) References Cited

OTHER PUBLICATIONS

Sahadevan V., Preparation of directly iodinated steroid hormones and related compounds, US patent 4,321,208, issued on Mar. 23, 1982.

Sahadevan V. and Sahadevan C., Estrogen contents of estrogen receptor positive and negative breast cancer. Unpublished data, 1982.

Xiaowei Yang et al, Synergetic activation of functional estrogen receptor (ER)-α by DNA . . . , Cancer Research 61, 7025-7029, ) Oct. 1, 2001.

Sarrazin P et al, Carbon nano tube field emission X-ray tube for space exploration: JCPDS—International Centre for Diffraction Data 2004, Adv. X-ray Analy, vol. 47, p. 232-238.

Kani T et al, Biophysical characteristics of HIMAC Clinical Irradiation System, heavy-ion radiation therapy: Int. J. Radiation Oncology Biol. Phys. 44, pp. 201-210, p. 206.

Hall E.J., Linear Energy Transfer: in Radiobiology for the Radiologist, Hall E. J. (Ed)., p. 113-114, fifth ed. Lippencott Williams & Wilkins, 2000, Philadelphia.

* cited by examiner

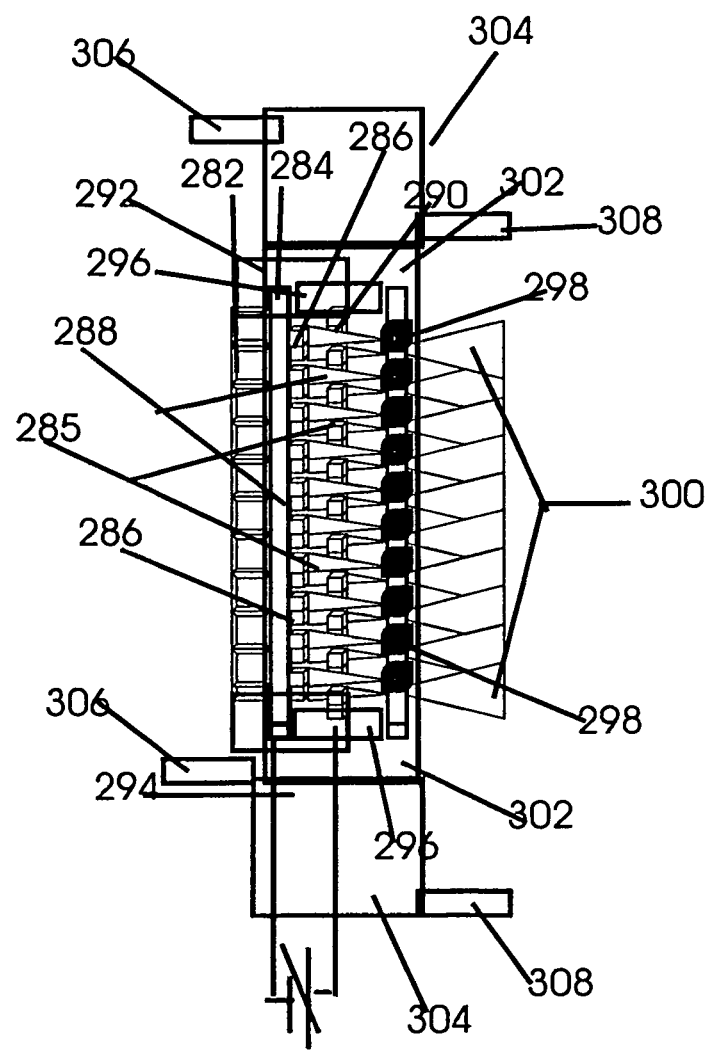

340

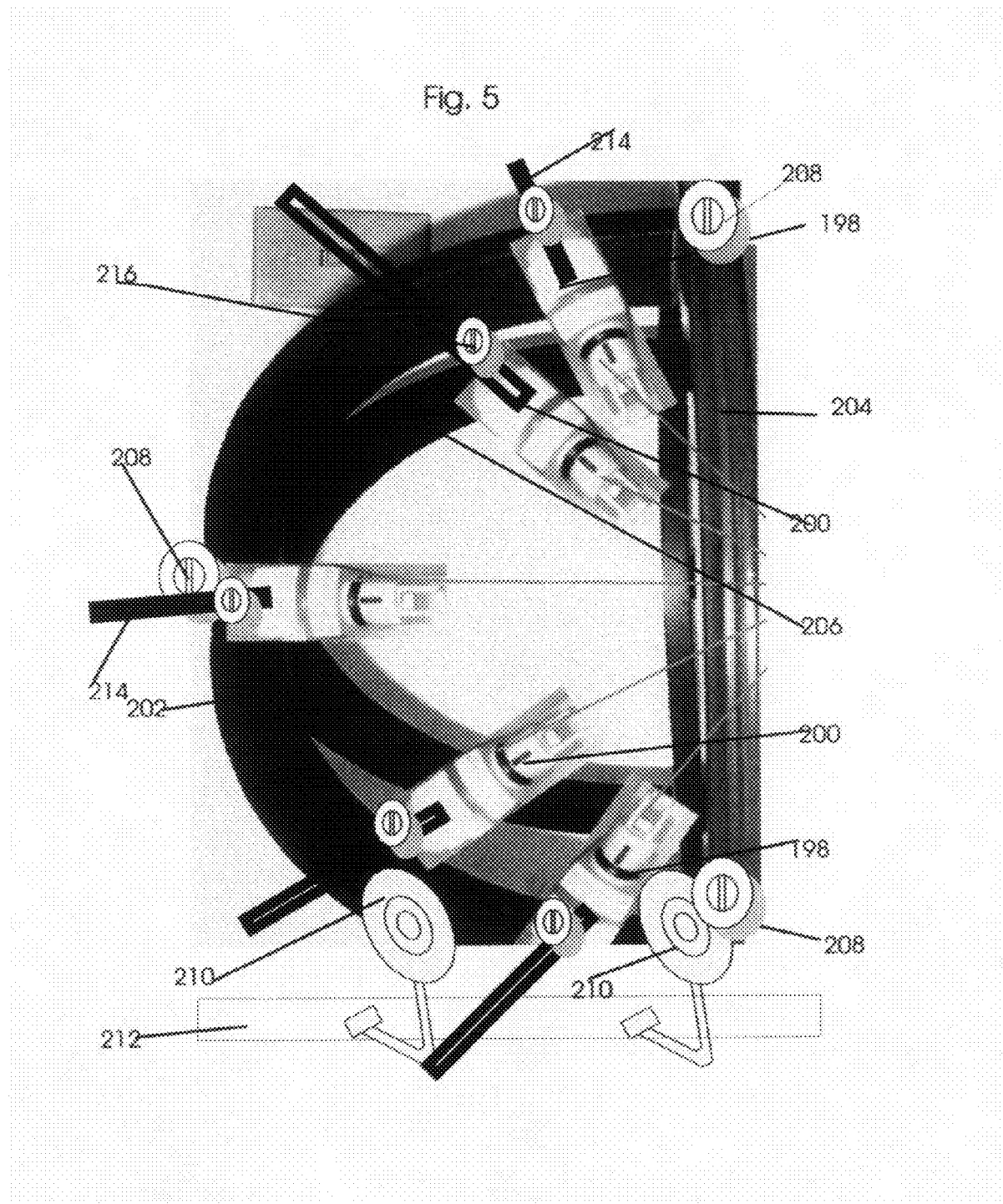

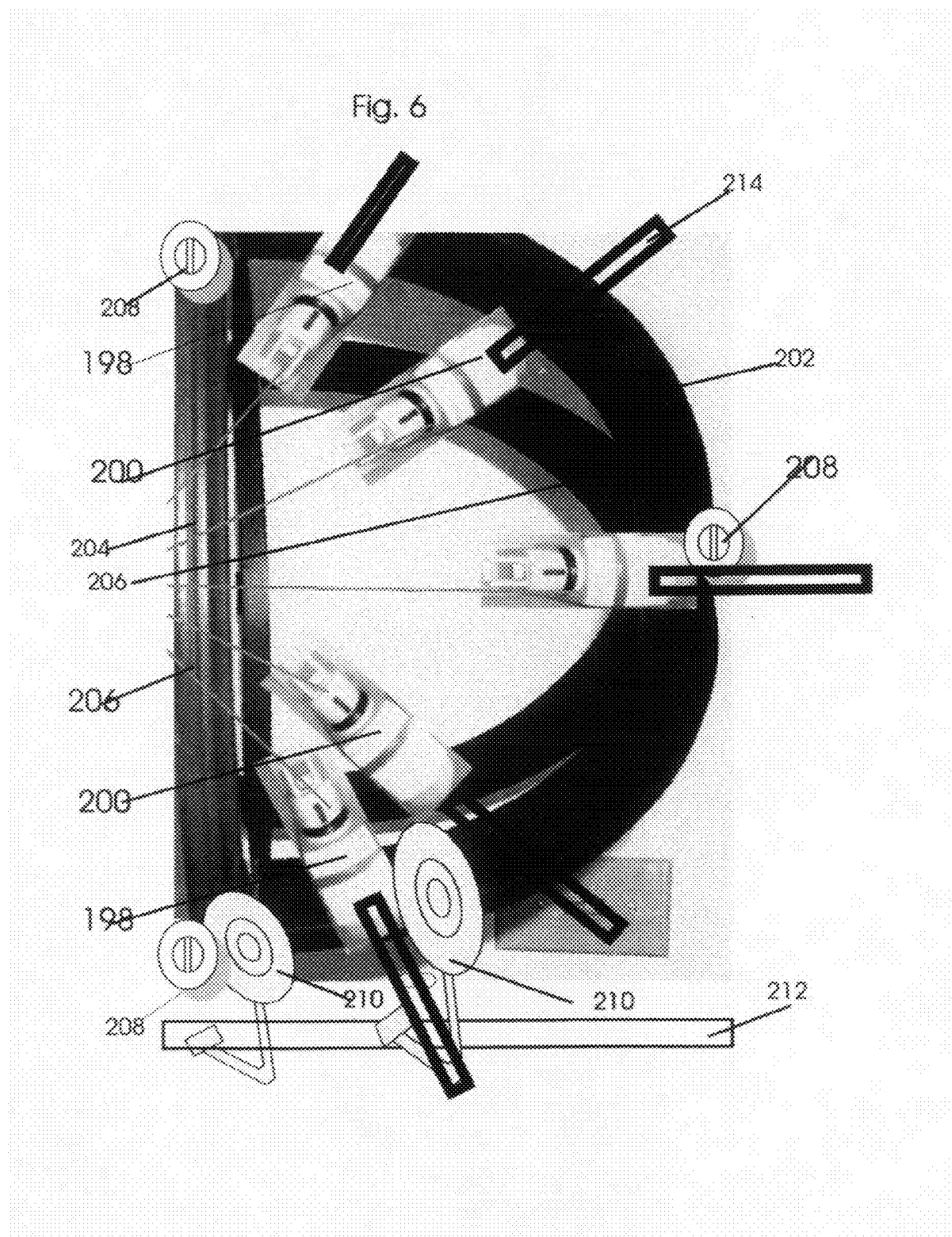

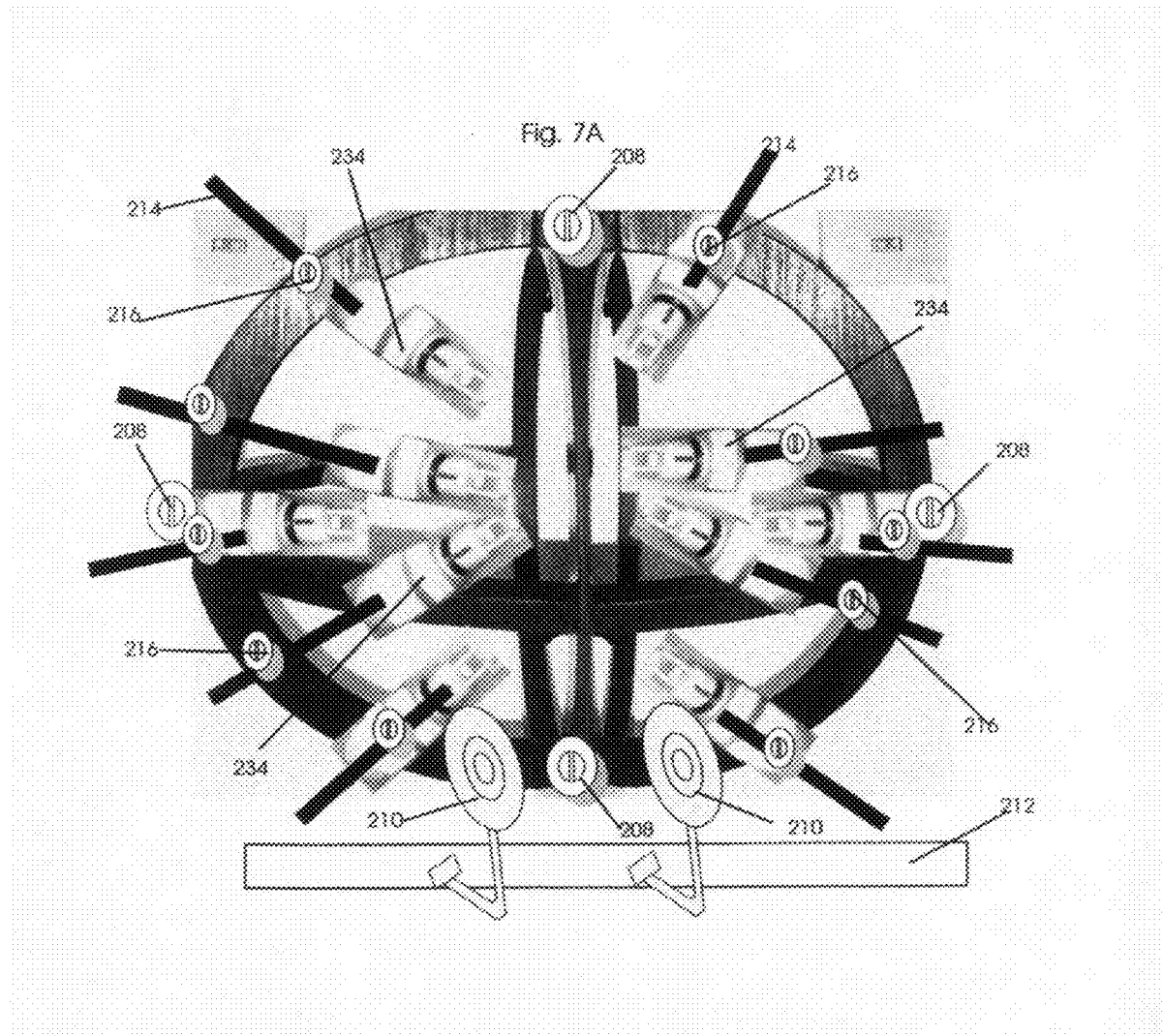

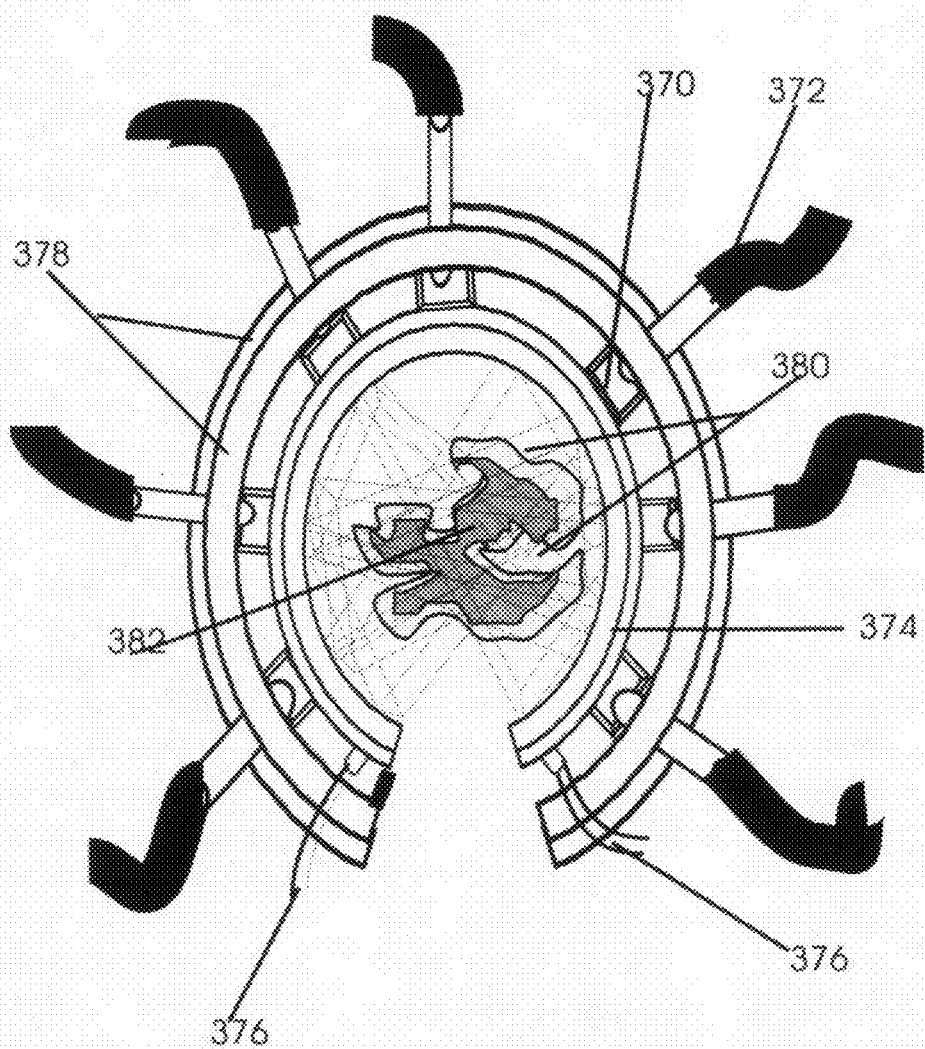

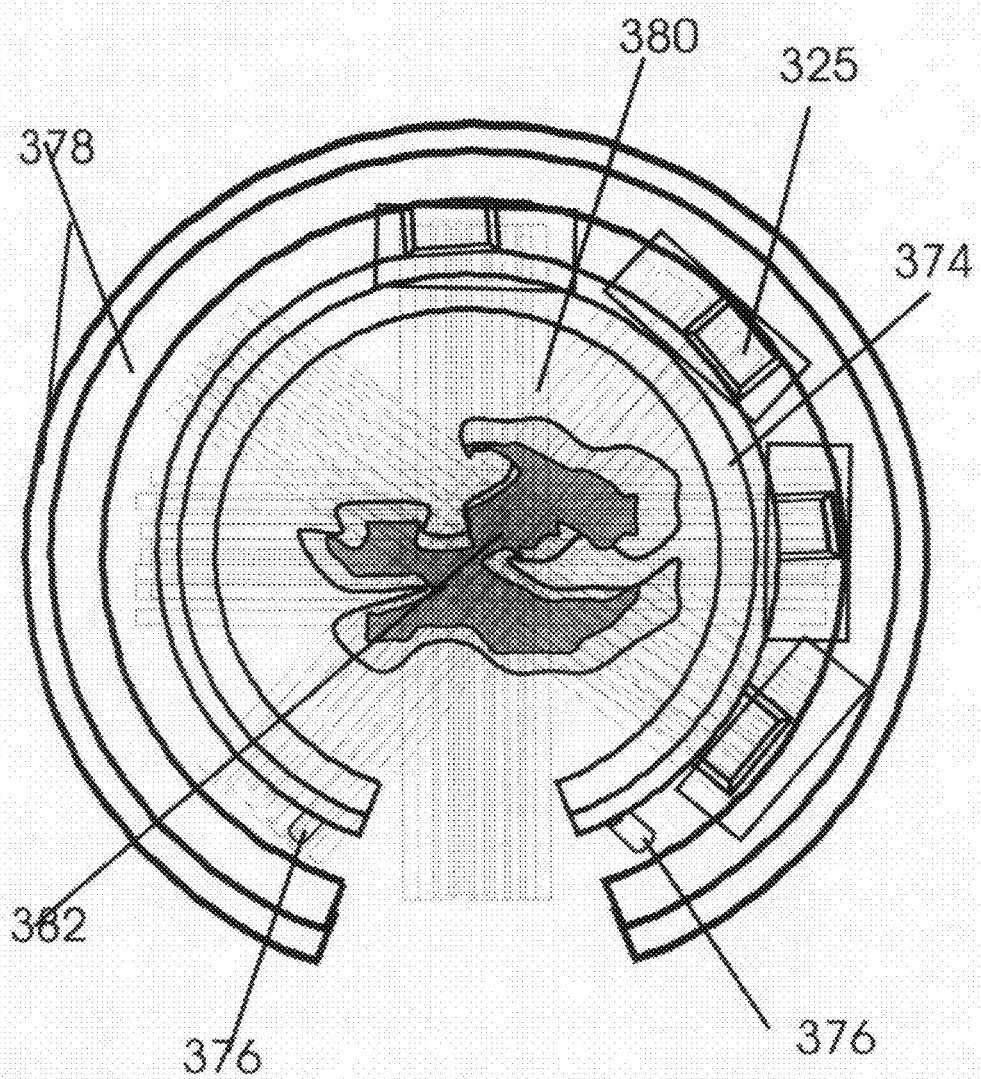

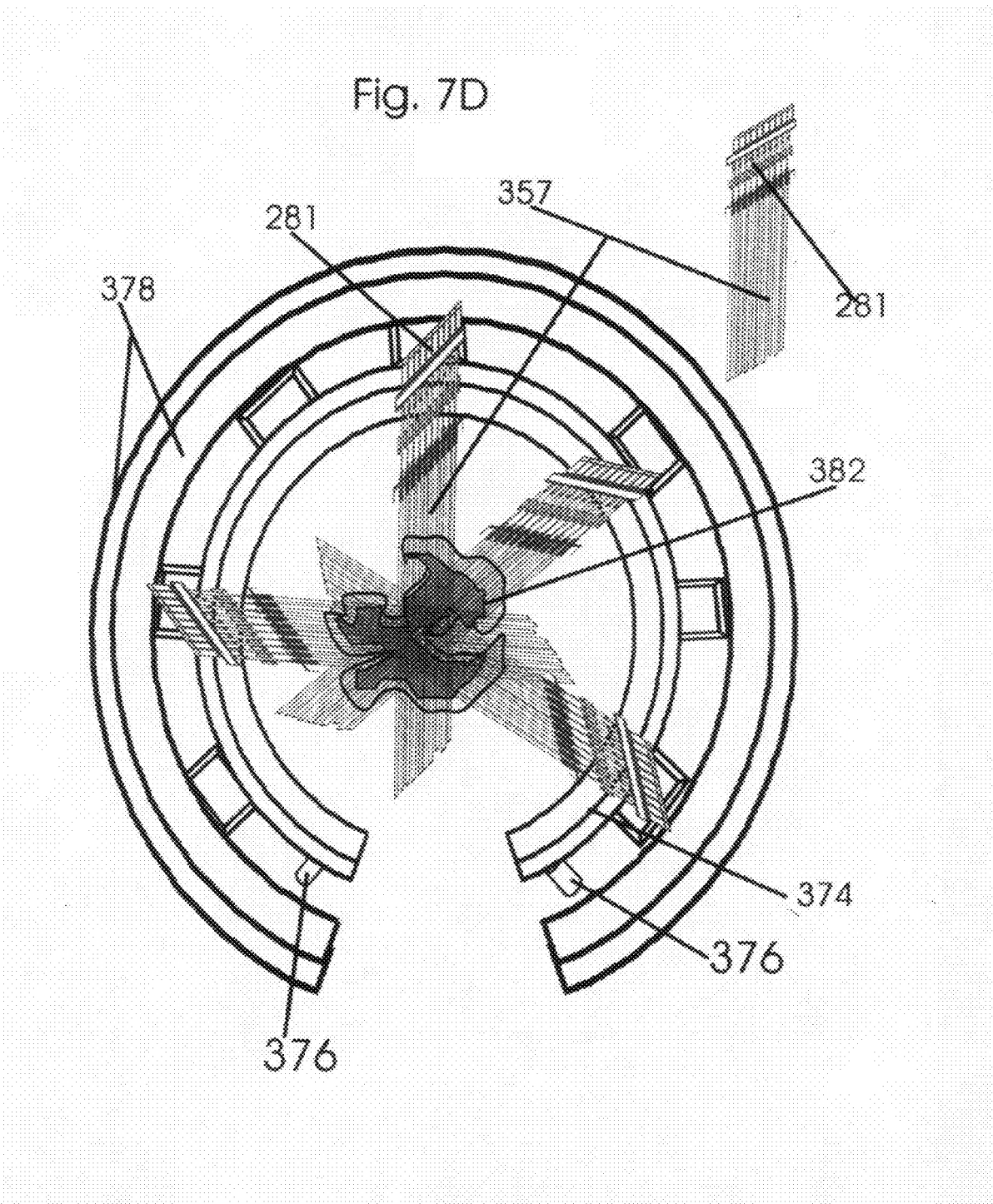

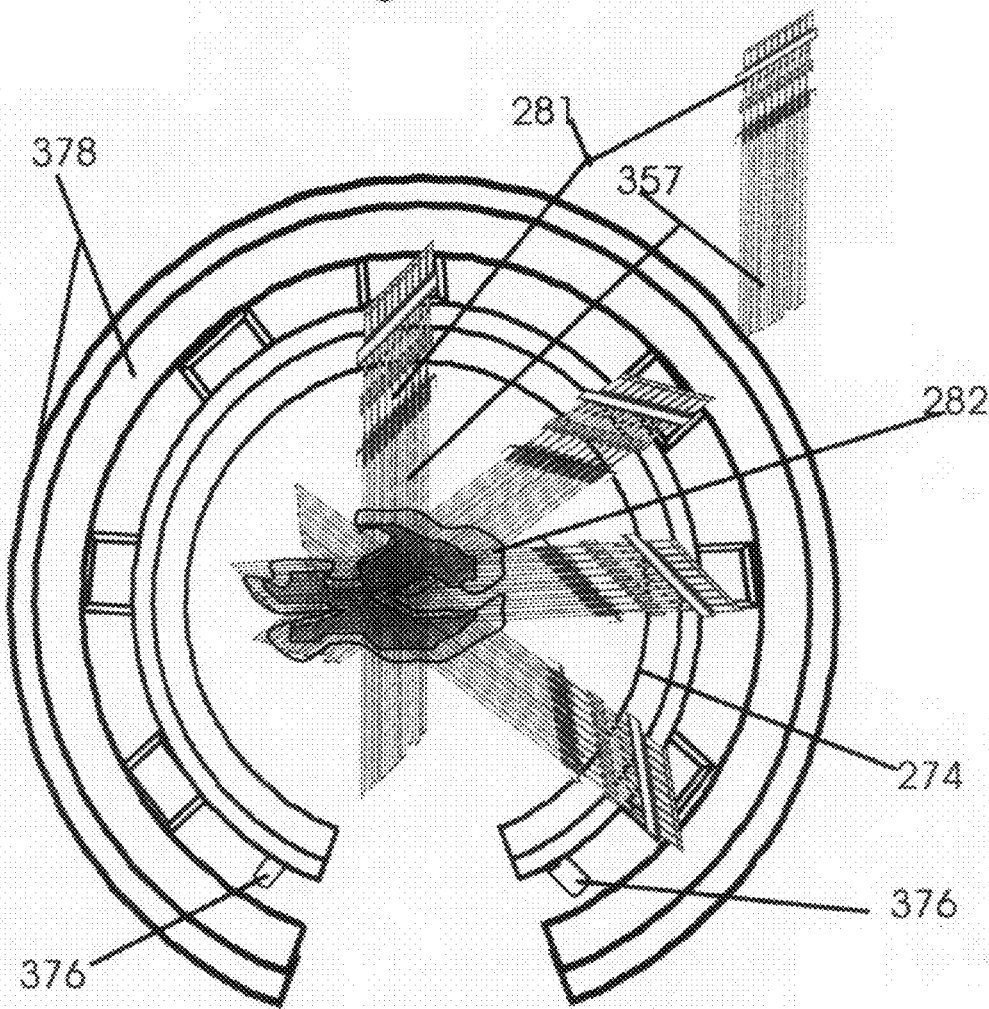

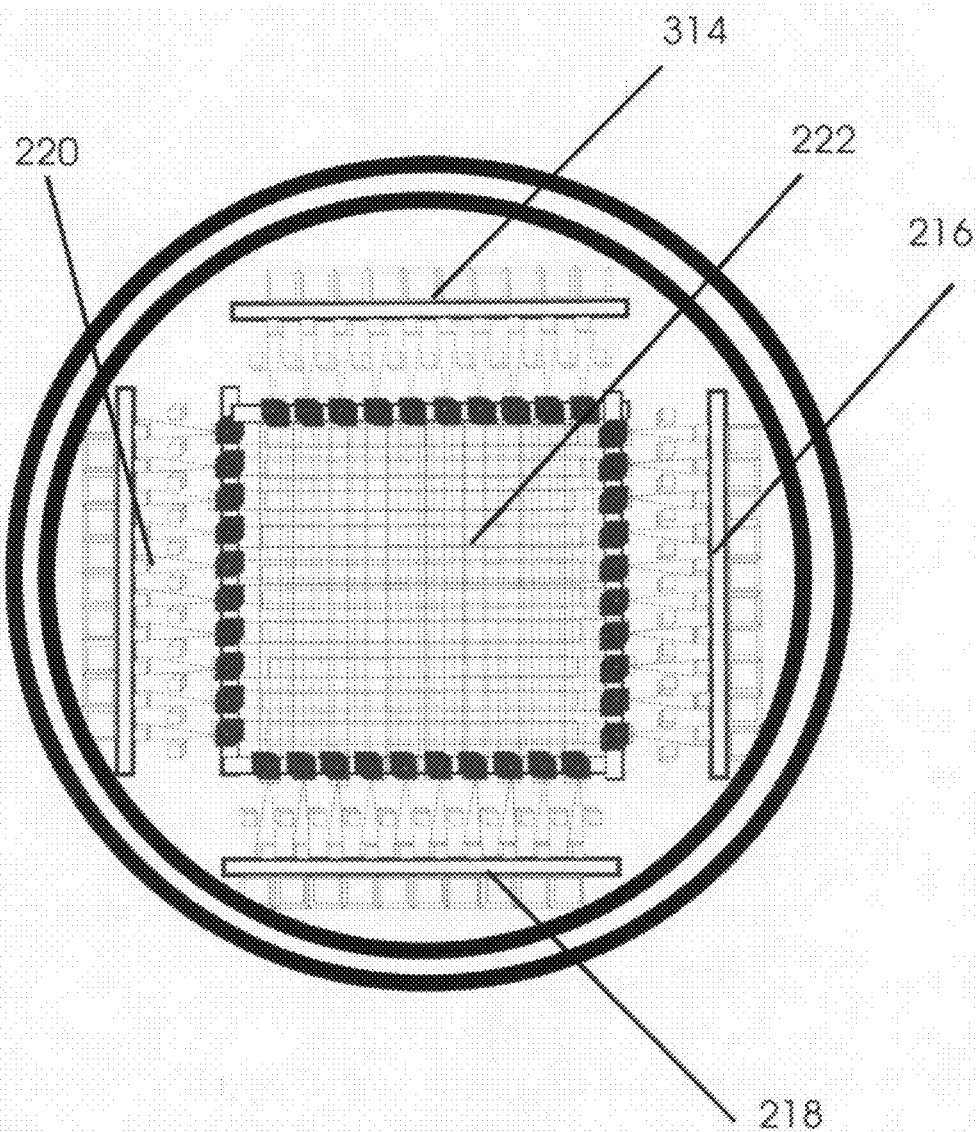

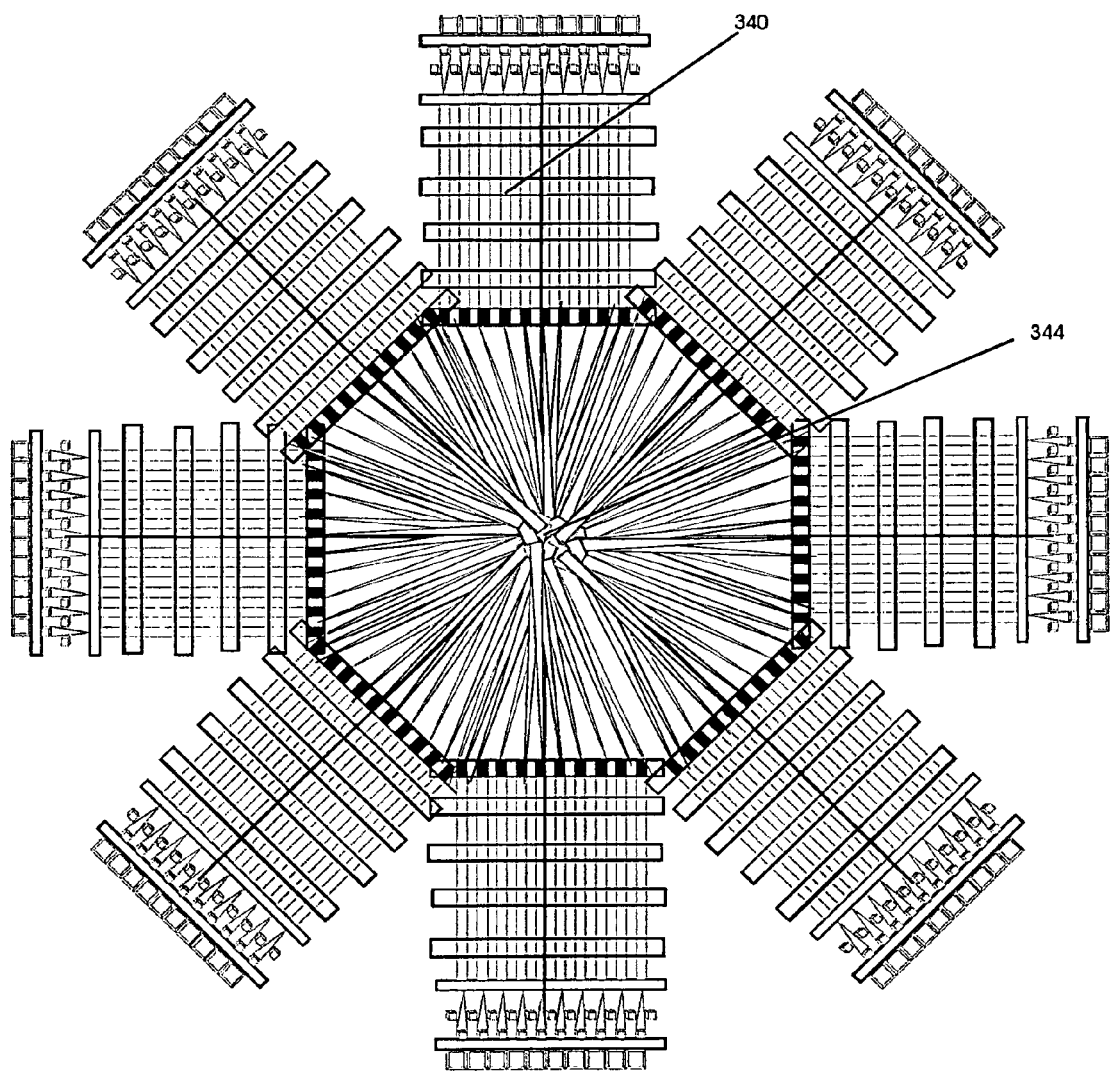

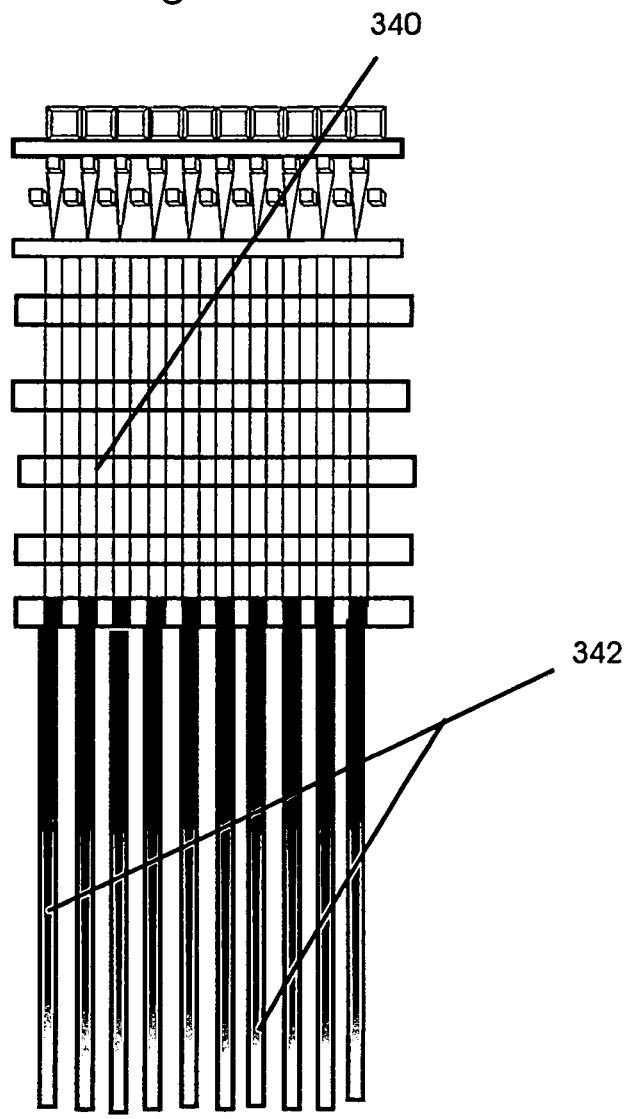

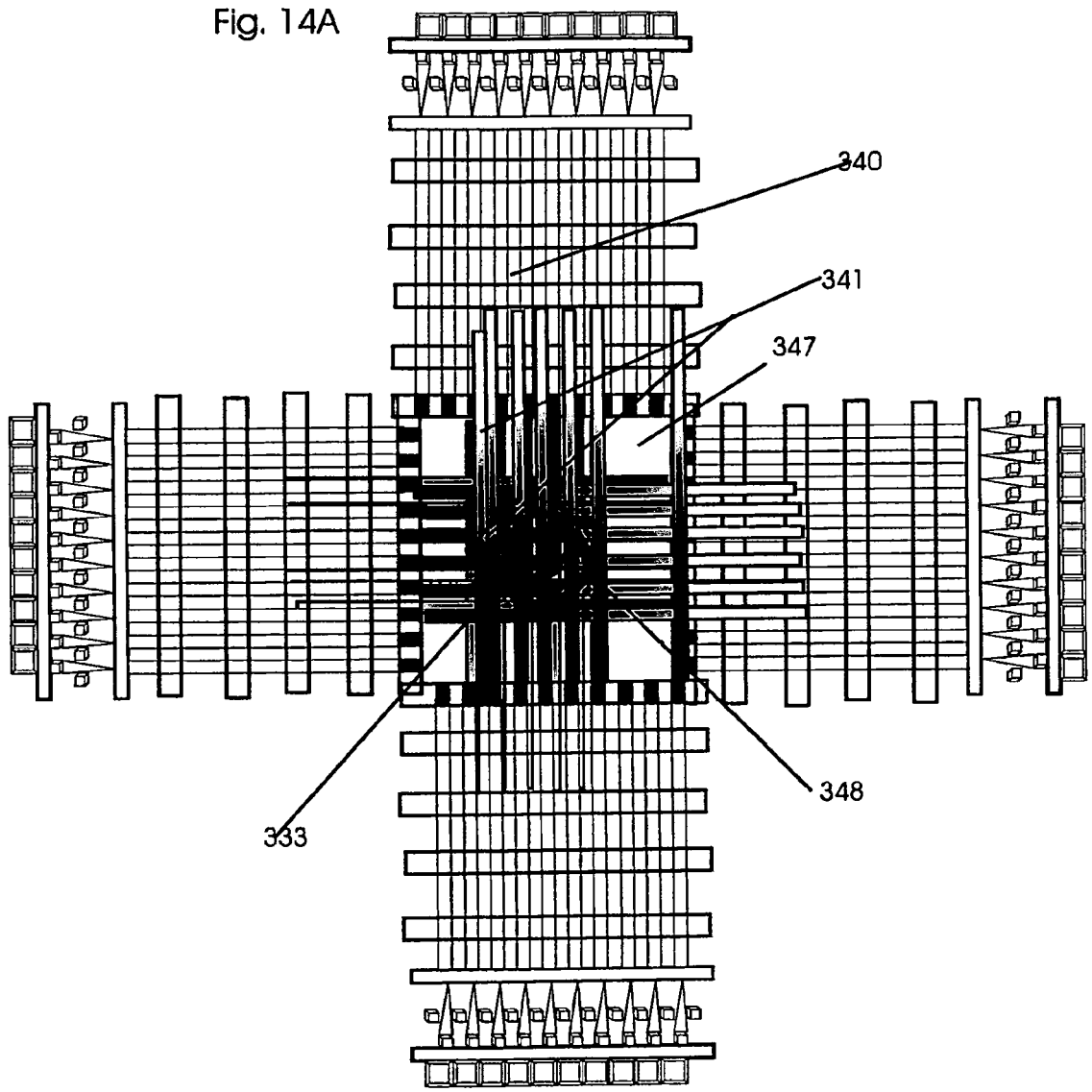

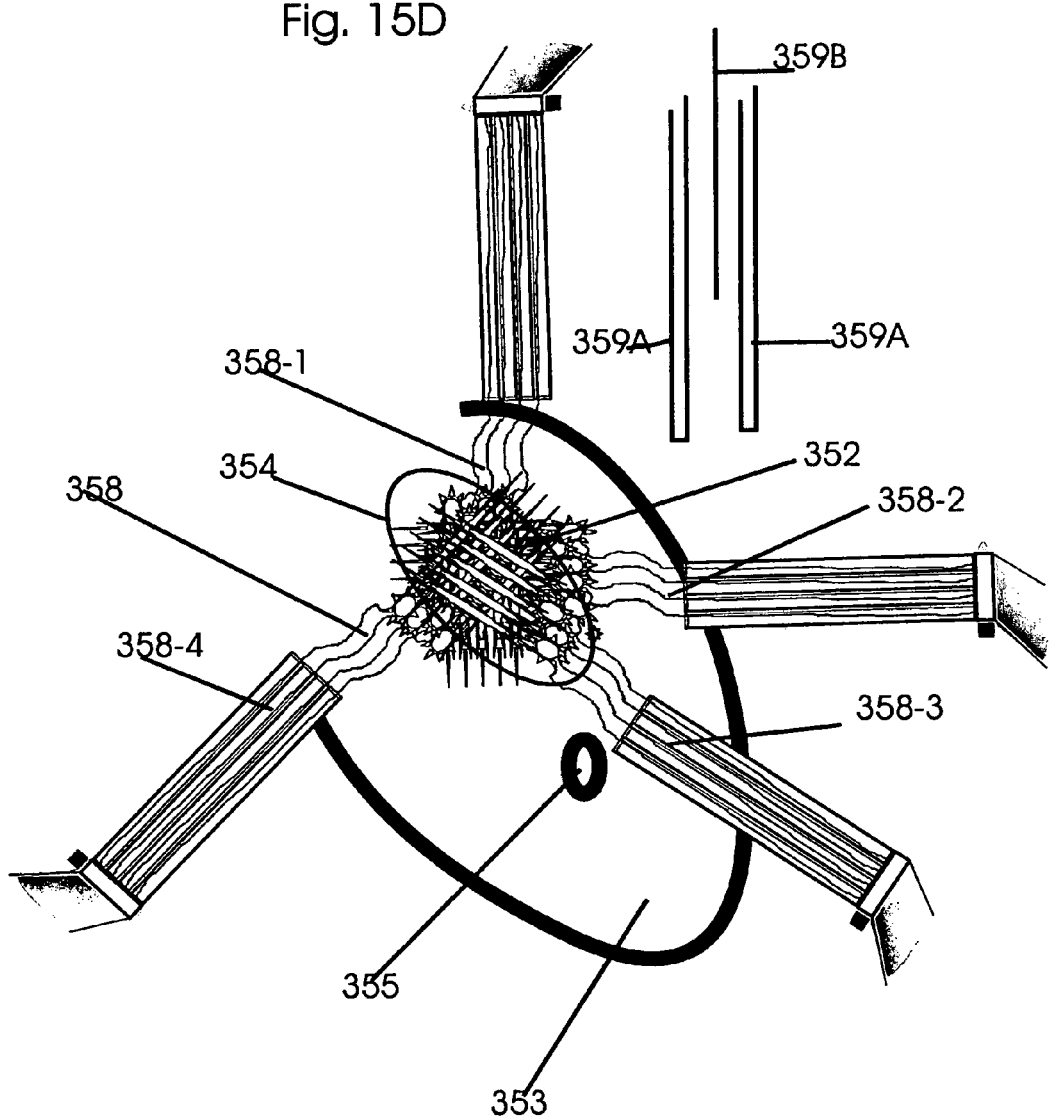

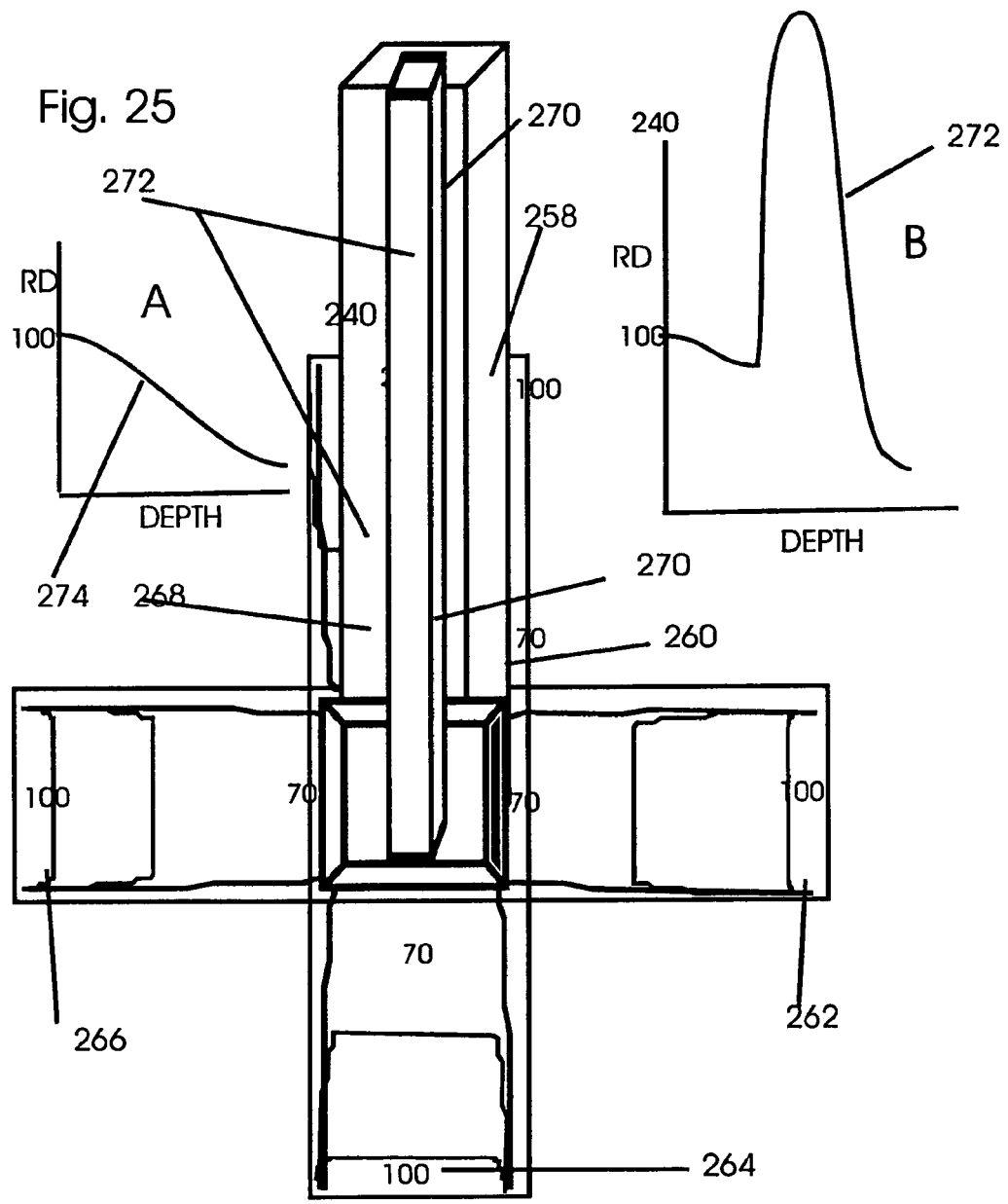

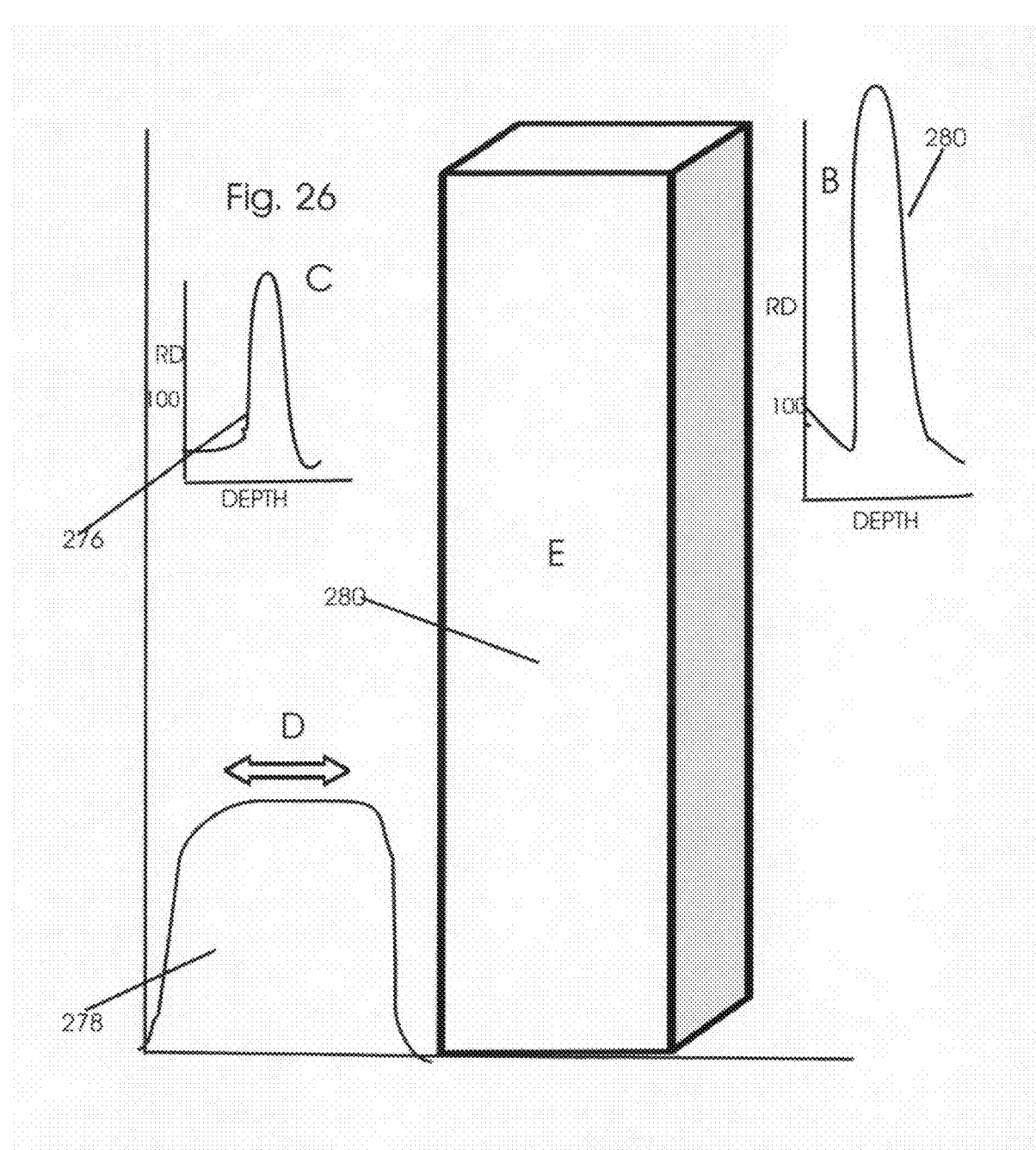

IMAGE GUIDED INTRAOPERATIVE SIMULTANEOUS SEVERAL PORTS MICROBEAM RADIATION THERAPY WITH MICROFOCUS X-RAY TUBES

FIELD OF INVENTION

X-ray beam therapy, class 378, 424, 530

FEDERALLY SPONSORED RESEARCH

None;

SEQUENCE LISTING

Table of Contents attached

BACKGROUND OF THE INVENTION

Synchrotron high dose rate microbeams with dose rate exceeding 20 Gy/sec is curative even for the most radiation resistant tumors like the glioblastoma multiforme (Slatkin and Dilimanian). This invention is aimed at similar high dose rate radiation therapy but with much more affordable and easily manageable microbeams from microfocus X-ray tubes that are configured to provide multiple simultaneous interlaced microbeams for simultaneous several ports irradiation. Their additive high dose rate is close to that of high flux synchrotron radiation.

Generally, after the diagnosis of malignant diseases it is treated by surgery, radiation therapy and chemotherapy. There are also an increasing number of benign diseases that are treated with radiation and chemotherapy. The methods of high dose rate radiation therapy help to treat cancer and benign diseases with curative intent and organ preservation. It sterilizes both "differentiated" cancer cells and the chemotherapy and radioresistant "cancer stem cells". It leads to more cancer cure and control. After destroying the diseased cells by the peak of the microbeams, the normal cell regeneration from the valley of microbeams restores the organ functions in both benign and malignant diseases.

The radiobiological advantages of all filed simultaneous radiation therapy (AFSRT) with super high additive dose rate at isocenter from multiple simultaneous beams are described by this applicant. They include provisional patent application 60/790,192, filed on Apr. 6, 2006 (1), non-provisional patent application Ser. No. 11/784, 398 filed on Apr. 5, 2007 (2) and its continuation application Ser. No. 11/974,876 filed on Oct. 15, 2007 (3), "Multiple medical accelerators and kV-CT incorporated radiation therapy device and semi-automated custom reshapeable blocks for all field synchronous image guided 3-D conformal-intensity modulated radiation therapy"; Provisional patent application 60/872,117 filed on Nov. 30, 2006 (4), its non-provisional patent application and Ser. No. 11/998,063 filed on Nov. 27, 2007, now U.S. Pat. No. 7,835,492 (5)"Lethal and Sublethal Damage Repair Inhibiting Image Guided Simultaneous All Field Divergent and Pencil Beam Photon and Electron Radiation Therapy and Radiosurgery"; Provisional patent application 60/927,622 filed on May 3, 2007 (6) and its non-provisional patent applications and Ser. No. 12/151,014 filed on May 3, 2008, now U.S. Pat. No. 7,741,624 (7) "Single session interactive image guided simulation, field shaping, treatment planning and ultra short duration, super-high biological dose rate all field simultaneous or sequential radiation therapy and radiosurgery", none-provisional patent application Ser. No. 12/459,120 filed on Jun. 25, 2009 "Few seconds beam-on time breathing synchronized image guided all fields simultaneous radiation therapy combined with hyperthermia (8), non-provisional patent application Ser. No. 12/655,825 filed on Jan. 7, 2010, "System and method for all filed simultaneous radiation therapy and concealed object screening using inverse Compton scattering and its spent electron beam" (9) and non-provisional patent application Ser. No. 12/799,949 filed on May 6, 2010 "Hybrid Phase Contrast and Molecular Image Guided All Field Simultaneous Radiation Therapy and Targeted Gene and Radioimmunotherapy with Monochromatic Beams from Multiple Simultaneous Micro Focus X-Ray Sources" (10).

The advantages of the AFSRT includes additive high dose rate associated much improved photon beam's RBE. Because of the additive high dose rate of AFSRT, the beam on time to treat a tumor is only a few seconds. It facilitates a simpler means for breathing and organ movements synchronized radiation therapy without the surrounding normal tissue's smearing with radiation or missing any portions of the tumor within a tumor.

Simultaneous Several Ports Microbeam Radiation Therapy with Monochromatic X-Ray Beams Monochromatic x-ray beam radiation therapy either with the interaction of infrared laser beam with accelerated electron beam or with monochromatic x-ray beam from an array of micro focus x-ray tubes with monochromating optics were described by this inventor before (9 and 10). In this invention, monochromatic x-ray beam from an array of miniature 10-150 kV micro focus x-ray sources are brought very close to surgically exposed tumor as single session intraoperative microbeam radiation therapy or to organs such as the breast for whole breast preserving breast cancer treatment without major surgeries including without gross biopsies. Alternatively, implantable miniaturized X-ray sources are implanted directly into the radiating organ as single session intraoperative microbeam brachytherapy. It minimizes radiation to the normal tissue and improves the dose and dose rate associated radiobiological effectiveness (RBE) close to that of high linear energy transfer (LET) radiation. The miniaturized 10-150 kV X-ray sources used in this invention includes small conventional microfocus x-ray tubes (SCM-X-ray tubes) for external contact radiation and X-ray sources suitable for both external radiation and interstitial radiation such as the electronic brachytherapy X-ray tubes (EBT-tubes), X-ray tubes based on carbon nanotube field emission (CNT-FE X-ray tubes) and miniaturized accelerators based on carbon nanotube field emission (CNT-FE accelerator).

The methods of intra operative radiation therapy eliminates the need for megavoltage radiation therapy accelerators that are generally used to spare the skin from high dose radiation and also for deeper penetration of the radiating beam through the normal tissue below the skin to reach the tumor at sufficient dose and dose rate. Since the 10-150 kV beams are directly applied to the tumor, there is no need for the radiating beam to penetrate through the skin and normal tissue below it to treat a tumor. Hence the 10-150 kV beams from small conventional microfocus x-ray tubes or from the CNT-FE X-ray tubes and CNT-FE accelerators are suitable for intraoperative single fraction radiation therapy. The alternative radiation therapy setup with combined micro focus x-ray tubes and megavoltage medical accelerator allows combined simultaneous megavoltage (MV) and kilovoltage (kV) radiation therapy as described in U.S. non-provisional application Ser. No. 12/799,949 (10). The intraoperative multiple simultaneous beam interstitial radiation therapy with multiple EBT-tubes or with miniaturized carbon nanotube field emission based interstitial implant x-ray sources (CNT-FEI-X-ray tube) likewise treats a tumor with minimal radiation toxicities to surrounding normal tissue.

Simultaneous beams from an array of 10-150 kV X-ray tubes brought very close to surgically exposed tumor or to an organ like the breast are capable of delivering high additive dose rate radiation to the exposed tumor or diseased organ without high dose to the skin. In one embodiment, micro focus x-ray tubes with small spot size of 10 to 50 µm and microbeam collimators with 5 to 25 µm sized openings are used to obtain monochromatic x-rays of 5 to 25µ width. Multiple simultaneous beams from multiple miniature x-ray tubes arranged in a circle around a surgically exposed tumor and all the beams from such x-ray tubes converging at a common isocenter located in a tumor facilitates the intraoperative additive high dose rate radiation to the tumor. However, its dose rate is nowhere near to that of synchrotron radiation. It is improved by bringing the X-ray tubes very close to the tissue that is radiated. The dose rate of a miniaturized micro focus x-ray tube at 3 cm depth in water is about 60 cGy/min Bruce D. J., Leu C. S., Betty, J. F., Shefer R. E., Clinical biological effectiveness of low energy x-rays emitted by miniature x-ray devices, Phys Med boil, 44: 323-333, 1999 (11). As described later in this invention, depending on the number of thermionic or CNT based x-ray tubes used for simultaneous beam radiation and their individual dose rate, its additive dose rate thermionic X-ray could reach about 10 Gy/sec and the additive dose rate for CNT based X-ray tubes could reach over 20,000 Gy/sec. For the CNT based X-ray tubes, the dose rate can vary from a few cGy to $10^4$ Gy/sec. It is not achievable with a present medical accelerator or from an orthovoltage tube. The quasi-parallel microbeams from just two CNT-based X-ray tubes placed at 90° angles and each having dose rate of $10^4$ Gy/sec can have additive dose rate of 20,000 Gy/sec which is similar to the Synchrotron X-ray's dose rate of about 20,000/sec. Since it is the intraoperative, additive dose rate from a number of simultaneous beams brought very close to the tumor and focused at the isocenter, the dose and dose rate to normal tissue surrounding the tumor or the diseased tissue is only that fraction of the dose and dose rate contributed by any one of the multiple beams. Furthermore, the peak and valley dose variation with significantly low dose radiation to the valley of microbeam radiation, the tolerance to microbeam radiation is significantly increased, to 200 Gy and much higher. It facilitates super-high-additive dose rate intraoperative conformal microbeam radiation therapy with minimal dose and dose rate to normal tissue surrounding the tumor or to a diseased organ.

The dose rate of an X-ray tube with small spot and 10µ line pair at 10 watts has 27 rads/min and its larger spot with 45µ line pair at 62.5 watts have 160 rads/min at 1 ft that is at 30.48 cm, say at 30 cm (12). If an array of miniaturized 24 X-ray tubes is configured around a tissue that is surgically exposed and it is to be irradiated from sagital, coronal and transverse directions and each tubes are kept at 45 degree apart and their simultaneous beams are focused on to an isocenter and the isocentric distance is 30 cm, then their additive dose rate at the isocenter is 27×24 that is 648 cGy/min. At 60 cm, this dose rate would decrease to its half due to the SSD factor of 30/60. Hence, the additive dose rates at 60 cm for 24 such microfocus X-ray tube is 648/2 is 324 cGy/min. At 100 cm distance its dose rate is about one third of the dose rate at 30 cm distance. Hence it is 648×0.3 which is 194 cGy/min or 1.94 Gy/min. It is 0.0323 Gy/sec. Similarly for the X-ray tube with larger spot size, 45µ line pair and dose rate of 160 cGys/min at 30 cm, the additive dose rate for such 24 X-ray tubes at 30 cm is (160× 24) which is 3,840 cGy/min or 38.4 Gy/min. At 60 cm distance from the source, its dose rate is 19.2 Gy/min and at 100 cm it is 11.52 Gy/min or 0.192 Gy/sec. It is nowhere close to the 20,000 Gy/sec dose rate for the synchrotron radiation. Hence the combined radiobiological results of 24 microfocus X-ray tubes placed at 100 cm distance from the radiating tissue cannot be compared with that of synchrotron radiation.

However, this additive dose rate can be significantly increased by bringing the X-ray tubes close to the tissue that is radiated. By bringing the X-ray tubes from 30 cm distance to 2 cm from the tissue that is irradiated, that is almost like in contact radiation therapy, this additive dose rate at the isocenter from 24 simultaneous beams from 24 X-ray tubes will increase to 4 folds. Hence the dose rate for one X-ray tube with small spot, 10µ line pair and 27 cGy/min at 30 cm distance is 432 cGy/min at 2 cm distance from the tissue that is radiated. The additive dose rate for 24 simultaneous beams from 24 X-ray tubes with 10µ line pair is 432×24 that is 10,368 cGy/min at the isocenter. It is 103.68 Gy/min or 1.728 Gy/sec. Similarly, the dose rate for one X-ray tube with larger spot, 45µ line pair and 160 cGy/min at 30 cm distance is 2560 cGy/min at 2 cm distance from the tissue that is radiated. The additive dose rate for 24 simultaneous beams with such a setup is 2,560×24 that is 61,440 cGy/min at the isocenter. It is 614.4 Gy/min or 10.24 Gy/sec. With inserted diffraction filter in the path of the x-ray beam, this dose rate will decrease but still high enough for intraoperative multiple simultaneous beam radiation therapy. With adequate lead shielding, the leakage radiation is in the range of <1 µSv/h at any point on the x-ray tube. It is less than 0.0167 µSv/min or 0.0003 µSv/sec. By increasing the number of tubes, this leakage radiation remains as the same. It renders added radiation safety. By bringing the X-ray tubes close to the tissue that is irradiated, that is like contact radiation therapy, the additive dose rate at the isocenter has significantly improved but still not as high as the 20,000 Gy/sec dose rate of synchrotron radiation. However with additive dose rate of just two CNT based X-ray tubes, each with $10^4$ Gy/s, its dose rate can be brought close to synchrotron X-ray's dose rate of about 20,000/s. It is not achievable with a present medical accelerator. Two CNT-based X-ray tubes placed at 90° angles from each other and each having the dose rate of $10^4$ Gy/sec can have additive dose rate of about 20,000 Gy/sec at the isocentric intersection of their quasi parallel microbeams. If it were such 4 or 6 CNT based X-ray tubes arranged at 45° angles to each other, their additive dose rate is about 40,000 or 60,000/ sec. Taking advantage of the peak and valley dose difference of microbeam radiation, a tumor could be treated with very high dose, over 200 Gy and higher with minimal toxicity to normal tissue. By spacing the microbeam at 200 to 400 µm distance from each other, the valley dose in normal tissue is much decreased (20). It allows safe administration of over 700 Gy to the brain without much toxicity (20).

The dose contribution from Auger and characteristic radiation from the interaction of tuned monochromatic x-ray to the k-shell binding energy of the high Z-element nanoparticles bound to the tumor or implanted into it fills in the valley dose. Hence the increased spacing of the microbeam do not minimize dose to the tumor. Together with the characteristic radiation produced by the microbeam itself and the added Auger and characteristic radiation produced from the interaction of the tuned monochromatic X-ray with implanted high Z-element's k-shell that fills in the low dose regions in the valley of the microbeams at the isocenter makes the isocentric tumor-dose as homogenous. It allows wider spacing of the microbeams. It minimizes radiation toxicity to the normal tissue through which the microbeams travels towards the isocentric tumor. It renders additional tumor specific locally confined homogenous radiation to the isocentric tumor. With CNT X-ray tube's microbeam and with k-shell enhanced characteristic and Auger radiation only within the tumor, the dose and the dose rate within the tumor is made even higher than it is possible with the synchrotron X-rays. It allows safer administration of over 700 Gy to the tumor without much toxicity by wider spacing between the microbeams. Such high dose and dose rate radiation therapy is not possible with present medical accelerators.

In U.S. Pat. No. 7,643,610—by Dilimanian (Dilmanian F. A. U.S. Pat. No. 7,643,610 issued on Jan. 5, 2010: Method and Device for Performing Stereotactic Microbeam Radiation Therapy two types of stereotactic microbeam radiation therapy (SMRT) is described, the SMRT with X-ray tubes and the synchrotron based SMRT (Dilmanian F. A. U.S. Pat. No. 7,643,610 issued on Jan. 5, 2010: Method and Device for Performing Stereotactic Microbeam Radiation Therapy, column 3, lines 36-45, (13) and column 4, lines 6-25 (14). In one embodiment in U.S. Pat. No. 7,643,610, 10 X-ray tubes are configured on to a hemispherical gantry and treating a tumor with 5 pairs of orthogonal beams, 10 X-ray tubes, as simultaneously or sequentially (Dilmanian F. A. U.S. Pat. No. 7,643,610 issued on Jan. 5, 2010: Method and Device for Performing Stereotactic Microbeam Radiation Therapy, column 12, line 23 (15), column 15, lines 10-11 (16). The dose rate for each of these tubes is described as having 1 to 5 Gy/min at 100 cm distance from the X-ray tube (Dilmanian F. A. U.S. Pat. No. 7,643,610 issued on Jan. 5, 2010: Method and Device for Performing Stereotactic Microbeam Radiation Therapy, column 14, lines 60-62 (17). Such high dose rate at 100 cm distance from the source can be achieved only with larger focal spit size, that increases the penumbra of the beam. Simultaneous beams from such 10 orthovoltage tubes could be 10-50 Gy/min at the isocenter where the beams cross with each other. It is 17 to 83 cGy/sec or 0.17 to 0.83 Gy/sec. This disadvantage of the X-ray tubes as it is used in US patent is recognized in this patent (17). Hence, its dose rate associated RBE cannot be compared with 20,000 Gy/sec Synchrotron radiation's dose rate associated RBE. Its radiobiological effectiveness for tumor cure and control is much inferior as compared to that of synchrotron radiation. It definitely cannot provide anywhere closer to the radiobiological effectiveness of synchrotron radiation with dose rate of 20,000 Gy/sec in treating a tumor. The other major disadvantage of the X-ray tube based microbeam radiation as taught in U.S. Pat. No. 7,643,610 is its 0.8 mm sized large penumbra (18). Such large penumbra is associated with the use of 0.7 mm wide microbeam in U.S. Pat. No. 7,643,610 (19). Leksell Gamma Knife with cobalt-60 based microbeam is also known to have such large, 0.8 mm sized penumbra (20). With 1 mm wide microbeam radiation, there was visible, macroscopic brain damage in mouse brain even at lower dose of 140 Gy while when the microbeam width was 25 μm, 4,000 Gy could be administered to the brain without such brain damage (20). As a compromise, 25 to 75 μm wide microbeams was elected in the experiments reported by Serduc et al (20). It avoided such gross tissue damage from microbeam radiation. Using the 1 mm wide microbeam as in U.S. Pat. No. 7,643,610 (19) is a significant hazard as it increases the normal tissue damage and necrosis.

By decreasing the distance from the X-ray tube to the tissue that is surgically exposed will increase the dose rate to the tissue that is irradiated. Such increase in each X-ray tube's dose rate will also increases the additive dose rate at the isocenter from multiple simultaneous beams. With multiple simultaneous beams from multiple microfocus X-rays, the additive dose rate can be brought closer to synchrotron radiation with 20,000 Gy/sec. For the CNT based X-ray tubes, the dose rate can vary from a few cGy to $10^4$ Gy/sec. At 1-2 μA emission current it is 1000 Gy/sec (21). Orthogonal arrangement of just two CNT-based X-ray tubes and their beams intersecting at the isocenter gives additive dose rate of 20,000 Gy/sec. The dose rate of Synchrotron X-ray microbeam radiation used to study the tolerance to mouse brain was 16,000 Gy/sec (20). Hence it has the same radiobiological qualities synchrotron radiation with 20,000 Gy/sec. It improves the sterilization of the "differentiated" and dormant cancer stem cell in a tumor. The additive dose rate of intraoperative contact radiation therapy with 24 X-ray tube's simultaneous beams with 10.24 Gy/sec as described in one of the embodiments in this invention is relatively closer to the synchrotron radiation. This dose rate also has the high Synchrotron dose rate associated radiobiological effectiveness. This is much different than to the 0.17 to 0.83 Gy/sec dose rate microbeam radiation therapy described in U.S. Pat. No. 7,643,610—by Dilimanian (17), which include radiation therapy with 10 simultaneous microbeams (15, 16).

Electronic Brachytherapy X-Ray Tubes (EBT-Tubes) and Simultaneous Multi-Bam Brachytherapy Recently, electronic brachytherapy with miniaturized X-ray tubes was introduced in clinical practice. In this new brachytherapy system, instead of the classical radioactive isotope a miniaturized X-ray tube is used as the radiation source. It was reviewed by C. C. Park et al of the American Society for Therapeutic Radiology and Oncology's (ASTRO) Emerging Technology Committee and its report on electronic brachytherapy was published in Int. J. Radiation Oncology Biol. Phys. 2010:76: 963-972 (22). The origin of the miniaturized x-ray tubes for brachytherapy can be traced back to a number of US patents dating back to 1973 onwards. While the following is not a complete list of all these patents, they includes:

U.S. Pat. No. 3,714,486, Jan. 30, 1973, McCrary, Field emission X-ray tube (23), U.S. Pat. No. 5,090,043, Feb. 18, 1992, Parker, W. J.: X-ray micro-tube and method of use in radiation oncology (24), U.S. Pat. No. 5,153,900, Oct. 6, 1992: Nomikos, P. M., Miniaturized low power X-ray source, (25), U.S. Pat. No. 5,165,093, Nov. 17, 1992, Miller R. B. and Smith J. R. Interstitial X-ray needle (26), U.S. Pat. No. 5,428, 658, Jun. 27, 1995, Oettinger, P. E., X-ray source with flexible source (27), U.S. Pat. No. 5,566,221, Oct. 15, 1996, Smith D. O., Apparatus for applying a predetermined X-ray flux to an interior surface of a body cavity (28), U.S. Pat. No. 5,748,699, May 5, 1998, Smith. D. O.: Apparatus for applying a predetermined X-ray flux to an interior surface of a body cavity (29), U.S. Pat. No. 5,729,583, Mar. 17, 1998: Cha-Mei Tang and Deslattes, R. D., Miniature X-ray source (30), U.S. Pat. No. 6,108,402, Aug. 22, 2000, Chornenky V. I: Diamond Vacuum Housing for miniature X-ray devise (31), U.S. Pat. No. 6,134,300, Oct. 27, 2000, Trebes J. E. et. al: Miniature X-ray source (32), U.S. Pat. No. 6,661,875, Dec. 9, 2003, Greenwald, A. C. Hlayerson, W. D., Catheter tip X-ray source (33), U.S. Pat. No. 6,319,188, Nov. 20, 2001, Lovoi, P. A., Vascular X-ray probe (34) and U.S. Pat. No. 6,987,835 issued Jan. 17, 2006, Lovoi P. A.: Miniature X-ray tube with micro cathode: (35), U.S. Pat. No. 6,324,257, Nov. 27, 2001, Halavee, U. Radiotherapeutic device and use thereof (36), U.S. Pat. No. 6,289,079, Sep. 11, 2001, Chornenky V. I et al.: X-Ray device and deposition process for manufacture (37), U.S. Pat. No. 6,415,016, Jul. 2, 2002, Chomenky V. I et al.: Crystal quartz insulating shell for X-Ray catheter (38), U.S.

Pat. No. 6,438,206, Aug. 20, 2002, Shinar G. et al.: Continuously pumped miniature X-ray emitting device, and system for in situ radiation treatment (39), U.S. Pat. No. 6,477,233, Nov. 5, 2002, Ribbing C. et al.: Miniature x-ray source (40), U.S. Pat. No. 6,580,940, Jun. 17, 2003, Gutman G., X-ray system with implantable needle for treatment of cancer, (41), U.S. Pat. No. 6,623,418, Sep. 23, 2003, Smith L., Radiation source; plurality of sources at the treatment site, column 1, line 64, individual source, simultaneous or sequential beam possible, for vascular stenosis (42), U.S. Pat. No. 6,553,096 awarded to Zhou O. Z and Lu J on Apr. 22, 2003, X-ray generating mechanism using electron filed emission cathode (43), U.S. Pat. No. 7,771,117, Aug. 10, 2010, Kim J Uk and Choi H. Y., X-ray system for dental diagnosis and oral cancer therapy based on nano material and method thereof (44), U.S. Pat. No. 6,718,012, issued Apr. 6, 2004, Ein-Gal M., Electromagnetic wave energy emitter (45), U.S. Pat. No. 5,854,822, issued Dec. 29, 1998 to Chornenky V. I et al, Miniature X-ray device having cold cathode, (46), U.S. Pat. No. 6,487,272 issued Nov. 26, 2002 to Kutsuzawa H, Penetrating type of x-ray tube and manufacturing method thereof, (47), U.S. Pat. No. 6,721,392, issued on Apr. 13, 2004 to Dinsmore, M., Optically driven therapeutic radiation source including a nonplanar target configuration (48), U.S. Pat. No. 6,771,737, issued on Aug. 3, 2004 to Kerslick et al, X-ray catheter with miniature emitter and focusing cup, (49), U.S. Pat. No. 6,799,075 issued on Sep. 28, 2004 to Chornenky et al., X-ray catheter (50), Patent application US 2009/0185660, dated Jul. 23, 2009 by Zou, Y., et al: Field emitter based electron source for multiple spot X-ray (51), Patent application US 2009/0245468 dated Oct. 1, 2009 by Zou et al: Field emitter based electron source with minimized beam emittance growth (52) and Patent application US 2009/030415 dated Dec. 10, 2009 by Fuerst et al., Field emission cathode and X-ray tube embodying same, (53), The principles of these patents are incorporated into this invention by their full reference.

In this invention, multiple commercially available electronic brachytherapy x-ray tubes or those built, including the carbon nanotube based x-ray tubes are configured in a circle around a radiating tissue to generate multiple simultaneous beams, all focused onto an isocenter for additive high dose rate intraoperative radiation therapy. Similar electronic brachytherapy X-ray tubes are also used for minimally invasive breast cancer treatment and for accelerated partial breast irradiation (APBI).

Carbon Nanotube Field Emission X-Ray Tubes (CNT-FE-X-Ray Tubes) and its Additive Dose Rate Close to that of Synchrotron Radiation As alternative to conventional microfocus X-ray tubes for intraoperative all field simultaneous precision radiation therapy, carbon nanotube field emission X-ray tubes (CNT-FE X-ray Tubes) are also used in this invention. Such CNT-FE-X-ray tubes with CNT cathode and MOFEST-MEME technology is used to construct both miniaturized X-ray tubes for intraoperative external beam radiation therapy and interstitial implant. Also carbon nanotube field emission interstitial X-ray tubes (CNT-FEI-X-ray Tubes), suitable as X-ray source for interstitial X-ray beam brachytherapy is also used in this invention.

CNT based microfocus x-ray tubes are disclosed in several patents issued in the past. Some of them are listed below. They includes U.S. Pat. No. 3,714,486 awarded to McCrary on Jan. 30, 1973: Field emission x-ray tube (23), U.S. Pat. No. 5,090,043 awarded to Parker W. J. on Feb. 18, 1992, X-ray microtube and method of use in radiation oncology (24); U.S. Pat. No. 6,108,402 awarded to Chornenky V. L., on Aug. 22, 2000, Diamond Vacuum Housing for miniature X-ray devise (31); U.S. Pat. No. 6,661,875 awarded to Greenwald, A. C. Hlayerson, W. D, on Dec. 9, 2003, Catheter tip X-ray source (33); U.S. Pat. No. 6,289,079, awarded to Chornenky V. I et al.: X-Ray Device and Deposition Process for Manufacture (37); U.S. Pat. No. 6,415,016, awarded to Chomenky V. I et al.: Crystal Quartz Insulating Shell for X-Ray Catheter (38); U.S. Pat. No. 6,438,206, awarded to Shinar, G et al.: Continuously pumped miniature X-ray emitting device and system for in-situ radiation treatment (39) U.S. Pat. No. 6,477,233, awarded to Ribbing C. et al.: Miniature x-ray source (40); U.S. Pat. No. 6,580,940, awarded to Gutman G., X-ray system with implantable needle for treatment of cancer (41), U.S. Pat. No. 6,623,418, awarded to Smith L., Radiation source (42), U.S. Pat. No. 6,553,096 awarded to Thou O. Z and Lu J on Apr. 22, 2003 (43). Patent application US 2009/0185660, dated Jul. 23, 2009 by Zou, Y., et al: Field emitter based electron source for multiple spot X-ray (51), Patent application US 2009/0245468 dated Oct. 1, 2009 by Zou et al: Field emitter based electron source with minimized beam emittance growth, (52) and Patent application US 2009/030415 dated Dec. 10, 2009 by Fuerst et al., Field emission cathode and X-ray tube embodying same (53), These patent principles are incorporated into this invention by their full reference.

Among the several method that are applied to construct field emission cathode for small multisource x-ray tubes is based on multilayer, precision thickness deposition of carbon nano-tube (CNT) on electrically conductive substrate that is suitable to be used with metal oxide semiconductor field-effect transistor (MOSFET) and microelectromechanical systems (MEMS). In this method, commercially available services for CNT deposition are used. Multilayer precision CNT is deposited on to the substrate using chemical vapor deposition method. It is deposited onto small silicon blanks at 130 micron tall blocks of aligned nano-tubes. Thousands of layers of CNT are deposited by chemical vapor deposition method (CVD) as blocks of multi-wall nano tubes (MWNT) by magnetron sputter method and ethylene as the carbon source and iron as catalyst at temperature over 700. The other methods suitable CNT deposition for this invention includes arc discharge, laser-assisted chemical vapor deposition, and high pressure carbon monoxide (HiPCO) method of deposition.

Using the micro electro mechanical systems (MEMS) and the metal-oxide-semiconductor field-effect transistor (MOSEFT) technologies miniaturized cathode-anode assembly is constructed. MEMS technology is used to construct thermionic micro cathode in miniature X-ray tube that consumes 0.05 watt power, U.S. Pat. No. 6,987,835 (35). In relative terms, an incandescent light bulb uses 25-100 watt. The thermionic cathode used in U.S. Pat. No. 6,987,835 is made of thin film deposits of tungsten, platinum or platinum coated material. It is a single beam, thermionic x-ray tube. MEMS technology is widely used for very small mechanical devices driven by electricity including in nanomechanical systems. Here it is adapted for low power consuming CNT based X-ray tube for interstitial implant with low kV. In this invention multiple simultaneous X-ray beams are generated with CNT based x-ray tubes. Each of these electron source CNT cathodes are connected to a MOSEFT control circuit. CNT tubes connected through the drain of an n-channel MOEFT has been successfully used to generate electron beams from an array of CNT cathodes (43). In this instance each CNT electron emitter was connected to the n-channel MOSEFT and the MOSEFT gate was connected to a 5V DC signal. CNT based cathode requires much reduced anode cooling requirements which is another advantage of it. In this invention, modified such MOSEFT and MEME configurations are used to construct miniaturized X-ray source for intraoperative radiation therapy. Other methods of CNT depositions and CNT cathode construction to generate a stream of electron that is focused on to an anode are also suitable as the multi-beam x-ray tube for this invention.

The CNT based X-ray system offers very narrow microbeams that are suitable for microbeam radiation therapy. Its width and dimensions are close to that of synchrotron microbeams. The dose rate of synchrotron X-ray microbeam used for radiation therapy is about 16,000 Gy/sec (20). The dose rate is controlled by the number of current pulses. For the CNT based X-ray tubes, it can vary from a few cGy to $10^4$ Gy/sec. At 1-2 µA emission current it is 1000 Gy/sec (21). Interlacing synchrotron parallel microbeam is very effective in treating very radioresistant tumors like glioblastoma multiforme without causing much damage to the normal tissue (54, 55).

Miniaturized Accelerators Based on Carbon Nanotube Field Emission (CNT-FE Accelerator) with Additive Dose Rate Close to that of Synchrotron Dose Rate The principles of the miniaturized electron accelerator are based on CNT cathode and MOSEFT-MEME technology. The electron is accelerated by changing the polarity of the electrical current that works as a drift tube. The accelerated electron strikes the transmission anode generating the forward propagating low energy X-ray beam ranging from 10-20 kV.

Radiation Therapy with Cnt-Fe Accelerators with Additive, Close to 200 Gy/Sc Dose Rate that Mimics Synchrotron Radiation Additive Dose Rate Close to that of Synchrotron The dose rate of high flux microbeam from Synchrotron X-ray microbeam used for high dose radiation to the brain with less toxicity is in the range of 16,000 Gy/sec (20). It is highly effective to treat even the very radioresistant tumors like the glioblastoma multiforme (54, 55). However, synchrotrons are not readily available to most of the cancer treatment centers in the world. As an alternative to synchrotron microbeam radiation, orthovoltage X-tube based microbeam radiation therapy is described in U.S. Pat. No. 7,643,610—by Dilimanian (13). Orthovoltage X-ray when used at a distance of 1 meter from the tissue that is radiated has much low intensity and hence very low dose rate. Hence its inferior RBE and poor tumor cure and control. Its radiobiological qualities cannot be compared with that of the synchrotron radiation with 20,000 Gy/sec. The dose rate for each of the orthovoltage X-ray tube as described in this patent 7643610 is 1 to 5 Gy/min (17). Hence, if the treatment is given with 10 simultaneous orthovoltage beams as described in U.S. Pat. No. 7,643,610, then the additive dose rate at the isocentric tumor could be 10 to 50 Gy/min. It is 17 to 83 cGy/sec or 0.17 to 0.83 Gy/sec. It definitely cannot provide anywhere close to the radiobiological effectiveness of synchrotron radiation. Hence no clinical advantage is realized from treating a patient with orthovoltage microbeams as described in U.S. Pat. No. 7,643,610. The effectiveness of synchrotron microbeam to cure the most radiation resistant glioblastoma multiforme (Slatkin, 54) is due to synchrotron radiation's 20,000 Gy/sec dose rate associated much improved RBE. At such high dose rate, there is no lethal and sublethal damage repair.

On the other hand, decreasing the distance from the X-ray tube to the tissue that is surgically exposed and irradiated by the methods of contact radiation therapy with multiple simultaneous beams, the additive dose rate at the isocenter is significantly increased. It is discussed before. With 24 simultaneous large spot 45µ line pair X-ray beams from sagital, coronal and transverse directions at close distance of contact radiation therapy, its additive dose rate is shown as high as 10.24 Gy/sec in one of the embodiments in this invention. It is not as high as the synchrotron radiation but it is closer to it than the 0.17 to 0.83 Gy/sec dose rate microbeam radiation therapy with simultaneous 10 orthovoltage X-ray radiation that is proposed in U.S. Pat. No. 7,643,610 (17). In other embodiments in this invention, CNT based X-ray sources are used. Its dose rate reaches up to 10,000 Gy/sec (21) which is even closer to the dose rate of synchrotron.

The dose rate for CNT based X-ray tubes at emission current 2 µA, frequency 100 Hz and duty cycle $5 \times 10^4$ is reported as $10^3$ Gy/sec. (21). In a Monte Carlo simulation of CNT based single X-ray pixel, it was shown that the dose rate varied from 0.35-13 Gy/min/mA at the isocenter for energies varying from 80-400 kV. This dose rate variation depended on the kind of anode material used. Higher dose rate was observed with tungsten or gold anodes and with aluminum and copper filters (56). In such instance, the additive dose rate of several CNT based X-ray pixels can make the dose rate close to that of Synchrotron microbeams dose rate and higher. At 0.5 cm distance from the source, it is about 20% of the 0-distance $d_{max}$ dose rate. (56). At 8 cm isocenter distance from the source, each pixel x-ray beam projects 2×2 mm on the radiating field. This 2×2 mm beam size at the isocenter matches with adjacent similar 2×2 mm beam and forms a continuous radiation filed at the isocenter (56). At 8 cm distance from the source to the isocenter, 5 pixels of 2×2 mm each, projects 1×2 cm on the radiating field for a 100 kVp beam (56). In this case, an array of 80 pixels will project 16×16 cm field on the radiating filed. However, at high dose of over 140 Gy, a 1×1 mm wide micro beam will cause macroscopic visible necrosis of the tissue radiated (20). With 25-75 µm wide microbeams, 700 gray dose could be administered safely (20). Eighty pixels of 75 µm would project a 0.6×0.6 cm field on the radiating filed. Sixteen such fields of 0.6 cm will cover a 10×10 cm field. Hence 16 small isocentric ports scanning radiation therapy will cover a 10×10 cm filed. The additive dose rate of the systems described here is in the range of 10 to 20,000 Gy/sec. Hence at 10,000 Gy/sec additive dose rate, the time to treat one scanning port at the isocenter to administer 100-200 Gy is 10 to 20 µsec. At 20,000 Gy/sec dose rate, the time to administer 100 to 200 Gy is 5 to 10 µsec. Depending on the system and its additive dose rate elected, the time to complete 16 isocentric scanning port in a 10×10 cm field is in the range of 80 to 320 µsec. Such isocentric scanning port radiation therapy is administered within one inspiration or expiration of a breathing cycle and a pulsation cycle. For intraoperative contact external beam radiation therapy, higher energy X-ray beams are used. For interstitial implant, low energy X-ray beams are used. The dosimetry for interstitial implant is calculated like for the $^{125}$I interstitial implant. Unfiltered 20 kV and below X-ray beam with the characteristic radiation is locally absorbed. When the treatment is by interstitial implant, this low energy spectrum of the beam is locally absorbed. The RBE of such locally absorbed low energy characteristic X-ray is similar to that of high LET radiation. The RBE of 10 kV x-ray is reported as 125 times higher than that for the RBE of higher energy x-ray beams (41). Hundreds of simultaneous X-ray pixels from a CNT based X-ray tubes and switching electively the number of pixel beams required to radiate a tumor that is in conformity with the tumor's size and shape and such beam's very high dose rate enables very high precision conformal radiation therapy. With such methods, the single fraction total dose that can be given to a tumor is several times higher than the conventional total dose that is presently used to treat a tumor. The narrow microbeam spares the normal tissue that is adjacent to its path. Hence the adjacent normal tissue receives very little radiation. After destroying the tumor tissue in the path of the microbeam, the normal cells migrate to the space occupied by the former tumor cells. This regeneration and refilling of the space occupied by the former tumor tissue accelerates the healing process of the tissue within a tumor. Because of such regeneration of the normal tissue in a tumor and low radiation to the normal tissue, the total dose that can be used to treat a tumor is very high and curative. It is about 200 Gy and higher. Compared to the 70-80 Gy used in conventional fractionated radiation therapy with broad beams, this single fraction 200 Gy and higher microbeam radiation therapy is highly curative. For the interstitial implant, the isocentric distance from the source as in the case of external radiation therapy is eliminated. It further improves the dose rate at the tumor site. Since the radiation is rendered to the tumor that is exposed intraoperatively, there is no need for the beam to pass thorough the skin. It eliminates the low energy radiation to the skin. Hence the toxicity to the skin from such low energy radiation is eliminated or significantly reduced. In this instance, the characteristic X-ray from 10-20 kV range X-ray is not a hazard but an advantage to treat the tumor with greater radiobiological effectiveness. The RBE of 10 kV x-ray is 125 times higher than that of the RBE of higher energy x-ray beams (41).

High Dose Rate Synchrotron Microbeam Radiation Therapy

Synchrotron microbeam radiation therapy can stimulate regeneration of the diseased nerve tissue. It can be used to treat chronic illness like the multiple sclerosis, demyelinating disorders, Parkinson's disease, macular degeneration, fibrosis of the lung, liver, and kidney, to stimulate revascularization of bone and to treat atrial fibrillation etc (54, 55). It is also very effective in treating brain tumors like the glioblastoma multiforme The advantage of treating a tumor with an array of narrow, about 50 μm widths and 200 μm inter-beam separation microbeam radiation is that it allows very high dose radiation to the tumor cells while the surrounding normal cells are spared from such high dose radiation. This beam's thickness is several hundred times smaller than the broad beams used in conventional radiation therapy. The synchrotron microbeams are ideal for microbeam radiation therapy (MRT). Its dose rate is about 20,000 Gy/s which has both practical and radiobiological applications. The microbeam radiation causes the bystander effect which is an expression of minimal radiation effect by the neighboring cells that are not radiated (57).

Microbeam Contact Radiation Therapy with Microfocus X-Ray Tubes and its Additive High Dose Rate Mimicking to that of Synchrotron Radiation The synchrotron microbeam's dose rate that is used for biological studies is about 16,000 Gy/sec (20). In this invention, the miniaturized thermionic X-ray tubes and CNT based field emission X-ray tubes are used for intraoperative radiation therapy. The dose rate of thermionic X-ray tube is much lower than the dose rate of CNT-based field emission X-ray tubes. The additive dose rate of 24 microfocus thermionic X-ray tubes configured at 45 degrees apart for contact radiation therapy through sagital, coronal and transverse orientations and all their parallel simultaneous microbeams passing through the isocenter where these beams acquires the broad beam characteristics is shown to have about 10 Gray/sec dose rate. With the inserted diffraction filter in the path of the x-ray beam, this dose rate will decrease. It is not as high as the dose rate from synchrotron radiation but adequate and sufficient for microbeam radiation therapy where the synchrotron microbeam capabilities are not available. In other words, multiple simultaneous micro beams from multiple microfocus thermionic X-ray tubes placed in short distance from the tissue that is radiated, can facilitates far advanced radiation therapy that is not available at the present. It does not need the construction of expensive treatment rooms which itself is prohibitively expensive to many institutions where the resources are much limited. With adequate lead shielding, the leakage radiation is in the range of <1 μSv/h at any point on the x-ray tube. It is less than 0.0167 μSv/min or 0.0003 μSv/sec. By increasing the number of tubes, this leakage radiation remains as the same. It renders added radiation safety.

Boost Radiation to Residual Malignant Stem Cells with Additive, High Dose Rate that Mimics Synchrotron Radiation The malignant stem cells are isolated from several solid tumors (58).

After treating a tumor by surgery, radiation therapy or chemotherapy and complete regression of the tumor with no further visible tumor in the imaging studies, most often there is still present microscopic residual malignant stem cell. These stem cells can proliferate. It results in tumor recurrence. When single fraction 312 to 625 Gy radiation was administered to rat glioblastoma multiforme with Synchrotron radiation there was no residual microscopic disease (54). Thus high dose and dose rate of 200 Gy/sec microbeam radiation therapy is curative even for the most radioresistant tumors like the glioblastoma multiforme.

Valley Dose Fill-in and Induced "Brag Peak"

An array of external or interstitial X-ray tubes and their simultaneous beams with their additive super high dose rate is used to create high additive biological dose rate radiation that has Brag-peak like characteristics. It is further enhanced with Auger transformation characteristic radiation from high atomic elements that is trapped into the tumor. It modulates the photon radiation therapy's RBE. The additive dose rate is the combined dose rate at depth for all the converging beams at the tumor site. The dose contribution from the interaction of tuned monochromatic x-ray to the k-shell binding energy of the high Z-element nanoparticles bound to the tumor or implanted into it renders additional tumor specific locally confined radiation with its own higher RBE. This Auger transformation characteristic radiation fills in the low dose regions in the valley that brings a homogenous enhanced dose distribution within the tumor that is treated. It also contributes to the "biological Brag-peak" at the isocentric tumor site. The combined Brag-peak like dose peak from the monochromatic x-ray and from the Auger transformation radiation has relatively well defined dose rise and fall within the tumor. The dose contribution from Auger transformation characteristic radiation and that of low kV x-rays like 10 kV is well defined. Both the sharply rising additive dose rate from the simultaneous monochromatic beams and the Auger transformation characteristic radiation from the interaction of monochromatic x-ray that is turned to the k-shell binding energy of the high Z-element nanoparticles bound to the tumor or implanted into it contributes to the combined Brag-peak like dose peak. This "biological Brag peak" falls off rapidly, almost like the dose fall off of the Brag-peak. When a medical accelerator is combined with this system, additional boost treatment with megavoltage photon and electron with the medical accelerator is elected if it is needed.

In present conventional radiation therapy planning with multiple beams, it is a common practice to illustrate the combined isodose from all treatment fields as additive isodose (59). However, it does not represent the additive isodose of simultaneous beams. Examples of multiple filed setup radiation therapy's isodose distribution are illustrated as combined dose from each beam (59). In this instance, each beam's dose contribution is a sequential event and hence its representation as combined additive isodose distribution is not exactly correct. In present practice of conventional radiation therapy, the beams to treat each separate field are switched on sequentially. After treating one field, there is an interruption of time that is taken to rotate the machine and to setup the second field and then to treat the second field. This process is repeated until radiation to the tumor through all the four fields is completed. The Dmax dose gradually decreases as the distance from Dmax to depth increase. Hence, in sequential treatment, the accurate representation of the isodose is not as additive isodose as it is commonly illustrated (59). When additive isodose of such interrupted treatment is used to calculate the dose, a correcting notation for the time interval to deliver each beam in sequence and its biological effect is needed.

Advantages of Intraoperative Radiation Therapy with Additive High Dose Rate Radiation As stated above, the advantageous of all field simultaneous intraoperative radiation therapy are many. It enables the highly localized conformal radiation therapy to the tumor volume and to its close proximity. Tumor volume and its surrounding tissue are determined at surgery both by the surgical team and the radiation oncology team. Presence or absence of regional lymph node metastasis from the surgical perspectives and from the radiation therapy perspectives are assessed by both surgeon and the radiation oncologist with a combined team effort. The overall growth pattern, the texture of the tumor per palpation and inspection, its color from the perspectives of well oxygenated or hypoxic all will help the radiation oncologist to determine the overall treatment planning.

The intraoperative radiation therapy eliminates the usual waiting period for the wound healing and patient's recovery to start the radiation. This minimizes the postoperative tumor burden. The conventional waiting period after surgery is an important period from the tumor biology, namely after exploration and surgical resection, the remaining tumor cells are stimulated for proliferation. This proliferative growth after traumatic gross surgical resection and tumor volume reduction can even enhance the dissemination of tumor cells and formation of micro metastasis at distant sites. The intraoperative radiation therapy minimizes and or eliminates this occurrence of postoperative proliferative tumor growth during the waiting period to start the radiation therapy. The methods of radiation therapy as in this invention do not interfere to wound healing after the surgery.

The low voltage, 10 kV multiple simultaneous beams radiation has no penetration to outside of the conformal radiation therapy field. It spares the normal tissue and enhances the RBE. The RBE of the 10 kV, high additive dose rate from multiple simultaneous beam exceeds the RBE of high LET radiation like that of neutron (1.5) and spread out heavy ions like carbon (2.2) (60). It helps to achieve more cure and control of the tumor. The conformal radiation is confined within the tumor and the normal tissue surrounding the tumor, the skin and the subcutaneous tissue all are spared from radiation. With no or minimal radiation to the normal tissue and the skin, there is no interference to wound healing from the radiation.

The methods of single fraction intraoperative radiation therapy with much improved RBE as it is in this invention are also much convenient and economical to the patient and to the society. Its expense is much lower than those for the present methods of radiation therapy including the week's long radiation therapy and the IMRT. The beam on time to complete this single fraction radiation therapy is only a few second. Hence the organ movements associated uncertainties of conformal radiation therapy is eliminated.

Intraoperative Interstitial Radiation Therapy with Multiple Simultaneous Miniature X-Ray Tubes As described under minimal invasive breast cancer treatment with CNT based miniaturized interstitial x-ray tubes, multiple CNT based miniaturized x-ray tubes of only a few mm in size are inserted into the tumor bed as single, double, triple or quadruple sets of X-ray sources that is sufficient to cover the entire tumor volume. A 10-kV tube without any additional applicator as in the case of a 50 kV X-ray tube will cover 0.5 cm depth dose. The 50 kV Intrabeam with applicator has similar depth dose of 0.5 cm. (62). Two parallel 10 kV CNT based miniature X-ray tube will cover 1 cm sized tumor. Four such staked tubes will cover a 2 cm sized tumor adequately. Several such miniature CNT based X-ray tubes are implanted into the tumor from varying angles to cover the radiation to the entire tumor volume and as simultaneous multi-beam x-ray source.

Oxygen Enhancement Ratio of Single Session Intraoperative Radiation with Oxygen Diffusion to Tumor The oxygen enhancement ratio for sparingly ionizing X-ray and y-rays is 2.5 at high doses. It is 1.6 for neutron and unit, 1.0 for highly ionizing α-particles (61) Oxygen must be present during or within microseconds after radiation for OER to be effective. Oxygen reacts with free ridicule R to form organic peroxide RO2 that is presumed to fix the non-recoverable radiation damage in tissue. In the absence of oxygen, the radiated tissue could recover from the radiation injury. Presence of only ½% oxygen is necessary to notice the marked dependency of oxygen to radiation sensitivity (62). At about oxygen partial pressure of 30 mm Hg, the 100% oxygen radiation sensitivity is observable. During the course of fractionated radiation therapy, the hypoxic cells in a tumor move to fully oxygenated cells as a result of reoxygenation. While the entire biological principles of hypoxia induced instability and its recovery is not well understood, direct application of very small amount of oxygen per capillary flow and diffusion to the surgically exposed tumor and maintaining the blood flow in the tumor without interruption will restore the anoxic cells to oxygenated cells. To restore the oxygen effect to radiation therapy the radiation is rendered after pretreatment of the tumor per directly implanted porous capillaries through with oxygen is made to flows to the tumor for half an hour and still continuing such oxygen treatment during and immediately after the radiation therapy. It avoids the need for fractionated radiation therapy to restore the oxygen effect to hypoxic cells when radiation therapy is administered as single or two or three fraction treatments.

Minimally Invasive Breast Cancer Treatment with Multiple Simultaneous Beams from Electronic Brachytherapy X-Ray Tubes Electronic brachytherapy with miniaturized X-ray tubes is an emerging technology for breast cancer treatment. As stated above it is a recent development for breast cancer boost radiation therapy. In this brachytherapy system, instead of radioactive isotope a miniaturized X-ray tube is used as the radiation source. Its present status is reviewed by C. C. Park et al (22). Miniaturized electronic brachytherapy sources are described in a number of patents that are also enumerated above. These patent principles are incorporated into this invention by their full reference. In this invention, such multiple commercially available electronic brachytherapy x-ray tubes or those built with carbon nanotube based x-ray tubes configured in a circle to generate multiple simultaneous beams focused onto an isocenter for additive high dose rate intraoperative radiation therapy or as multiple such sources inserted directly into the tissue as interstitial electronic brachytherapy sources to give multiple simultaneous beams. This invention's main goal is to treat a tumor with multiple simultaneous beams to achieve its radiobiological advantages.

Presently, in selected cases of radiation therapy of breast, electronic brachytherapy boost is included as a choice of treatment. During or after completing the conventional radiation therapy, a few sessions of boost radiation is delivered by electronic brachytherapy. The available systems for electronic brachytherapy include the balloon applicator based Axxent electronic brachytherapy system of Xoft and the Zeiss Intrabeam (22).

The Axxent electronic brachytherapy, Xoft system with the balloon applicator is used to treat the tumor bed with operating potential ranging from 40, 45 and 50 kV from a 2.2 mm diameter x-ray source and maximum beam current of 300 µA. It is equipped with spherical balloon applicators with diameter ranging from 3-6 cm or elliptical applicators of the size 5-6 by 7 cm. The shaft of this applicator is equipped with three separate lumens, two for balloon inflation and insertion of the electronic brachytherapy x-ray tube along the treatment pathway and a central lumen connected to several drainage holes at the apex and base of the balloon for drainage of seroma if it develops. This source assembly is connected to a high voltage cable. The power to the source can reach to a maximum of 15 watts. The source assembly and the high voltage cable are directed into the lumen of the applicator. The controller of this system is programmed to step up the source so connected to the high voltage cable and directed into the lumen of the applicator to each treatment position and for the dwell time for such source assembly at each treatment positions. Its dose rate is 60 cGys/min at 3 cm from the source axis. This source is designed to use for the treatment of only one patient; it is a single use electronic brachytherapy system. Its source is used to treat only one patient and the maximum number of fractions that can be delivered with once source is limited to ten. To treat a second patient, a second source is used, hence it is relatively expensive to maintain.

Because of the potential high dose to the skin, to the chest wall and the ribs for patients with small breast, this system cannot be used for accelerated partial breast irradiation (APBI) for such patients. This excludes 50% of patients with breast cancer for APBI. Even for those patients who are eligible for APBI with this system, there is the potential danger of balloon deflation and deformity. Because of this potential deflation and deformity of the balloon, the dose to the tumor bed, to tumor, to the skin and to the ribs can substantially vary. It can cause skin fibrosis, rib fracture and breast deformity. Furthermore, it is a single source dose rate system with maximum of 60 cGy/min. Its 40-50 kV range photon energy can cause more breast fibrosis and deformity. On the other hand, with multiple simultaneous beam brachytherapy treatment methods, the photon energy could be reduced to about 20-10 kV or even lower. It is also much easier to construct the multibeam electronic brachytherapy systems that need only 5-10 kV operating potential. It is in the Grenz-ray therapy range. The RBE of 10 kV x-rays relative to 200 kV X-rays is in the range of 1-10 Gy is reported for MCF-12A human mammary epithelial cells as 1.21 plus-minus 0.03 at 10% survival. (60). In the same study, RBE for induction of formation of micronuclei at dose range of 0.5 to 3.6 Gy was found to be 2.6 plus-minus 0.4 for the fraction of micronucleated cells with micronuclei" and 4.1 plus minus 1.0 "for the number of micronuclei per micronucleated cell" (60). In this study, it was also reported "an increase in RBE with decreasing photon energy down to the mean energy of 7.3 keV" (60).

The second electronic brachytherapy system is the Intrabeam system made by the Carl Zeiss surgical, Oberkochen, Germany. It is a miniaturized accelerator system that produce point source of low energy x-rays up 50 kV. Its drift tube tip with a gold target has 3.2 mm diameter that is operated with spherical applicators of varying size, ranging from 1.5 to 5 cm in diameter. The $D_0$ in water in Gy/min is calculated by dose rate in water multiplied by an applicator transfer factor (ATF) which is the ratio of the dose rate with and without the applicator as a function of the radius r, the distance from the target. The beam on time to deliver a dose of 5 Gy at 1 cm depth with 2.5 and 5 cm applicator is about 16 and 33 min respectively. Its technical features include that it is a single external beam source and the source and the high voltage are outside of the body, 50 kV peak x-rays, maximum beam current is 40 µA, probe diameter 3.2 mm and length of 10 cm and dose rate is fixed. It is a single dose delivery system. This source is designed to use for the treatment of any patients; it is not a single use electronic brachytherapy system as in the case of Xoft that is used to treat only one patient with one source and the maximum number of fractions that can be delivered with once source as limited to ten.

The dose rate of the Intrabeam system with 50 kV x-rays from a single source has similar depth dose characteristics at 5 mm depth as for the Xoft single source system but with variations due to different kind of applicators used in these systems. The Xoft single source system's applicator includes a balloon while the Intrabeam system uses spherical applicators of varying sizes, from 1.5 to 5 cm in diameter. The normalized depth dose at 0.5 mm depth for both single beam electronic brachytherapy systems with the applicators are approximately about 10 Gy.

Both the Xoft and the Intrabeam sources are thermionic sources that generate x-rays when the anode is bombarded with accelerated electrons from the cathode under temperature of over 1000° C. Its size is much larger when compared with the carbon nanotube based cathode and x-ray system. The carbon nanotube field emission cathode as it is used in this invention operates at room temperature. It reduces the heat generated by the x-ray production as it is with the thermionic x-ray production. Furthermore, its voltage is more easily controlled and it is very compact. It is highly suitable for simultaneous multibeam exposure external and interstitial radiation therapy with additive super-high dose rate at the tumor site where the multibeam meets and converges. It is further described under carbon nanotube cathode based external and interstitial x-ray tubes.

Cosmetic Whole Breast Preserving Stereotactic Core Biopsy Combined with Simultaneous Electronic Brachytherapy and a Course of Tamoxifen Before Invasive Surgical Biopsies There are a number of early stage breast cancers under the category of ductal carcinoma in situ (DIC) that are not palpable and are diagnosed per screening mammograms. Most of such patients will undergo the stereotactic breast core biopsy followed by operative biopsy and then the definitive treatments such as the breast preserving lumpectomy or simple mastectomy and postoperative radiation. Thus the surgical intervention of the tumor bed is a three step process, namely the stereotactic core biopsy followed by operative biopsy and the lumpectomy or simple mastectomy. All these surgical procedures have their proponents and opponents.

The stereotactic core biopsy can cause histologically proven tumor cell implants in normal breast tissue and the lymphatic and the blood vessels that are along the needle track (63, 64) Usually, there are weeks long waiting period before the second diagnostic open biopsy to remove the gross tumor and to establish a tumor free resection margin. If the resection margin is found to have residual tumor or if the resection margin is less than 1 to 2 mm from the tumor, a third open biopsy is performed to establish a tumor free margin with at least 2 mm distance from the tumor. This causes another week long waiting period for this third surgery. In the interim, the surgically violated tumor with tumor stem cell proliferative capacity will grow rapidly including within the normal breast tissue in which the needle tracks may have implanted tumor cells. After such three or four diagnostic surgical procedures, namely the stereotactic core biopsy, first open biopsy and if the margin is positive there is the second waiting period for the second open biopsy to get a clear surgical margin before the radiation therapy is started. There will be another waiting period of weeks for the surgical wound healing before the radiation therapy. If whole breast radiation is elected, it will last for about 5 to six weeks. If additional boost radiation to the tumor bed is also given it will also take additional time. Thus it will take about 4 months or more to complete the diagnosis and treatment from the time the suspicion of mammographic evidence for DCIS is reported. The psychological trauma, the lost days of work, the financial loss and burden all compounds to the distress for the patient. During this prolonged waiting period to complete the diagnosis and treatment, the residual tumor stem cell proliferates which ultimately influences the local tumor recurrence, the distant metastasis and the overall treatment outcome.

1. Intraoperative single fraction radiation therapy with or without whole breast radiation is shown to be both effective and safe for tumor local control for invasive breast cancer Vaidya J. et al., Targeted intraoperative radiotherapy for breast cancer (65). The Radiation Oncology, RTOG lists a number of past and present ongoing studies partial breast irradiation with the conclusion that the partial breast irradiation is safe and effective with or without whole breast radiation. Good to excellent cosmetic outcome and without any major complications by treating patients with invasive ductal cancers less than 3 cm in size and no lymph node metastasis was reported in a Phase II study consisting of single dose electron beam from a Mobetron before surgical excision by Kimple et al from university of North Carolina (66). Thus the intraoperative radiation therapy before the surgical excision of the tumor is safe and effective. In this invention, the electronic brachytherapy with multiple simultaneous low energy X-ray radiation as described under FIGS. 15B, 15C and 15D or with commercially available X-ray sources like the Xoft or Intrabeam (22) is combined with stereotactic breast core biopsy that further improves the cosmetic outcome and the therapeutic effectiveness as well as the time saved from the points of view of tumor biology due to tumor cell proliferation during the waiting periods of initial diagnostic interventional biopsy and the waiting period afterwards until the partial breast irradiation as reported by Kimple et al. Furthermore, this invention's locally absorbing low energy X-rays in the range of 10-20 kV within the tumor site improves the radiobiological effectiveness with low or no additional radiation to the normal tissue. In addition, in this invention, treating with tamoxifen also decreases the ipsilateral breast tumor recurrence (IBT). Like in Kimple et al's study, this invention's electronic brachytherapy is applicable mammographically detected non-palpable DCIS and also to invasive palpable tumors, However, in this instance the difference from Kimple's et al's study include that it is not using the complex and expensive electron beam source from a Mobetron accelerator, but with 10-20 kV CNT based X-ray source or with 30-50 kV commercially available X-ray sources based electronic brachytherapy which is also combined with tamoxifen that minimizes the importance of residual tumor at the tumor margin. More importantly, treating the breast cancer with tumor stem cell sterilizing 200 Gy and higher dose is more effective for tumor cure and control. Conveniently, it is a combined with one step stereotactic breast core biopsy to make the diagnosis and instant electronic brachytherapy if the tumor is proven to be malignant. It does not wait for later intraoperative external electron beam radiation therapy after the first diagnostic biopsy as in the case of Kimple et al's method of treatment. In this invention although breast biopsy is recommended about 3 to six months after treating DCIS, it is expected that no residual tumor will be found after the combined radiobiologically very effective 200 Gy and higher dose simultaneous CNT based 10-20 kV X-ray parallel microbeams. The dose that can be delivered with parallel micro beam without much toxicity is in the range of 100-500 Gy (20). The dose that can be delivered as a single intraoperative boost dose with a commercial 30-50 kV X-rays is 20 Gy (67). Hence its effectiveness to cure the tumor is much lower. Still with combined tamoxifen and intraoperative single session radiation, it is much more effective than the other methods radiation. It may lead to no residual tumor when later biopsy is taken. Furthermore, if the radiation is given with parallel micro beams, the whole breast and tumor bed radiation dose could be increased to over 100 Gy that is well tolerated without many side effects. The rat skin tolerance dose for microbeam is in the range of 5,000 Gy that is 500,000 cGy (68). Rat brain normal tissue tolerance dose for synchrotron microbeam is in the range of 312 and 625 Gy that is in the range of 31,200 to 62,500 cGy (69). Thus when radiation therapy is rendered with parallel microbeam with broad beam effect at the tumor site, the curative effect of radiation is very high and the tolerance dose to the normal issue is also extremely high. Hence much higher than the conventional 50-60 Gy total dose radiation can be administered safely.

In U.S. Pat. No. 7,643,610—by Dilimanian (70) and (71) a method of microbeam radiation therapy to a focal breast tumor with orthovoltage X-ray at 1 meter distance is described. Because of the poor dose rate of the orthovoltage X-ray beam, 0.17 to 0.83 Gy/sec, it does not offer the same radiobiological advantages of stereotactic microbeam radiosurgery with synchrotron radiation with the dose rate of 20,000 Gy/sec. The tumor recurrence is primarily due to conventional radiation therapy's inability to sterilize cancer stem cells. The "differentiated" cancer cells might be sterilized with conventional radiation therapy but the residual radioresistant cancer stem cells could cause tumor recurrence. The reason for tumor bed tumor recurrence after surgery and radiation therapy for breast cancer seems to be associated with the conventional radiation therapy's inability to sterilize the cancer stem cells. In U.S. Pat. No. 7,643,610—by Dilimanian (70, 71) X-ray tube based SMRT and synchrotron based SMRT are disclosed and assumes that their radiobiological effectiveness is similar. Because of the vast difference in their dose rates, X-ray tube based SMRT with 0.17 to 0.83 Gy/sec and the synchrotron based SMRT with 20,000 Gy/sec, their ability for tumor cell kill and tumor cure are not comparable. The low dose rate conventional radiation therapy is less effective for sterilization of the cancer stem cell.

On the other hand, decreasing the distance from the X-ray tube to the tissue that is surgically exposed and irradiated by the methods of contact radiation therapy with multiple simultaneous beams, the additive dose rate at the isocenter is significantly increased. With 24 simultaneous thermionic X-ray tube's beams, its additive dose rate is previously shown as high as 10.24 Gy/sec, With CNT based X-ray tubes it could reach up to 10,000 Gy/sec. While synchrotron based SMRT is not available to most cancer treatment centers, the thermionic and CNT based X-ray tube based SMRT could be made available to most cancer treatment centers. It will facilitate whole breast preservation radiation therapy without gross breast tissue removal, including removing breast tissue by gross biopsies.

If external microbeam from microfocus X-ray tubes is used, the skin toxicity is reduced by decreased total skin dose by administration of the total dose through a number of fields, up to 24 fields and the pencil microbeam's more penetrating capability. Also the normal tissue regeneration capability when the method of radiation is SMRT helps to heal the radiation damage to normal tissue including to the skin overlaying the breast that keeps the breast cosmoses intact. The microbeam spares radiation to its adjacent narrow track of normal tissue that regenerates and fills in the space occupied by the microbeam radiated tack of tissue, in this case the tumor tissue. Hence the tolerance to radiation with microbeam is significantly increased. Hence, single fraction, organ preserving whole breast radiation is feasible even with microfocus X-ray tubes based SMRT. The multiple simultaneous beams from a number of angles that passes through the isocentric tumor increase the dose to the tumor substantially while the beam's path through the rest of the breast can be used for the whole breast radiation. Thus the whole breast preserving radiation therapy with microfocus x-ray tube is made possible.

Generally, a tumor free margin is recommended for effective control of tumor recurrence in the residual breast that is treated by breast preserving surgery. When the tumor margin is free from microscopic tumor, the local recurrence rate within the preserved residual breast is in the range of 2-9% and when the margin is positive, such local recurrence is in the range of 0-27% per several publications (72). This commentary cites most of the past major studies on this subject. The end point for reporting 12 of these major studies ranged 5 years in three, 8 years in two, 10 years in five, 12 years in one and one had only crude rate. None of these 12 major studies cited by Roukos et al have analyzed the local recurrence and the effect of month's long prolonged waiting after the first surgical violation of the tumor bed to complete the diagnosis and the treatment. Addition of radiation after breast preserving surgery reduces the recurrent breast cancer in the ipsilateral treated breast to about 60%. However it has no benefit in improving survival or reducing distant metastasis when it is compared with excision alone (73).

While most of the reports on the status of the resection margin are considered as a determinant factor for increased tumor recurrence in ipsilateral residual breast after breast preserving treatment, there are also reports stating that it is not such a predominant factor for IBT in selected groups of patients. Patients aged 35 and below have increased IBT while patients aged 36 to 55 and older have statistically insignificant risk for IBT when they were also treated with Tamoxifen. These patient groups includes stage I or II breast cancer (74). It is reported that tamoxifen was the most significant factor for reduced incidence of IBTR in patients aged 36 to 55 and older. The high dose rate radiation therapy, 10 Gy/sec to 10,000 Gy/sec and higher would sterilize the cancer stem cells even in breast cancers of patients at younger age of 35 and below.

The accelerated whole breast radiation therapy given in three weeks is as effective as whole breast radiation given in 5 weeks (75). Over 6 years follow up, the local recurrence and the cosmetic outcome was reported as equal for both methods of treatment. However, in general community practice, it is seldom one sees a patient who was treated by breast preservation surgery and whole breast radiation with or without boost radiation to the tumor bed without a great deal of breast deformity. Most often, its cosmetic outcome is very poor. The accelerated partial breast irradiation (APBI) is also reported to have "unexpected late side effects" with breast fibrosis and poor cosmetic outcome (93). In APBI method of partial breast radiation therapy, 385 cGy (3.85 Gy) per fraction is delivered to the tumor bed. Two such treatments a day at 6 hour intervals is given. In 5 days, a total of 10 treatments are given which takes to a total dose of 3,850 cGy (38.5 Gy). This method of APBI is now widely used. In the National Breast and Bowl Project (NSABP) B 39/Radiation Therapy Oncology Group (RTOG) 0413, the APBI is compared with whole breast radiation therapy. Already, over 3,000 patients are entered in this NSABP B39/RTOG 0413 trial on APBI. Its "unexpected late side effects" was reported above and by Hepel et al (76) and Jagsi et. al (77).

There are a number of early stage breast cancer without any palpable tumor but diagnosed per diagnostic or screening mammograms. Most of such patients will undergo the first diagnostic surgical step, namely the stereotactic breast core biopsy. Usually, at the time of stereotactic breast core biopsy, 5-15 core biopsy specimens are taken. It leaves an adequate tissue deficient track at the tumor bed that would allow insertion of an electronic brachytherapy source to the tumor bed. If such electronic brachytherapy could be combined with stereotactic breast core biopsy, it will minimize the breast deformity by minimizing the surgical excision. For a greater percentage of patients with non-palpable, mammographically detected early stage breast cancer, mastectomy is not needed. In addition to the cosmetic outcome by avoiding the biopsies for these patients, there will be a substantial cost savings for these patients. The cost savings per biopsy is on the average of about 4,000 dollars. Per mammographic findings, over 500,000 biopsies are performed per annum in the US. If most of these biopsies could be avoided, there will be a cost savings of over 2 billion dollars. It is in addition to the economical loss from time taken away from work to attend to the treatments. It also spares a patient from psychological distress associated with the protracted treatment and the waiting for the treatment.

The dose rate of the Intrabeam system with 50 kV x-rays from a single source has similar depth dose characteristics at 5 mm depth as for the Xoft single source system but with variations due to different kind of applicators used in these systems. The Xoft single source system's applicator includes a balloon while the Intrabeam system uses spherical applicators of varying sizes, from 1.5 to 5 cm in diameter. The normalized depth dose at 0.5 mm depth for both single beam electronic brachytherapy systems with the applicators are approximately about 10 Gy. In another version of the x-ray source used in this invention, using lower energy radiation source is also described.

Cosmetic Whole Breast Preserving Single Fraction Additive Dose Rate Radiation Therapy without Breast Deforming Surgeries Combined with Tamoxifen for Early Stage Breast Cancer It is shown that intraoperative single fraction radiation therapy with or without whole breast radiation is effective and safe for cure and control for invasive breast cancer (78). Intraoperative single dose, 15 Gy before the surgical biopsy is effective for local tumor control and to maintain good to excellent cosmesis of the breast (66). It will be more effective when such treatment is combined with tamoxifen (74). Single fraction dose of 20 Gy to the breast tumor bed is well tolerated (67). Hence intraoperative single fraction whole breast 20 Gy radiation with a conventional medical accelerator combined with tamoxifen and boost radiation to the tumor bed with 10-15 Gy concomitant boost electron or 30-50 kV low energy photon radiation is as effective as conventional 5 weeks protracted whole breast radiation combined with five to 10 fraction tumor bed boost radiation with 30-50 kV X-rays. If the radiation is given with parallel micro beams, the whole breast and tumor bed radiation dose is increased to over 100 Gy which is well tolerated without many side effects. The rat skin tolerance dose for microbeam is in the range of 5,000 Gy that is 500,000 cGy (68) Rat brain tolerance dose for synchrotron microbeam is in the range of 312 and 625 Gy that is in the range of 31,200 to 62,500 cGy (69). Thus when radiation therapy is rendered with parallel microbeam with broad beam effect at the tumor site, the tolerance dose to the normal issue is extremely high. Hence much higher than the conventional about 50-60 Gy, about 200 to 500 Gy can be administered to the breast and other type of cancers without much toxicity to the normal tissue. It is a very highly curative tumor dose. This intraoperative single fraction radiation therapy is combined with diagnostic stereotactic biopsy that takes little breast tissue and hence causes no obvious breast deformity from such biopsy. Addition of heavy Z-metal containing chemotherapy further makes the tumor cure even higher and the tumor to disappear. Auger and characteristic radiation at the isocentric tumor where the parallel microbeam intersects removes the valley effect of microbeam radiation. Three to six months after single fraction radiation therapy, residual tumor if any at the tumor bed is checked by mammogram, MRI, CT, PET scans and stereotactic needle biopsy. In most cases, there will no residual tumor and the tumor control at 5 and 10 years will be superior to those reported for the conventional 5 weeks duration radiation therapy or the accelerated 3 weeks duration radiation therapy. If there is no residual tumor in the tumor bed, no lumpectomy or mastectomy is needed. This allows full breast preservation with cure from breast cancer for most early stage tumor. Such single fraction, intraoperative radiation therapy to the breast eliminates the about 4 month's duration diagnostic and treatment for such breast cancers. It relives the much personal and social inconvenience and the waiting and prolonged treatment associated anxiety and the economical loss due to loss of working time.

The 10-20 keV Valley-Filling Scatter Radiation and its RBE

When a tissue is radiated, its scatter radiation produces also 10-20 kV range X-rays that is confined within the tumor. It fills in the valley regions in the tumor where all the beams intersect. Such Compton scattering and coherent scattering adds to the formation of a dense bell shaped peak radiation within the tissue that is radiated (79). In addition, the ligand-receptor or antibody bound or implanted higher atomic weight element's interaction with kV-X-ray tuned to the binding energies of the k, l, m, n shell generates 10-20 kV locally absorbing Auger transformation characteristic x-rays. Higher atomic weight iodine tagged ligands bound to the tumor or gold or titanium or similar high z-element nanoparticles implanted into the tumor generates such locally absorbing characteristic X-rays. Alternatively, for Auger transformation-radioimmunotherapy and gene targeted therapy the metallic nanoparticles bound monoclonal antibodies is administered directly into the tumor during the intraoperative radiation therapy. The combined locally absorbing Compton scattering and coherent scattering and the Auger transformation characteristic x-ray radiation have energies in the range of 10-20 kV which have higher RBE (41). They enhance the RBE of the radiation within the isocentric tumor. It contributes to make a higher bell shaped dose distribution within the tumor.

2. The RBE of 10 kV x-ray is reported as 125 times higher than that for the RBE of higher energy x-ray beams (41). The statement that the RBE of 10 kV x-ray as "125 times more effective compared to 50 keV x-ray beam" might be an overstatement or a typographic error, it may be meant as 1.25 times higher. The RBE of 50 keV x-rays relative to $^{192}$Ir photon is about 1.5 (80). The RBE of 10 kV x-rays relative to 200 kV X-rays in the range of 1-10 Gy is reported for MCF-12A human mammary epithelial cells as 1.21 plus-minus 0.03 at 10% survival. (60). In the same study, RBE for induction of formation of micronuclei at dose range of 0.5 to 3.6 Gy was found to be 2.6 plus-minus 0.4 for the fraction of micronucleated cells with micronuclei" and 4.1 plus minus 1.0 "for the number of micronuclei per micronucleated cell" (60). In this study, it was also reported "an increase in RBE with decreasing photon energy down to the mean energy of 7.3 keV" (60). The much increased RBE of 10 kV photons is due to the ionization of low atomic weight soft tissue by low energy, 10 kV photons. The k-shell binding energy of soft tissues is only about 0.5 kV and hence the energy of the characteristic x-ray produced by the incident low energy, 10 kV photons is very low. It is absorbed within the soft tissue that is within the tumor tissue in this case. For higher energy incident photon and higher atomic number tissues like the bone, the characteristic x-ray produced by the incident higher energy photon is high. Hence most of this high energy photon travels far away from the soft tissue. Thus lesser high energy characteristic x-ray is absorbed locally by the soft tissue. Higher the local absorption of the characteristic x-rays, higher is its radiobiological effectiveness. The LET of the low energy, 10 kV photons is also high (80). Hence the higher RBE of the 10 kV x-rays when the soft tissue is exposed to it. When soft tissue is exposed to 50 keV x-ray beam, its RBE is about 1.5 (60). The RBE of $^{192}$Ir and 50 keV x-ray is also reported as about 1.2 (81) The decreased local absorption of characteristic x-ray of higher energy photon ranging from 100 to 150 kV that is generally used for x-ray imaging and CT scans. It is the reason why it does not visualize the soft tissue adequately.

The 10 keV photons will not penetrate the skin sufficiently and hence it is not used to treat deep seated tumors. However, a breast cancer can be exposed to low energy beam produced by the electronic brachytherapy source attached to its applicator and inserted into the tumor directly. The characteristic and Auger electrons' produced in the soft tissue is locally absorbed. Likewise, a 10 keV photon generated by an electronic brachytherapy system when brought closer or inserted into the tumor, the characteristic and auger electron is absorbed within the tumor. It renders higher RBE radiation to the tumor.

The 10 keV photon's dose rate will be lower than that for the higher energy photon like the 50 keV photon. However, it is compensated by the less toxic additive high dose rate radiation from multiple simultaneous beams as in this invention. A set of 4 electronic brachytherapy x-ray tubes implanted horizontally or vertically into a tumor bearing microcalcification region. When four such x-ray source sets are implanted from 4 different angles into the same tumor bearing tracks of microcalcifications, its combined electronic brachytherapy source number is sixteen. They provide sixteen simultaneous beams for additive super-high dose rate electronic brachytherapy. It is a much superior dose rate electronic brachytherapy system than the radiation with a single source like that of Axxent electronic brachytherapy, Xoft single source system with 40-50 kV x-ray source and balloon applicator. Its dose rate is 60 cGys/min at 3 cm (22) and 100 cGys at 1 cm (81) from the source in water. Its isodose distribution pattern at the tip of the source is 34 Gy (81). The depth dose of the 50 kV electronic brachytherapy sources and that of the $^{192}$Ir are very close (81). Furthermore, because of the low local absorption of the characteristic x-ray and lower LET of 40-50 kV x-ray source, from the RBE point of views, the radiation from the 40-50 kV source is mostly wasted radiation to the soft tissue that it is surrounded by than that of the 10 kV radiations. The dose rate of the second electronic brachytherapy system, the Intrabeam system from Carl Zeiss Surgical with 50 kV x-rays from a single source has similar depth dose at 5 mm depth as the Xoft single source system but with variation due to different kind of applicators used in these systems. The Axxent electronic brachytherapy, Xoft single source system's applicator includes a balloon system while the electronic brachytherapy system, the Intrabeam system from Carl Zeiss Surgical uses spherical applicators of varying sizes, from 1.5 to 5 cm diameter. The normalized dose at 0.5 mm depth for the single beam electronic brachytherapy system with an average applicator diameter of 45 mm is about 10 Gy (81). 10 kV X-ray's depth doses is 2-5 mm. It s absorbed within the protective cover of the system which is made of biocompatible polyetherimide (C37H24O6N2). However, without any added applicator protective cover, this 10 kV X-ray is locally absorbed. Without the applicators like those used with Xoft and Intrabeam sources, the dose rate of the 10 kV x-ray source at 0.5 cm is as high as that for the Xoft and Intrabeam 50 kV sources with the applicators. The 10 kV X-ray's dose rate and the depth dose is further improved by the additive dose rate of multiple simultaneous beams as in this invention. In addition, by having multiple simultaneous beam sources, say one set of four and each being placed at four different treatment spots and multiple such four arrays of 10 kV sources, say 16 of them implanted into the tumor bearing site gives super high additive dose rate that also improves the depth dose. It further improves the RBE. In this case, there are no interrupted treatment of the tumor as when the tumor is treated by a single spot at a time and then moving the source to the second dwell spot and treating the second spot and repeating the same to treat a third, fourth, a fifth spots and so on to complete the treatment of the entire tumor by Xoft and Intrabeam systems. This method of interrupted treatment as moving the source from one treatment spot to another (82) and treating one treatment spot one at a time with Xoft and Intrabeam electronic brachytherapy systems (22) is analog with the interrupted daily fractionated external beam radiation therapy where field by field are treated. It is as treating one field from a given angle and then rotating the accelerator to another angle to treat a second filed from that angle and repeating the same to treat the second, third, fourth, fifth filed and so on. The step and shoot methods of tomotherapy is also an interrupted method of treatment. Hence its RBE is also very poor. It is discussed in the issued and pending patent applications of this inventor (1-10).

Based upon the treatment planning, the dwell time at each dwell points representing the tumor bed and microcalcification is only a few seconds. Based upon the dose distribution analysis for individual patient's treatment, separate dwell times even may not be needed. Thus the entire treatment is completed within seconds. Because of the much improved RBE of the 10 keV photons itself and the high additive dose rate's contribution that further improves the RBE, the total dose needed to sterilize a tumor is decreased. Still a higher total dose could be used to treat tumor with such a setup brachytherapy with additive high dose rate. With this system, only a single fraction radiation is needed to sterilize a tumor.

Lethal and Sublethal Damage Repair Inhibition with Additive, Close to 200-500 Gy/Sec Dose Rate Microbeams that Mimics Synchrotron Radiation The radiobiological effectiveness of AFSRT is illustrated in the following quoted in the following example. When a given radiation dose is administered as two split fractions to Chinese hamster cells and each such split dose fractionated radiation is separated by a time interval of 30 min, there is almost twice the number of surviving fraction of cells as compared to when the split-dose time interval is only a few seconds (83) This increase in cell survival is due to sublethal damage repair. By treating a tumor with multiple simultaneous beams in conformity with the tumor and each of the multiple beams' intensity is modulated to suit the tumor volume at each segment of the tumor as intraoperative intensity modulated radiation therapy with high additive dose rate from all the simultaneous beams improves low energy X-rays RBE further. It inhibits most of the photon and electron radiation associated lethal and sublethal damage repair. The RBE of 10 kV x-ray is between 1.2 and even 4 when chromosomal changes are also counted (60). It facilitates treating a tumor with RBE that is equal to or superior to high LET radiation like that for neutron (1.5) or spread out high energy ions like carbon ion (2.2) (82).

Iodinated Steroids and Iodine K, L, M, N Shell Characteristic Photon and Auger Electron for Imaging and Radiation Therapy The ability to tune the monochromatic high-flux short-pulse x-rays to the binding energy of the K shell is used to detect various elements in the body. Elements that have great affinity binding to tissue thus can be used such K-shell electron radiation for radiation therapy and imaging. A number of steroid molecules could be directly iodinated (84). It includes estrogen, testosterone, cortisone and a number of other steroids (84). Hence, iodinated estrogen and testosterone (84) could be used for tumor specific K-shell characteristic photon and electron radiation therapy and imaging.

Contact Intraoperative Radiation Therapy and its Enhanced K-Shell Characteristic Photon and Auger Resonant Electron Radiation The ligand-receptor or antibody bound or implanted higher atomic weight elements and tuned monochromatic X-ray when external or interstitial x-ray beams of 30-50 kV or higher is used, the energy of the beam is tuned to the binding energies of the k, l, m, n shell. It facilitates locally absorbing Auger transformation characteristic x-ray radiation. Higher atomic weight iodine tagged ligands or implanted gold or titanium or similar high z-element nanoparticles are radiated with monochromatic x-ray that is tuned to the k-shell binding energies of such high Z-elements. For Auger transformation-radioimmunotherapy and gene targeted therapy the metallic nano particle bound monoclonal antibodies that are made as metalloprotein is administered directly into the tumor during the intraoperative radiation therapy. The additive very high dose rate from multiple simultaneous monochromatic beams has a steeper cell survival curve with high $\alpha/\beta$ ratio and sublethal damage repair inhibition and hence its improved RBE. Hence the effectiveness of tumor specific radioimmunotherapy and gene targeted therapy is much improved. The interaction of tuned monochromatic 30-50 keV x-ray that is used for electronic brachytherapy with iodine bound antibodies or ligands like steroids will elicit its k-shell specific Auger emission. It radiates the tumor cell specifically. It induces increased tumor cell's single and double stand DNA breaks leading to tumor specific radiation and tumor specific cell kill. The pencil beam characteristics of monochromatic x-ray renders sufficient penetration of the beam to treat a deep seated tumor. Dose is boosted with interstitial x-ray tube implants or with megavoltage beam from an accelerator if the system is a combined with such system. When radiation is given only with monochromatic x-ray, the field shaping collimation is with simply shaped lead cutouts. It makes the treatment much easier.

Tumor Specific K-Shell Electron Radiation Therapy and Imaging of Estrogen Receptor Positive and Negative Breast and Testosterone Receptor Positive and Negative Prostate Cancer In the U.S. Pat. No. 4,321,208, "Preparation of Directly Iodinated Steroid Hormones and Related Compounds" by this inventor, Velayudhan Sahadevan described the directly iodinated estrogen binding to both estrogen receptor of the tumor tissue and to estrogen antiserum (84). There is estrogen receptor positive and negative breast cancer. Likewise, there is androgen receptor positive and negative prostate cancer. Estrogen binds to estrogen receptor in the breast cancer. Testosterone binds to testosterone receptor in prostate cancer.

Both estrogen receptor positive and negative tumors contain estrogen. While developing the estrogen receptor testing on breast tumors in the mid seventeen as a test for elective treatment of patients with breast cancer, this inventor also tested estrogen contents of both estrogen receptor positive and negative tumors (84). The estrogen receptor assay in tumor cytosol was performed by sucrose gradient ultracentrifugation. Tumor cytosol was prepared from the ground tumor specimen. The estrogen content in such cytosol was determined by radioimmunoassay. Both the estrogen positive and negative tumors were found to have measurable amount of estrogen. From this study, it is evident that both estrogen receptor positive and negative tumors bind to estrogen. However estrogen receptor negative tumors may not have the ability to transport estrogen into the cell interior hence its poor metabolic utilization. However, many estrogen receptor negative tumors could transform into estrogen receptor positive tumors (86).

Like the estrogen receptor positive and negative breast cancer, testosterone receptor positive prostate cancer binds to testosterone. Hence testosterone-androgen ablation is one of the major treatment modality for prostate cancer. Like the transformation of the estrogen receptor negative tumor into estrogen receptor positive tumor (86), testosterone receptor negative tumor might transform into androgen receptor positive tumor. Prostate cancer also contains estrogen receptor. Hence treatment of prostate cancer with diethyl stilbesterol (DES), an estrogenic compound or estrogen itself was a common practice in the past.

Directly iodinated estrogen and androgen offers a unique method of iodinated estrogen enhanced, tissue specific, radiation therapy by excitation of iodine bound to estrogen which binds to estrogen receptor positive breast and prostate cancer. Other iodinated steroid molecules like iodinated testosterone bound to testosterone receptor positive prostate cancer offers similar tissue specific receptor bound iodine for iodine's K-shell excitation characteristic photon and Auger resonant electron radiation therapy. Iodinated cortisone (84) is another such example. The iodinated steroid molecule is administrated either intravenously or it is implanted into the tumor as adsorbed on to charcoal nano particle dust. Such implanting of the nano particle charcoal bound iodinated steroid molecule has the advantage of inhibiting the metabolic dissociation of iodine from the steroid and thus preventing dissemination of iodine from the implant site in the tumor.

Like the naturally occurring estrogen, the iodinated estrogen also binds to estrogen receptor competitively with estrogen DES and other estrogen receptor binding anti-estrogen like molecules like tamoxifen citrate. Hence in estrogen receptor positive tumors, the iodinated estrogen will overcome the cell membrane blocks and move into the cell while in estrogen receptor negative tumors, it will be blocked at cell membrane level. Still both estrogen receptor positive and negative tumors will contain iodinated estrogen. In estrogen receptor positive tumors, first it binds to cell membrane. The cell membrane bound iodinated estrogen-estrogen receptor is then transported into the cell. In estrogen receptor negative tumors, it is mostly bound to cell membrane and might not be transported into the cell. Synergistic activation of functional estrogen receptor (ER)-a by DNA methyltransferase and histone deacetylase inhibition in human ER-α-negative breast cancer cells renders a substantial percentage of them as estrogen receptor positive cells (86). Thus the blockage of estrogen transport into estrogen negative tumor cell can be overcome. It facilitates tumor specific K-shell characteristic photon and Auger electron radiation therapy and imaging of estrogen receptor negative tumors as well. The same is applicable to estrogen receptor positive and negative prostate cancer. They are just examples of tumor specific K-shell characteristic photon and Auger electron radiation therapy and imaging. High affinity iodinated cortisone binding tumors are treated similarly with k, l, m, n shell characteristic photon and Auger electron. There are many tumors with high affinity binding to nano particle elements. Such tissue specific high affinity binding to nano particle elements are used for K-shell electron radiation therapy and imaging.

Low-Cost Advanced Intraoperative Radiation Therapy and Global Oncology

The method of multiple simultaneous intraoperative radiation therapy with miniature orthovoltage radiation with improved RBE and less toxicity is relatively simpler. It is very much cost efficient than the present high investment and labor intensive conformal radiation therapy (ILI-CRT). The present intensity modulated radiation therapy (IMRT) is such an example. On a global basis, very few can afford the present IMRT or even a simple accelerator based radiation therapy system in lieu of now obsolete cobalt machines. Many global medical institutions have advanced surgical capabilities but cannot afford the investment for the present-day medical accelerators and its accessories and needed personnel to operate them. Present-day cancer drugs are very expensive even for economically advanced countries. They are unaffordable to most patients from economically disadvantaged countries. In those places, most often the diagnosis of cancer is made at its advanced late stages. In such circumstances, radiation therapy is the only practical treatment for most of those patients. Hence, this invention is also aimed to facilitate affordable global radiation therapy and cancer treatment.

The intraoperative multiple simultaneous beam radiation therapy system of this invention is a low cost one. The intraoperative radiation avoids the usual X-ray tube based radiation therapy's excessive skin dose and normal tissue damage. Using the microfocus miniature thermionic X-ray tubes or the CNT based field emission X-ray tubes instead of the complex and expensive accelerator system makes this system very inexpensive. Its additive super high dose rate that can be brought close to synchrotron radiation makes this system radiobiologically superior than the present single beam accelerator based daily subfractionated Radiation therapy system. Its additive super high dose rate of 10 Gy/sec to 10,000 Gy/sec and higher brings its RBE closer to that of high LET radiation. Thus, at penny's cost as compared to other alternatives methods of advanced cancer treatment, this form of low-cost but more advanced cancer treatment is brought to home to all those who needs it.

Cellular Radiation Therapy for Benign Diseases with Parallel Microbeams from CNT-FE X-Ray Tubes, CNT-FE Accelerators and CNT-FEI X-Ray Tubes The U.S. Pat. No. 7,194,063 (68) and U.S. Pat. No. 7,746, 979 (55) by Dilmanian et al teaches a method of microbeam radiation therapy to assist diseased but non-malignant tissue to recover by selectively radiating non-mitotic cells. This method of treatment is suggested to stimulate regeneration of nerve tissue and thus to treat injured spinal cord and brain. It is also recommended to treat chronic illness like the multiple sclerosis, demyelinating disorders, Parkinson's disease, macular degeneration, fibrosis of the lung, liver, and kidney, to stimulate revascularization of bone and to treat atrial fibrillation etc. In these inventions, synchrotron radiation or bremsstrahlung radiation from x-ray tubes is collimated as microbeams. At any one time, single beam radiation from a given angle is used to treat the injured tissue. Because of high degree of filtration of the x-ray when X-ray tube based SMRT, the dose rate of the X-ray microbeam is extremely low. As described in U.S. Pat. No. 7,746,979, at 200 cGy/min dose rate, it will take 50 min to administer 100 Gy in a single session. Microbeam radiation to treat only selected cells in a target requires high precision patient immobilization. To keep a patient as immobilized and without physiologic organ movement for 50 minutes is not an achievable goal even if the patient is kept under anesthesia. The treatment time is shortened to about 30 min with simultaneous beams from multiple orthovoltage X-ray tubes in U.S. Pat. No. 7,643,610 by Dilimanian (87) The life sustaining respiratory and cardiac movements of a patient cannot be stopped for such a prolonged time. Likewise, in the abdomen, the peristalsis of the intestine will continue without interruption during such prolonged radiation therapy time.

U.S. Pat. No. 5,339,347 (88) teaches a method of microbeam radiation therapy for cancer that minimizes the radiation dose to normal tissue. It also suffers the difficulties associated with prolonged treatment time. The main them in these patents are treating a tumor with synchrotron produced X-rays which has vey high dose rate, 20,000 Gy/sec. Unfortunately, it is compared with radiobiologically very ineffective 0.17 to 0.83 Gy/sec X-ray tube based radiation in U.S. Pat. No. 7,643,610—by Dilimanian (87). If on the other hand, multiple simultaneous X-ray tube based contact SMRT is used as in this invention, its dose rate is brought to 10 Gy to 10,000 and over. Its radiobiology is much superior and the treatment time lasts only a fraction of a second. For the treatment of benign disorders, the dose rate of about 10 Gy/sec might be sufficient.

Cellular Radiation Therapy for Parkinson's Disease with Parallel Microbeams from CNT-FE X-Ray Tubes, CNT-FE Accelerators and CNT-FEI X-Ray Tubes As stated before, U.S. Pat. No. 7,194,063 (68) and U.S. Pat. No. 7,746,979 (55) by Dilmanian et at teaches a method of microbeam radiation therapy to assist diseased but non-malignant tissue to recover by selectively radiating non-mitotic cells. This method of treatment is suggested to stimulate regeneration of nerve tissue and thus to treat injured spinal cord and brain. It is also recommended to treat other demyelinating diseases like the multiple sclerosis.

A number of surgical procedures are performed to treat the Parkinson's disease. They include surgical treatment, pallidotomy and thalamotomy and the non-ablative chronic deep brain stimulation. Pallidectomy and thalamotomy reduces the parkinsonian symptoms. Pallidotomy involves placement of placement of a small thermolytic lesion in the posteroventral portion of the internal segment of the globus pallidus. In thalamotomy a thermolytic lesion in the ventral intermediate nucleus of the thalamus is placed. Like pallidotomy and thalamotomy, a miniaturized CNT x-ray tube could be placed in globus pallidus and in thalamus for either ablative treatment or for stimulation of the basal ganglia that is described below. Such stimulative treatment might help the regeneration normal nerve tissue as stated in U.S. Pat. No. 7,194,063 (68) and U.S. Pat. No. 7,746,979 (55) by Dilmanian et at but in this invention such nerve cell regeneration is induced with interstitial implant of innovative miniature CNT X-ray tubes that produce elective number of multiple simultaneous microbeams than with external microbeams from 100 to 250 kV X-rays. The radiobiologically more effective 10 kV X-rays are locally absorbed. It is more stimulating for healthy nerve cell to migrate to the diseased site that would replace the diseased cells.

Treatments other than surgery also aimed at neurogeneration to restore the function of basal ganglia include intrastriatal transplantation of fetal mesencephalic tissue and transfusion of neurotrophic factors. Patients who do not respond to medical treatments like treating with dopaminergic drug levodopa are considered for surgical treatments. The loss of dopaminergic neurons in substantia nigra pars compacta causes abnormal nerve stimulation in subthalamic nucleus globus pallidus internus and in substantia negra pars reticulata. Abnormal activity in these subthalamic nucleuses will cause abnormal stimulus in thalamus which exerts control over the motor cortex resulting in suppression of thalamocortical activity which leads to the expression of Parkinson's disease.

Deep brain stimulation (DBS) of the basal ganglia with high frequency, 100 Hz is an alternative treatment to surgical ablation of above basal ganglia. It can control the disease like the ablative process resulting in control of the symptoms of the Parkinson's disease. In this process, a multicontact stimulating lead is implanted into a specific basal ganglia and it is connected to a radiotelemetry programmable impulse generator under the clavicle. The physiological mechanism of how this DBS system works is not fully understood.

This deep brain stimulation, DBS might have similarities to stimulated regeneration of nerve tissue by selectively radiating non-mitotic cells with microbeam (68, 55) as suggested in U.S. Pat. No. 7,194,063 (68) and U.S. Pat. No. 7,746,979 (55) by Dilmanian et al. It is thought that such microbeam radiation stimulates regeneration of the nerve tissue in injured brain and spinal cord and inhibits the proliferation of astrocytes that stimulates gliosis. Other involved pathophysiological mechanisms are also postulated. It is postulated that microbeam radiation is also as beneficial for the treatment of Parkinson's disease. The suggested method of treatment is treating the diseased or injured site at least with two parallel, spatially distinct microbeams to a dose of 30 to 500 Gy, which is about 3,000 to 50,000 cGy. The recommended method of treating a lesion is described as treating from a number of angle variable intersecting microbeam arrays (AVIMA) delivered in different sessions where each session is separated by a time interval of 12 hours to 7 days. This method of treatment is called as AVMIA dose fractionation. Three to thirty fractions are used to treat a patient. To vary the angel of treatment either the radiation source or the patient is rotated. Either bremsstrahlung radiation or synchrotron radiation is used to treat a patient. Two parallel, spatially different 100 to 250 keV microbeams of 0.1 to 1 mm thickness when it is a bremsstrahlung radiation and 20 to 100 µm thickness when it is a synchrotron beam is used to treat a lesion at any one session from a given angel. It may be combined with stem cell treatment. Therapeutic treatment with such microbeam is also described in this invention. The dose rate is 200 cGy/min, and it takes 50 min to administer a dose of 100 cGy.

Such stimulative treatment might help the regeneration normal nerve tissue as stated in U.S. Pat. No. 7,194,063 (68) and U.S. Pat. No. 7,746,979 (55) by Dilmanian et al but in this invention such nerve cell regeneration is induced with interstitial implant of innovative miniature CNT X-ray tubes that produce elective number of multiple simultaneous microbeams than with external microbeams from 100 to 250 kV X-rays. The radiobiologically more effective 10 kV X-rays are locally absorbed. It is more stimulating for healthy nerve cell to migrate to the diseased site that would replace the diseased cells.

The methods of microbeam radiation therapy with external 100-250 keV X-rays as in U.S. Pat. No. 7,194,063 (68) and U.S. Pat. No. 7,746,979 (55) by Dilmanian et al is difficult to implement. Only a very small percentage of the dose will reach the thalamus and globus palladium as they are deep seated structures in the brain. Its skin dose and the dose to other parts of the brain through which the micro beams travels would be very high. The recommended dose is 30 to 500 Gy, that is 3,000 to 50,000 cGy. If about 60% of the beam reaches the deep seated basal ganglia, the skin, skull and normal brain dose would be in the range of 5,000 to 83,000 cGy per fraction of the 20-30 treatments given in at intervals ranging from 12 hours to one week (55). The time taken to administer the middle of the road dose of 100 Gy to the deep seated basal ganglia at 2 Gy/min dose rate and 60% depth dose is 83 min. It would be impossible to keep a patient immobilized and still during the recommended 20 to 100 µm and or 1 to 2 mm wide parallel beams. On the other hand, the interstitial implant of innovative miniature CNT X-ray tubes that produce elective number of multiple simultaneous microbeams can treat the lesion in a few seconds or minutes than treating with external microbeams from 100 to 250 kV X-rays. Again, the radiobiologically more effective 10 kV X-rays are locally absorbed. It does not expose the normal tissue as the 100-250 keV x-rays used in U.S. Pat. No. 7,194,063 (68) and U.S. Pat. No. 7,746, 979 (55) by Dilmanian et al. It is more stimulating for healthy nerve cell to migrate to the diseased site that would replace the diseased cells.

Phase Contrast Imaging and MRI Guided Radiation Therapy

Computer assisted radiation therapy planning systems incorporates software tools for automatic contouring of tissue structures from absorption radiology's images. However, the absorption radiology imaging systems are incapable of soft tissue imaging; they are incapable of gathering detailed information on the tumor tissue since most of the tumor is made of soft tissue. Hence, to overcome this deficiency, the GTV, CTV, PTV and other important soft tissue structures are defined manually. Obviously, it is not very accurate.

Phase contrast imaging on the other hand is much different from the absorptive radiology. It is based upon the variations in phase structure that is made visible by phase shift of the x-ray photons. Minimal deviation from the initial path of the incident x-ray beam occurs as it interacts with the atom of the object that it radiates like when it pass through the soft tissue. Phase shift, also referred to as small angle scattering is a deflection of the incident beam within the object that it radiates. When the intensity of the deflection is large enough, the deflected x-ray is shifted to a different place, like to an adjacent pixel in the detector. Such phase contrast imaging is better suited to detect microscopic details in soft tissue. Any soft tissue structures that could produce deflection and from the incident photon's initial direction and its velocity is suitable for phase contrast imaging. Early soft tissue changes with increasing density such as in a very early developing cancer, inflammation associated changes in tissue all could induce measurable deflection of the incident monochromatic x-ray. The US patent application 20010038680 by Charles J Davidson, (89) and U.S. patent application Ser. No. 12/799, 949 by Sahadevan (10) teaches the principles of phase contrast imaging and small angle phase shift of an incident monochromatic narrow beam in detail. It is referred here in its entirety. Phase contrast imaging is more suitable for soft tissue imaging that is composed of low molecular weight elements like carbon, oxygen, hydrogen, nitrogen etc. An array of low energy monochromatic X-ray microbeam that is used in this invention for intraoperative radiation therapy is highly suitable for phase contrast image guided radiation therapy. Similar phase contrast image guided radiation therapy is described in the patenet application by this inventor (10).

More image details, especially the microscopic details is imaged by phase contrast imaging with low energy, longer wave length beams than it is possible with high energy, shorter wave length beams. Thus the 10 to 50 kV beams that is also used for intraoperative radiation therapy in this invention is capable of soft tissue imaging with its microscopic details. Phase contrast imaging is also used for clinical investigations that involve protein analysis, X-ray diffraction (XRD), single wavelength anomalous diffraction (SAD) phasing for protein analysis.

BRIEF SUMMARY OF THE INVENTION

This invention is on low-cost but advanced radiation therapy with multiple simultaneous X-ray microbeams. The microfocus X-ray sources are placed as either external or interstitial or combined with external and interstitial short duration implants. The duration of the radiation exposure to the treating tissue is only for a fraction of a second. Miniaturized microfocus X-ray tubes including CNT-based X-ray tubes and CNT based accelerators are used for radiation therapy and research. Multiple microfocus X-ray tubes or electronic brachytherapy x-ray tubes or carbon nanotube based x-ray tubes are brought close to surgically exposed tumor or to an organ which does not need such surgical exposure to for contact radiation therapy. Multiple simultaneous beams are focused onto an isocentric tumor for additive high dose rate radiation therapy. Multiple electronic brachytherapy X-ray tubes are also used for simultaneous multiple port minimally invasive breast cancer treatment and for accelerated partial breast irradiation (APBI). Carbon nanotube field emission X-ray tubes (CNT-FE X-ray Tubes) with metal oxide semiconductor transistor (MOSFET)-microelectromechanical systems (MEME) technology are used to construct both miniaturized X-ray tubes. New 0.6 mm2 MOSFET with 0.8 mm out line and 0.357 mm height facilitates construction of even more smaller CNT based X-ray tubes than the previous very small such X-ray tubes. Its high dose rate that is closer to synchrotron radiation is achieved by combined isocentric dose rate of all beams at the isocenter and not by increasing the machine dose rate to very high that would cause major normal tissue toxicity. Orthogonal microbeams with 25-75 µm width and 200-400 µm spacing makes the peak and valley doses of the microbeam very distinct with 100% dose at the peak and about 10% dose at the valley from scatted and characteristic radiation. The orthogonal microbeams intersect at the isocentric tumor where the characteristic scattered radiation fills in the radiation that gives homogenous radiation at the isocenter. The combination with monochromatic microbeam based imaging and radiation therapy further reduces normal tissue toxicity. It is also combined with 10-20 kV characteristic auger transformation radiation from heavy elements that are implanted, injected or bound to tissue by high affinity binding by means of tissue specific receptors. The monochromatic beam's energy is tuned to the k, l, m, n shell binding energies of the tissue bound heavy atom nanoparticles. Such tissue specific radiation elicits the tumor specific radiation therapy. Radiation therapy is also rendered with external or interstitial monochromatic microbeams of 5 to 75 µm, preferably from 25 to 50 µm widths and close to parallel elongated beams. Such narrow width elongated monochromatic beams are used for treatment of both benign and malignant diseases and research. Its additive dose peak at the isocenter and the relatively very low dose at beam entry due to dose being distributed among a number of simultaneous beams from multiple ports and the sudden dose fall past the isocenter makes the dose distribution at the isocentric tumor very unique. Higher atomic weight iodine tagged ligands bound to the tumor or those that are implanted into the tumor such as gold or titanium or similar high z-element nanoparticles facilitates such Auger transformation radiation. Alternatively, for Auger transformation-radioimmunotherapy and gene targeted therapy the metallic nano particle bound monoclonal antibodies is administered directly into the tumor during the intraoperative radiation therapy. These combined locally absorbing Compton scattering and coherent scattering and the Auger transformation characteristic x-ray radiation have energies in the range of 10-20 kV. They enhance the RBE of the radiation within the isocentric tumor. It also contributes to make a much higher bell shaped dose distribution within the tumor that creates a "Brag Peak" like dose distribution. The low-voltage, 10-20 kV X-ray's RBE of 1.2 to 4 (60), the additive high dose rate associated improved RBE and eliminating the tumor hypoxia with oxygen that is administered directly into the tumor all brings the RBE of such radiation to a higher level like that of neutron, α-particles and heavy ions like the carbon particles. Combined with phase contrast imaging of soft tissue tumors, its capabilities for biological and cancer research, it offers a unique quality radiation therapy machine. This low-cost photon radiation therapy machine is an advanced affordable high quality system. It also facilitates minimally invasive and least toxic and organ preserving cancer treatment. The start up cost to this system is further reduced by step by step addition of its capabilities like the CT, MRI, PET and the phase contrast imaging. When MV beam combined radiation therapy is needed, a single megavoltage medical accelerator is combined with external monochromatic microbeam X-ray or with contact beams for boost radiation.

Monochromatic microbeam radiation to regenerate acutely injured and chronically diseased organs including nerve tissue opens a wide spectrum for radiation therapy including non-malignant disorders like the Parkinson's disease, focal seizure disorder, vascular malformation, cardiac arrhythmia and similar disorders.

BRIEF DESCRIPTION OF THE DRAWINGS

FIG. 2 is a detailed illustration of the basic structures of a CNT based single set, 10 simultaneous converging beams X-ray tube

FIG. 5 Left half of coplanar and non-coplanar transverse, lateral sagital and cranio-caudal-coronal half circle gantry with X-ray tubes FIG. 6 Right half of coplanar and non-coplanar transverse, lateral sagital and cranio-caudal-coronal half circle gantry with X-ray tubes FIG. 7A Latched right and left half of coplanar and non-coplanar transverse, lateral sagital and cranio-caudal-coronal half circle gantry with X-ray tubes FIG. 7B illustrates the intraoperative multiple simultaneous beam radiation therapy to a tumor with multiple miniature thermionic X-ray tubes.

FIG. 7C illustrates intraoperative radiation to a tumor as shown in FIG. 7B but with CNT based-X-ray parallel microbeam.

FIGS. 7D and 7E shows four sets of CNT based micro-accelerators 281 and their simultaneous 10 parallel microbeams 357 radiating a surgically exposed tumor.

FIG. 8 illustrates four sets of CNT based X-ray tubes all arranged within a circle and each X-ray tube having 10 parallel microbeams, from 0, 90, 180 and 270° angles that renders up to 40 simultaneous parallel microbeams

FIG. 11 is an illustration of eight units, 10 beams each; external CNT based field emission accelerator based combined 80 microbeams radiation therapy system with all the beams converging at the isocenter.

FIG. 12 a single 10 beam CNT based electron accelerator with 10 parallel microbeams for deep interstitial implant is shown.

FIG. 14A illustrates selectively switched parallel opposing 6 simultaneous beams from four sets of miniaturized CNT based 10 microbeams micro-accelerators that covers the planning tumor volume but sparing of the isocentric region where no tumor is located.

FIG. 15C-1 shows a single micro-X-ray tube assembly for implant.

15C-2 illustrates an early stage breast cancer treatment with a single simultaneous four microbeam electronic brachytherapy system FIG. 15D illustrates an early stage breast cancer treatment with four separate simultaneous four microbeam electronic brachytherapy systems

FIG. 25 is a schematic illustration of the Brag-peak like high additive biological dose rate of simultaneous beams that is further enhanced with Auger transformation characteristic radiation which renders intensity modulated photon radiation therapy with improved radiobiologic effectiveness and its comparison with a single beam's dose rate that gradually falls off after the $D_{max}$ dose rate FIG. 26 is a schematic illustration of the Brag-peak like high additive biological dose rate of simultaneous beams that renders intensity modulated photon radiation therapy with improved radiobiologic effectiveness and its comparison with charged particle beam's Brag-peak and its spread out Brag-peak FIG. 27A

REFERENCE NUMERALS

Figure 1:
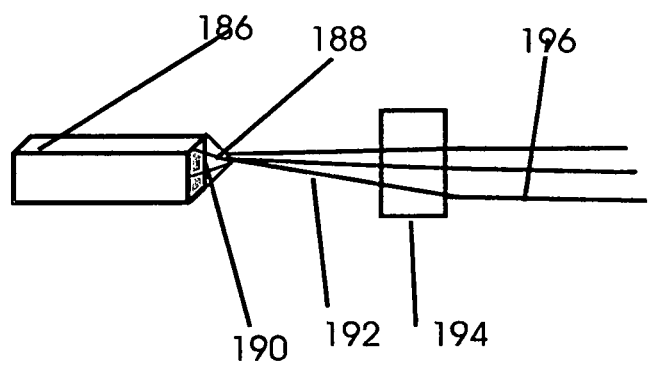
FIG. 1 illustrates a commercially available micro focus x-ray tube that is equipped with analyzer crystal and micro beam collimator that filters the bremsstrahlung polychromatic x-ray into monochromatic x-rays.

186. Micro focus x-ray tube
188 Polychromatic beams
190 Analyzer crystals
192 X-ray after analyzer crystal
194. Microbeam collimator
196 Monochromatic X-ray beams
198 Coplanar plane X-ray source
200 Non-coplanar plane X-ray source
202 cut circular transverse plane gantry
204 cut circular coronal plane gantry
206 Circular sagital lateral plane gantry 208 Gantry segments locking screw
210 gantry-table-rail connector
212 Surgical table with rails
214 Distance and X-ray source adjusting rod
216 Locking screw for X-ray source and distance adjusting rod
218 Gantry-table-rail connector locking screw
220 Gantry-table-rail connector clamps
234 Microfocus X-ray sources
236. Collimator
238 Image processing detectors
240 Detector holding ring
242 Signal processing system
244 Isocenter
246 Exiting monochromatic beams
248 Flat panel detectors
252 Megavoltage medical accelerator
254 Micro focus x-ray holding ring with arced collimator
256 Megavoltage beam
258 Simultaneous beams 1 from 0-degree
260 Single beam's 70% depth dose rate
262 Simultaneous beams 2 from 90-degree
264 Simultaneous beams 3 from 180-degree
266 Simultaneous beams 4 from 270-degree
268 Four beams Additive dose rate
270 Auger transformation characteristic radiations
272 Combined Brag-peak like dose peak
274 Percent depth dose of a mono chromatic x-ray with dose peak at $D_{max}$
276 Monochromatic charged particle beam's Brag-peak
278 Schematic spread out Brag Peak of carbon ion beam
280 Comparative Brag-peak like dose increase of four simultaneous beams
281 CNT based micro-accelerator
282 MOSEFT
283 -Magnet lifting piston
284 MEMS based CNTs holding conductive substrate
285-1 CNT based field emission cathode
285-2 Magnet lifting piston
286 Carbon nanotubes (CNT)
287 Focusing electrode
288 CNT based field emission cathode's electron beam
290 Gate electrodes
292 Insulator
294 MEMS based power supply
296 Electron guide
298 Transmission anodes
300 X-ray beams
302 Vacuum chamber
304 Water cooler with water inlet and outlets
306 Water inlets
308 Water outlets
310 System insulator
312 parallel X-ray microbeams X-ray tube
314 Parallel microbeams X-ray tube with 10 beams from 0°
316 Parallel microbeams X-ray tube with 10 beams from 90°
318 Parallel microbeams X-ray tube with 10 beams from 180°
320 Parallel microbeams X-ray tube with 10 beams from 270°
322 Cross firing parallel microbeams from 0 and 180 and 90 and 270 degrees at the center
324 CNT based parallel X-ray microbeam
325 CNT based X-ray tube
326 Accelerating electrodes-1
328 Accelerating electrodes-2
330 Accelerating electrodes-3
332 Accelerating electrodes-4
333 Isocenter
334 Converging multiple beams at the isocenter
335 CNT based X-ray tube with converging focused 10 beams
340 CNT-based 10 microbeams micro-accelerator
341 Selectively switched parallel opposing 6 simultaneous beams
342 10 simultaneous parallel microbeams
343 Beam shaping collimators
344 CNT field emission cathodes based 10-beam interstitial implants
345 Central radiation field generated by 10 cross firing parallel opposed parallel beams
346 Gross tumor volumes (GTV)
347 Isocentric region spared from radiation
348 Planning tumor volume (PTV)
349 Parallel opposing microbeams
350 Early stage breast cancer with microcalcifications
352 Ductal microcalcifications
353 Breast
354 Breast cancer
355 Nipple
356 CNT based miniature interstitial implant with 10 parallel microbeams
357 Simultaneous 10 parallel microbeam
358 Simultaneous four microbeam electronic brachytherapy system
359A Electronic brachytherapy microbeam peak dose
359B Electronic brachytherapy microbeam valley dose
360 Stereotactic core biopsy systems
361 a patient
362 Stereotactic breast core biopsy system's table
363 Stereotactic system's table
364 PET-CT stereotactic breast core biopsy system
366 Biopsy position
368 CNT based 3 sets, 30 parallel microbeams breast implant
370 electronic brachytherapy X-ray tube
372 Electrical and cooling water inlets
374 X-ray tube holding ring with cooling running water
376 Water outlet
378 X-ray tube and electrical accessories holding rings
380 Broad beam
382 Tumor
384 CNT based X-ray tube
386 Single micro-X-ray tube assemblies for implant
388 Micro-X-ray tube filament cathode
390 Micro-X-ray tube anode
392 Cathode lead cable
394 Anode lead cable
396 Vacuumed glass tube
398 Window
300 Vacuumed tube and anode and cathode holding glass container
302 Water inlet
304 Water outlet

DESCRIPTION OF THE PREFERRED EMBODIMENTS

FIG. 1 illustrates a commercially available micro focus x-ray tube 186 that is equipped with analyzer crystal 190 that filters the bremsstrahlung polychromatic x-ray beam 188 to mostly monochromatic. These commercially available x-ray tubes are equipped with adjustable focal spots ranging from as low as 5 to 50 μm. The 5 μm sized focal spot is very close to the laser produced x-ray's focal spot. They are available with targets ranging from chromium, copper, molybdenum, tungsten etc. The fully packaged commercial tubes have remote control and software controlled operational capabilities. They meet all the radiation safety precautions including instructions and warnings signs on safe operation that is displayed on its display panel.

Figure 15A:
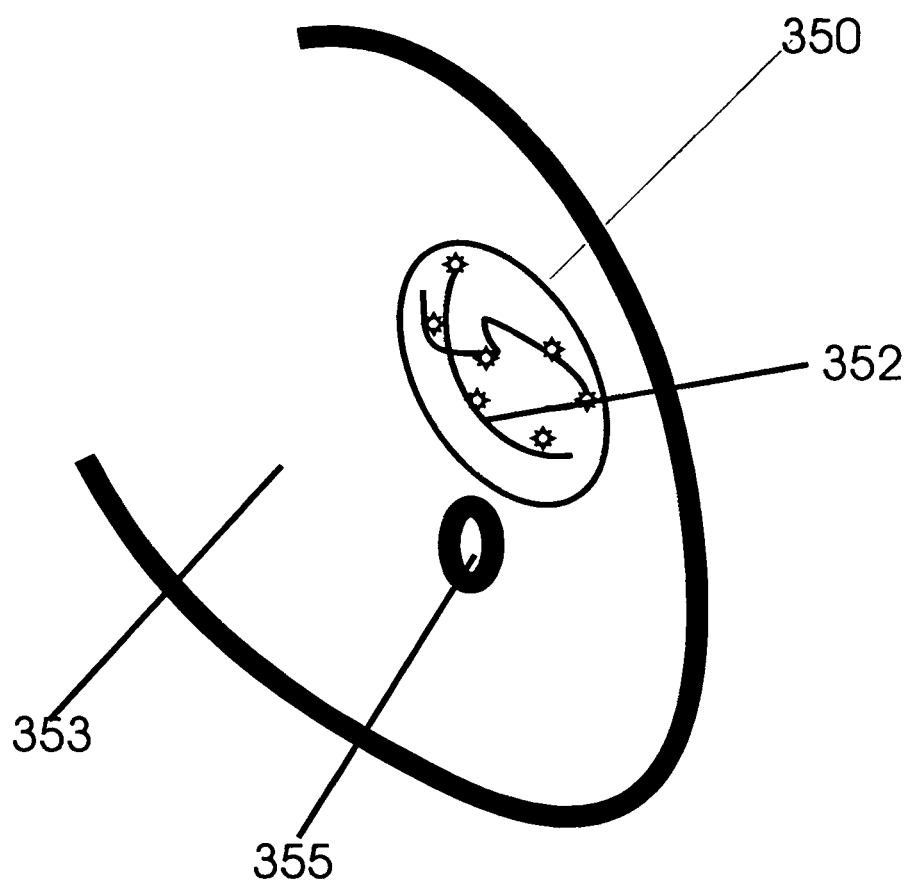
FIG. 15A illustrates an early stage breast cancer with microcalcification
Figure 15B:
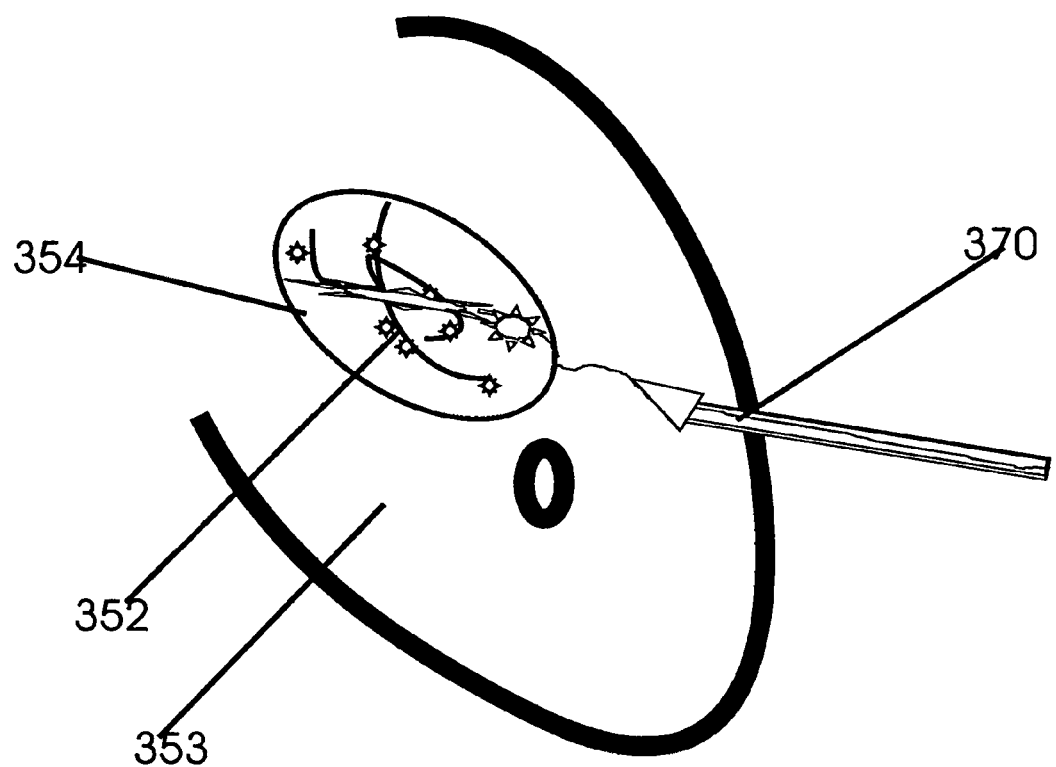
FIG. 15B shows an early stage breast cancer treatment with a single set electronic brachytherapy system
Figures 1, 15C:
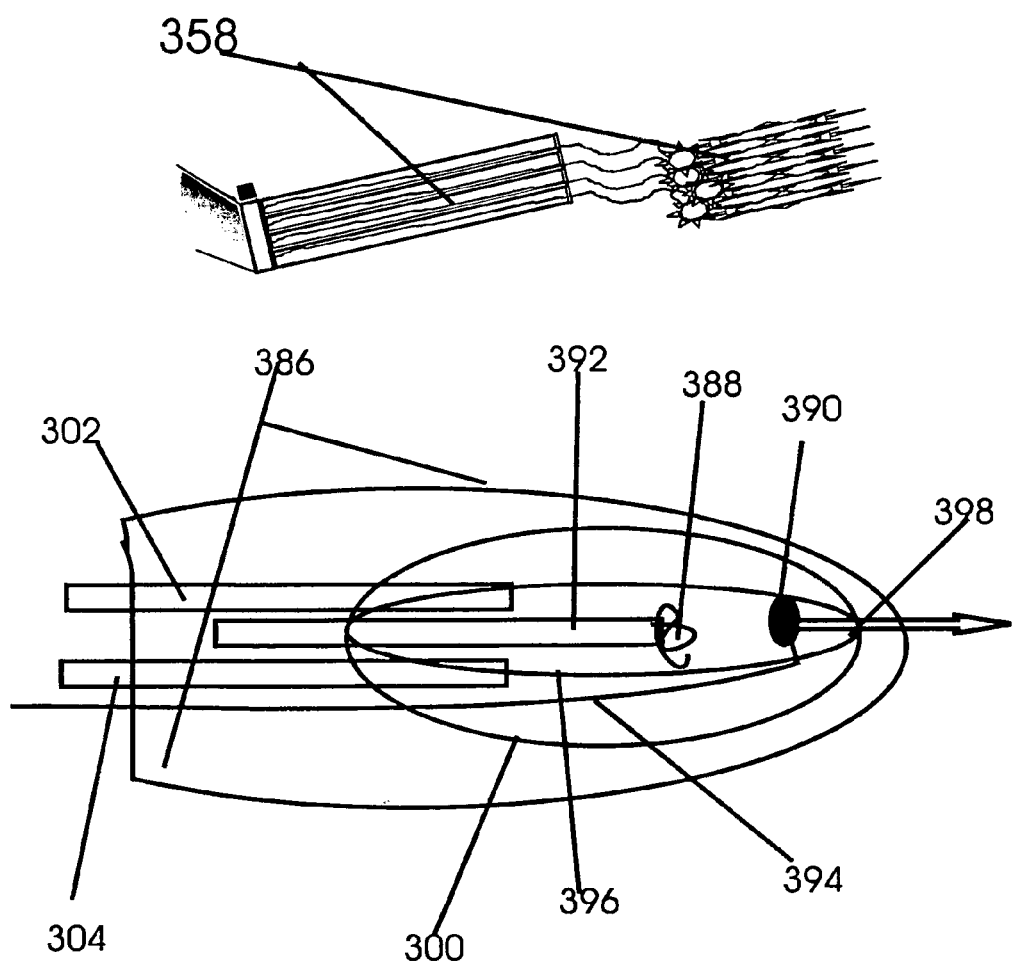
Figures 2, 15C:
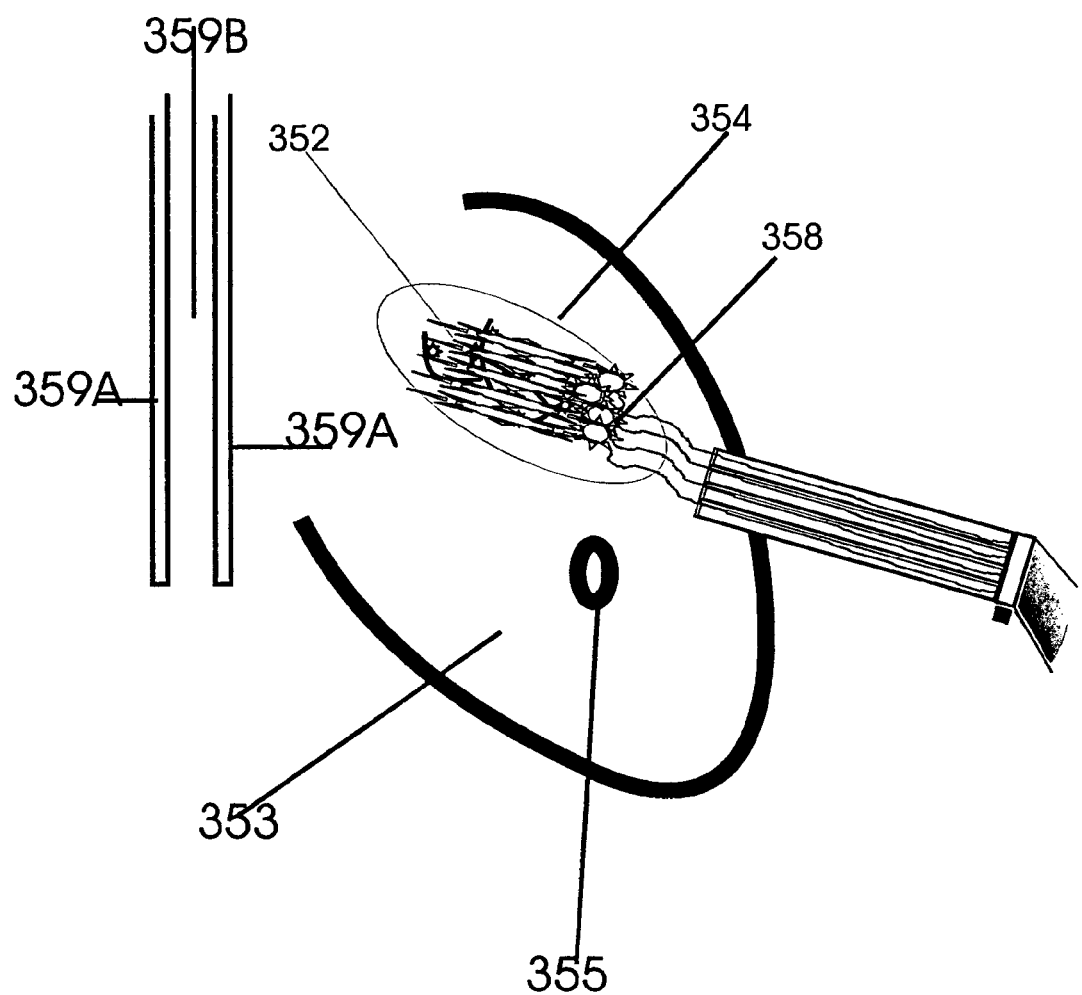

FIG. 2 is a detailed illustration of the basic structures of a CNT based single set, 10 simultaneous converging beams X-ray tube. The miniaturized tiny CNT based field emission cathode 288 is constructed with the metal-oxide-semiconductor field-effect transistor (MOSEFT) 282 and microelectromechanical systems (MEMS) technology. The MEMS technology helps to build very small electromechanical devices. It merges into newer nanoelectromechanical systems. The 10 CNT based field emission cathode 285 has 10 electron beams producing capability either as individually or as simultaneously when the power is supplied to them from each of the 10 MOFEST 282 and MEMS power supply 294 as individually or as simultaneously. The carbon nanotube (CNT) 286 has unique properties that enable the miniaturized cold filed emission electrons. The CNT is deposited on to a MEMS based CNTs holding conductive substrate 284. There are many readily available commercial services such CNT deposition to a substrate. Among them, the method of chemical vapor deposition with ethylene as the carbon source and magnetron sputtering is mostly available. CNT deposition to the substrate is thus either used from the commercial sources or from in house such deposition methods. The power to the CNT-cathode system is controlled by the gate electrode 290. The gate electrode 290 is protected with the insulator 292. The CNT based field emission cathode's electron beam 288 is focused towards the transmission anode 298 by the electron guide 296. As the electron strikes the transmission anode, forward propagating X-ray beam 300 is generated. The cathode-anode system is placed in a vacuum chamber 302. With cold field emission electron generation with CNT and low energy X-ray in the range of 10 kV, much heat is not generated as it is not a thermionic system like the conventional X-ray tubes. Still a water cooler with water inlet and outlets 304 is attached to the anode-cathode system. Water flows through the water inlet 306 and water outlet 308. With smallest, 0.64 mm sized MOFESET and MEME this CNT based X-ray generating, the X-ray tube and the X-ray interstitial implant sources are smallest ones. The whole system is encased into a system insulator 310 for easy handling and its insertion into implant catheters when this or its modified versions are used for interstitial implants.

Figure 3:
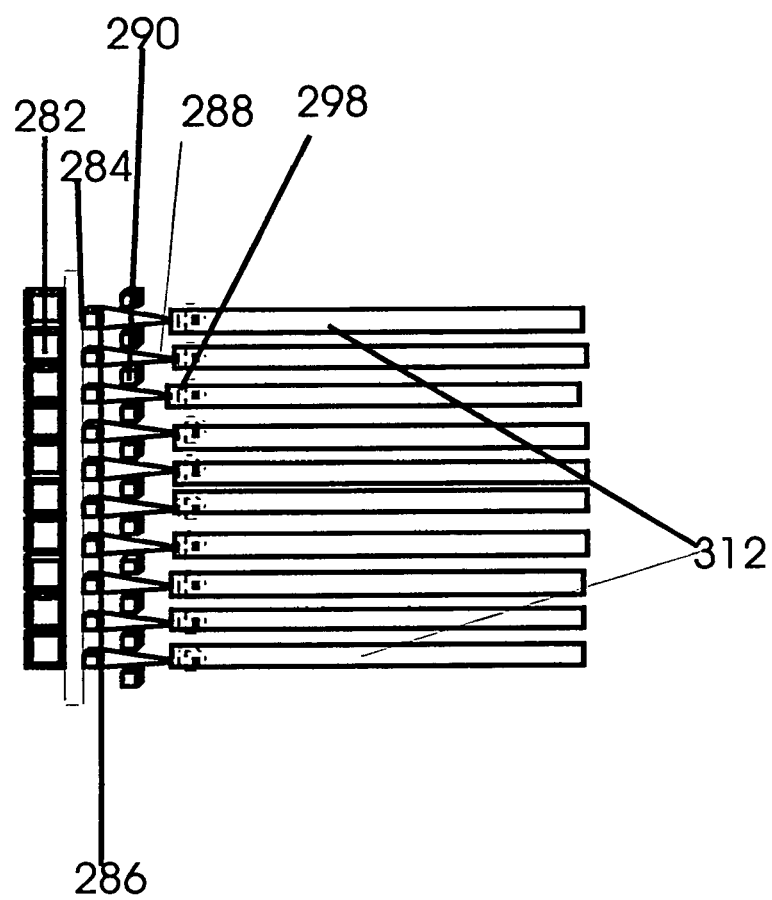
FIG. 3 is an illustration of the basic structures of a CNT based single set, 10 simultaneous parallel beams X-ray tube

FIG. 3 is an illustration of the basic structures of a CNT based single set, 10 simultaneous parallel beams CNT based X-ray tube. Like in FIG. 2, the 10 CNT based field emission cathode 285 has 10 electron beams producing capability either as individually or as simultaneously when the power is supplied to them from each of the 10 MOFEST 282 as individually or as simultaneously. There are 10 carbon nanotube (CNT) 286 cathode sources. The CNT is deposited on to a MEMS based CNTs holding conductive substrate 284. The power to the CNT-cathode system is controlled by the gate electrode 290. The CNT based field emission cathode's electron beam 288 is focused towards the transmission anode 298. As the electron strikes the transmission anode, forward propagating parallel X-ray microbeams 312 is generated.

Figure 4A:
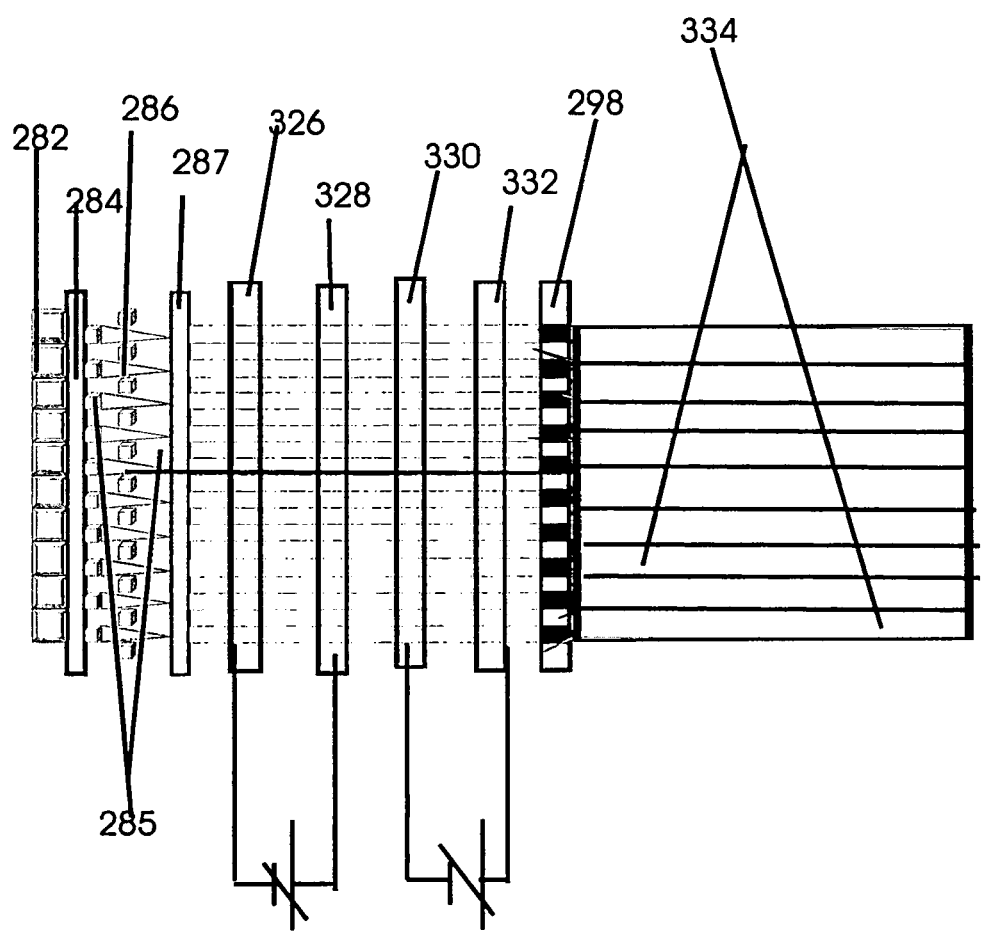
FIG. 4 shows a single set, 10 beam miniaturized electron accelerator based on carbon nanotube field emission (CNT-FE Accelerator).

FIG. 4A shows a single set, 10-beam miniaturized electron accelerator based on carbon nanotube field emission (CNT-FE Accelerator). As described under FIG. 2, the principles of the miniaturized electron accelerator are based on CNT cathode and MOSEFT-MEME technology. Here, the electron is accelerated by changing the polarity of the electrical current that works as a drift tube. The electron so accelerated strikes the transmission anode generating the forward propagating low energy X-ray beam ranging from 10-20 kV or higher. Using the MEMS and the MOSEFT technologies, the miniaturized cathode-anode assembly is constructed. Details of the X-ray tube construction are described under FIG. 2. Here, a basic X-ray tube is constructed as described in FIG. 2. However only its basic features like the MOFESFT 282, MEMS based CNTs holding conductive substrate 284, CNT based field emission cathode 285, carbon nanotubes (CNT) 286, CNT based field emission cathode's electron beam 288, the gate electrodes 290, and the transmission anodes 298 are shown. The CNT based field emission cathode's electron beam 288 is focused by the focusing electrode 287 that let the electron to pass through its pin hole openings (not shown) towards the accelerating electrodes. The accelerating electrodes-1, 326, accelerating electrodes-2, 328, accelerating electrodes-3, 330 and accelerating electrodes-4, 332 acts like a drift tube that accelerates the electron like in a linear accelerator. The electron beam passes through the narrow apertures in the accelerating electrodes (not shown). Each beams passes through its respective aperture in the accelerating electrodes. The focusing electrode 287 and the changing polarity of the accelerating electrodes keeps the electron beam focused and let it accelerate and pass through the apertures in the accelerating electrodes. The accelerated electron strikes the transmission anode 298 that generates the forward propagating low energy X-ray beam ranging from 10-20 kV or higher. The other features that are shown in FIG. 2 for the CNT based x-ray tube like the vacuum, cooling the insulation etc are not repeatedly illustrated here.

FIG. 5, FIG. 6 and FIG. 7 illustrate the left and right halves and a full circle field radiation therapy device. FIG. 5 and FIG. 6 shows the coplanar and non-coplanar transverse, lateral sagital and cranio-caudal-coronal half circle gantry segments attached together with holding screws and to which multiple X-ray sources are placed at 45 degrees apart. In the case of CNT based X-ray tubes, it can be very small. For example, the Oxford Instruments Eclipse II miniature X-ray sources, with integrated 3 W CNT field emission tube and power supply in a small package is 160×38 mm and weighs 300 g. It is operated from batteries (90) With newer MOSEFT measuring just 8 mm outline and 0.357 mm height, much smaller CNT based X-ray tubes for interstitial contact and implant radiation therapy is constructed. This transverse, sagital and coronal radiation source holding gantry is described in U.S. Pat. No. 7,741,624 (7) by this inventor. It is adapted here as an X-ray source holding gantry that can be used intraoperatively and can be dismantled for cleaning and sterilization.

FIG. 5, FIG. 6 and FIG. 7A illustrate the left and right halves and a full circle filed radiation therapy. FIG. 5 and FIG. 6 shows the coplanar and non-coplanar transverse, lateral sagital and cranio-caudal-coronal half circle gantry segments attached together with holding screws and to which multiple X-ray sources are placed at 45 degrees apart. In the case of CNT based X-ray tunes, it can be as small as a dime. This transverse, sagital and coronal radiation source holding gantry is described in U.S. Pat. No. 7,741,624 by this inventor. It is adapted here as a X-ray source holding gantry that can be used intraoperatively and can be dismantled for cleaning and sterilization.

The coplanar plane X-ray sources 198 are shown as attached to cut circular transverse plane gantry 202. The non-coplanar plane X-ray sources 200 are attached to circular sagital lateral plane gantry 206. At 45 degree separation, each segment of the gantry, the transverse, lateral sagital and cranio-caudal-coronal half circle gantry segments can hold 5

X-ray sources. If the one half circle gantry is connected with the other half circle gantry as shown in FIG. 7, each of the three gantry segments can hold a total of eight X-ray sources at 45 degrees apart. For the illustration purpose, only five X-ray sources are shown in this FIG. 5 although these three gantry segments, the transverse, lateral sagital and cranio-caudal-coronal half circle segments can hold 15 X-ray sources at 45 degrees apart. When the two half circles of the three gantry segments, the transverse, lateral sagital and cranio-caudal-coronal half circle segments are held together as surrounding a tissue that is radiated, they holds a total of 24 X-ray sources. These transverse, lateral sagital and cranio-caudal-coronal half circle gantry segments are shown as being held together by three gantry segments locking screws 208. The X-ray sources are attached to the gantry segments with distance and X-ray source adjusting rod 214 on which the X-ray sources are moved forward or backward to adjust distance from the X-ray source to the tissue that is radiated. In this instance the method of radiation therapy is contact therapy. Hence this distance is adjusted to about 2 cm if it is clinically possible. Once this distance is adjusted, the locking screw for X-ray source and distance adjusting rod 216 is tightened to hold the X-ray source firmly on to the gantry. When ready to administer the radiation to a tissue that is treated, the transverse, lateral sagital and cranio-caudal-coronal half circle segments gantry assembly is brought close to the tissue that is being radiated and it is attached to the rails of the surgical table 212 by means of gantry-table-rail connector 210. The number of X-ray sources selected for a given treatment is connected to this gantry assembly to treat a tumor from transverse, lateral sagital and cranio-caudal-coronal planes in conformity with the surgically determined 3-D configuration of the tumor. If the tumor is well covered by treating the tumor from the left half circle gantry configuration as shown in FIG. 5, then the left half circle gantries is used. If the tumor is well covered by treating the tumor from the right half circle gantry configuration as shown in FIG. 6, then the right half circle gantries is used. If the tumor needs to be treated from a full circle to encompass the whole gross tumor (GTV) and the planning treatment volume (PTV), then both half circle gantry are brought together around the treatment volume and they are latched together around the tumor as shown in FIG. 7A for such a conformal tumor volume radiation therapy. The characteristics microbeam intraoperative radiation therapy with multiple simultaneous beams X-ray sources are further described under the following figures and their descriptions.

The number of X-ray sources selected to treat a given tumor in conformity with the tumor volume as viewed from transverse, lateral sagital and cranio-caudal-coronal planes is determined by surgically exposed 3-D configuration of the tumor. If the tumor is well covered by treating the tumor from the left half circle gantry configuration as shown in FIG. 5, then the left half circle gantries is used. If the tumor is well covered by treating the tumor from the right half circle gantry configuration as shown in FIG. 6, then the right half circle gantries is used. If the tumor needs to be treated from a full circle to encompass the whole gross tumor (GTV) and the planning treatment volume (PTV), then both half circle gantry are brought together around the treatment volume and they are latched together around the tumor as shown in FIG. 7A.

FIG. 7B illustrates the intraoperative multiple simultaneous beam radiation therapy to a tumor with multiple miniature thermionic X-ray tubes. The miniature electronic brachytherapy X-ray tube 370 are attached to X-ray tube holding ring with running cooling water 374 equipped with running cooling water outlet 376 and X-ray tube and electrical accessories holding rings 378. The miniature electronic brachytherapy X-ray tubes 370 that are generally used for electronic brachytherapy is well known in the art. They are described in several US patents and thirty of them are cited in section 3, "Electronic Brachytherapy X-ray Tubes (EBT-Tubes) and Simultaneous Multi-Barn Brachytherapy". They date back to 1973. The principles of these patents on miniaturized X-ray tubes suitable for electronic brachytherapy are incorporated into this invention by their full reference. Such miniaturized X-ray tubes are used in this invention for multiple simultaneous beam intraoperative radiation therapy. Since they are well known in the art, they are not further described here. The multiple miniaturized X-ray tubes arranged in a circle on X-ray holding rings provide multiple simultaneous broad beams 380 that radiate the tumor.

Radiation therapy with broad beam does not spare the normal tissue as the radiation therapy with microbeam with its peak and valley that is described in this invention. Hence the capabilities to treat a tumor with high dose as it is possible with microbeam are not available when the treatment is given with broad beam.

FIG. 7C illustrates intraoperative radiation to a tumor as shown in FIG. 7B but with CNT based-X-ray parallel microbeam. Four CNT based X-ray tube 384 is shown as placed on to the X-ray tube holding ring with cooling running water 374 with water outlets 376 and on to the X-ray tube and electrical accessories holding rings 378. The X-ray tubes are placed at 0, 45, 90 and 135 degrees apart. Their parallel microbeams are shown as radiating a tumor 380. The 25 to 75 μm wide parallel microbeams are spaced at 500 μm apart. It radiates the normal tissue in the peak region at 100% of the dose and spears the valley region from higher dose radiation by having only about 10% or less of the peak radiation. Hence high dose, 100-500 Gy single fraction curative intraoperative radiation therapy with no or minimal toxicity to normal tissue is made possible. The dose deficiency in the valley regions in between the microbeams is filled by the scatter and characteristic radiation and the k, l, m, n shell Auger radiation that is produced by tuning the energy of the X-ray beam to the binding energy of the high Z-element that is bound or implanted to the tumor.

FIGS. 7D and 7E shows four sets of CNT based micro-accelerators 281 and their simultaneous 10 parallel microbeams 357 radiating a surgically exposed tumor. The CNT-based micro-accelerators 281 are attached to the X-ray tube and electrical accessories holding ring 378 and X-ray tube holding ring with cooling running water 374 at 0, 45, 135 and 270 degrees. In FIG. 7E, the CNT-based micro-accelerators are 281 are attached to the X-ray tube and electrical accessories holding ring 378 and X-ray tube holding ring with cooling running water 374 at 0, 45, 90 and 135 degrees. The heat generated by the miniature micro-accelerators is transferred to the circulating water that runs through the water outlets 376. Simultaneous 10 parallel microbeams 357 from each of the four CNT based micro-accelerators expose the tumor 382 as they intersect at the site of the tumor 382. The parallel microbeams do not cross each other after their intersection through the tumor 382. Hence the peak and valley dose in between the parallel microbeams do not intermix in the normal tissue. It assures minimal radiation to the normal tissue and rapid normal tissue recovery from radiation. Thus, the single fraction radiation to the tumor is in the range of about 200-500 Gy and higher. Because of the high dose rate of up to about 20,000 Gy/sec, the beam exposure lasts only a fraction of a second. The dose deficiency in the valley regions in between the microbeams is filled by the scatter and characteristic radiation and the k, l, m, n shell Auger radiation that is produced by tuning the energy of the X-ray beam to the binding energy of the high Z-element that is bound or implanted to the tumor.

FIG. 8 illustrates four sets of CNT based parallel X-ray microbeams X-ray tubes 312 all arranged within a circle and each X-ray tube having 10 parallel microbeams, parallel microbeams X-ray tube with 10 beams from 0° 314, parallel microbeams X-ray tube with 10 beams from 90° 316, parallel microbeams X-ray tube with 10 beams from 180° 318, and parallel microbeams X-ray tube with 10 beams from 270° 320. The cross firing parallel microbeams from 0 and 180 and 90 and 270 degrees at the center 322 is shown as exposing a square field at the center with 40 simultaneous parallel microbeams. The details of the CNT based X-ray tubes are described in FIG. 2 and in FIG. 3.

Parallel microbeam stimulative treatment is reported to help the regeneration normal nerve tissue in U.S. Pat. No. 7,194,063 (69) and U.S. Pat. No. 7,746,979 (70) by Dihnanian et al. In these patents, the external microbeams from 100 to 250 kV X-rays are used for the nerve stimulation. This methods of microbeam radiation therapy with external 100-250 keV X-rays is difficult to implement. By this method, only a very small percentage of the dose will reach the thalamus and globus palladium as they are deep seated structures in the brain. Its skin dose and the dose to other parts of the brain through which the micro beams travels would be very high. The recommended dose is 30 to 500 Gy, which is 3,000 to 50,000 cGy. If about 60% of the beam reaches the deep seated basal ganglia, the skin, skull and normal brain dose would be in the range of 5,000 to 83,000 cGy per fraction of the 20-30 treatments given in at intervals ranging from 12 hours to one week (70). The time taken to administer the middle of the road dose of 100 Gy to the deep seated basal ganglia at 2 Gy/min dose rate and at about 60% depth dose is 83 min. It would be impossible to keep a patient immobilized and still during the recommended 20 to 100 μm and or 1 to 2 mm wide parallel beams.

On the other hand, if diseases like Parkinson's disease is treated with parallel micro beams from implanted miniaturized X-ray tubes as shown in this figure or interstitial X-ray tubes implants also as in this invention, many of the above disadvantages like treating the diseased tissue with 100-250 kV can overcome. Low energy beam like 10 kV has much superior radiobiological effectiveness than the 100-250 kV X-rays. It is locally absorbed. It does not expose the normal tissue as the 100-250 keV x-rays used in U.S. Pat. No. 7,194,063 (69) and U.S. Pat. No. 7,746,979 (70). Treating a lesion with elective number of simultaneous beams and with low energy parallel microbeam as in this invention is more stimulating for the healthy cells like the nerve cell to migrate to the diseased site and repopulate.

Figure 9:
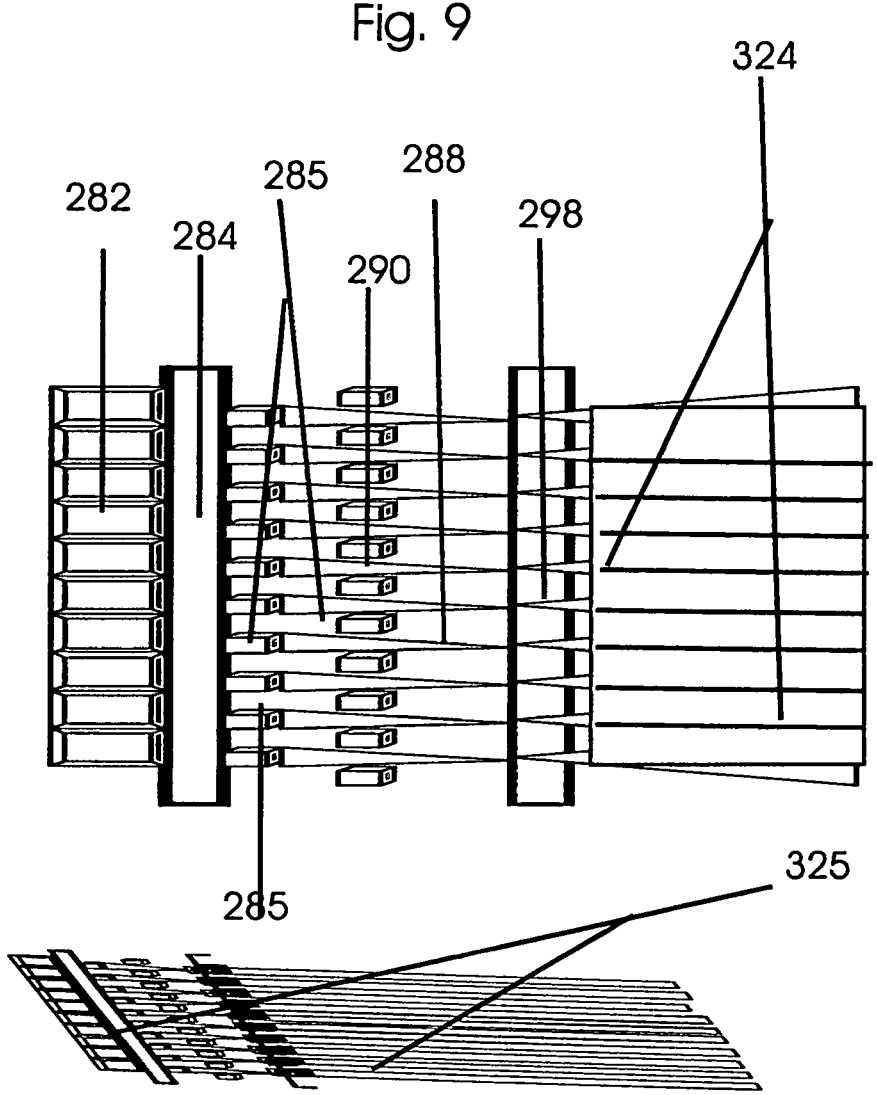
FIG. 9 is an illustration of a miniaturized interstitial implant 10 beam CNT based X-ray tube with it's the basic structures.
Figure 10:
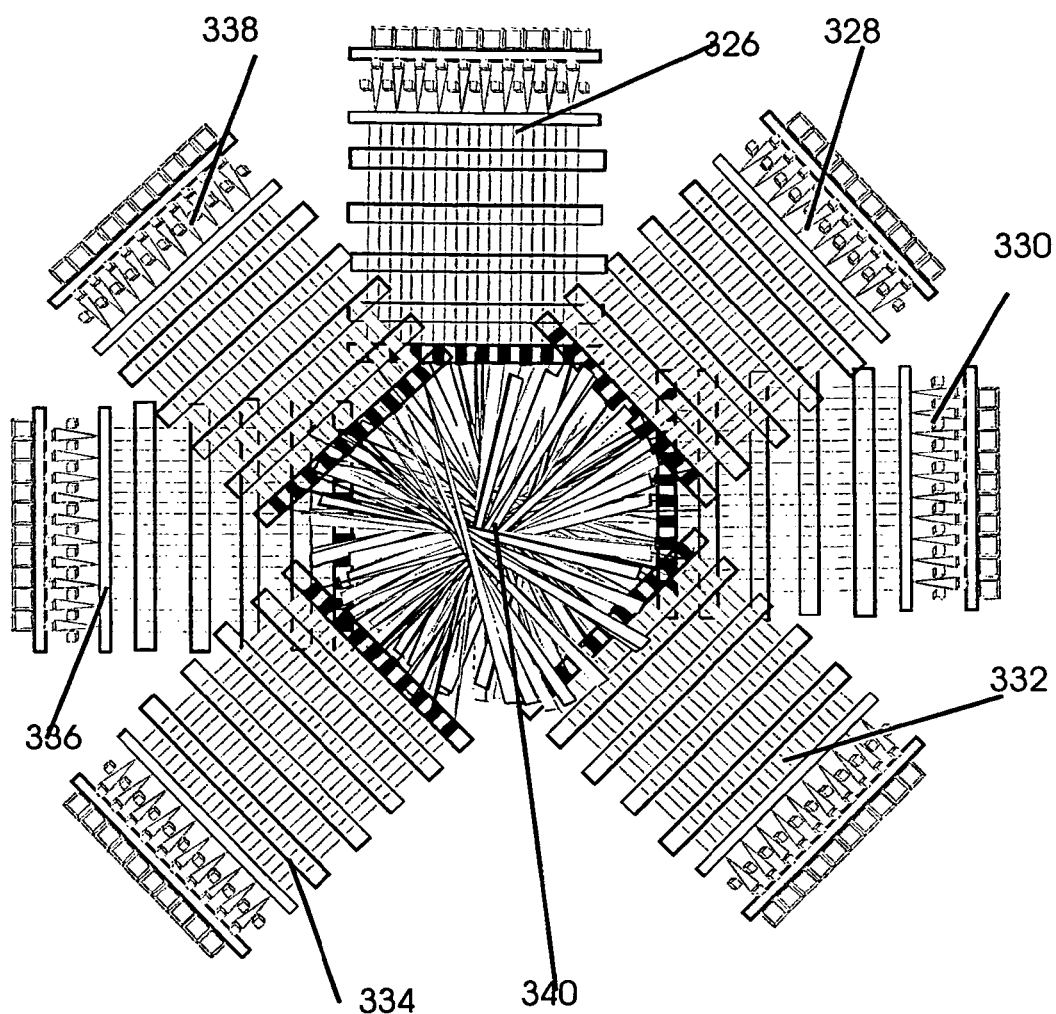
FIG. 10 is an illustration of seven CNT based external electron accelerates with combined 70 external microbeams that are passing through the isocenter

FIG. 9 and FIG. 10 shows miniaturized interstitial implant with CNT based X-ray tubes and their basic structures. Their CNT based parallel X-ray microbeam 324 is switched as simultaneous microbeams or as individual microbeams or as several microbeam groups. Its detailed structures are shown in FIGS. 2 and 3. Like in FIGS. 2 and 3, the 10 CNT based field emission cathode 285 has 10 electron beams producing capability either as individually or as simultaneously when the power is supplied to them from each of the 10 MOFEST 282. There are 10 carbon nanotube (CNT) 286 cathode sources. The CNT is deposited on to a MEMS based CNTs holding conductive substrate 284. The power to the CNT-cathode system is controlled by the gate electrode 290. The CNT based field emission cathode's electron beam 288 is focused towards the transmission anode 298. As the electron strikes the transmission anode, forward propagating parallel X-ray microbeams 324 is generated. Such a CNT based X-ray tube 325 is shown in the insert.

FIG. 10 is an illustration of seven CNT based external electron accelerates with combined 70 microbeams that are passing through the isocenter. This seven set of miniaturized, CNT based accelerators includes 10-beam miniature accelerator-1, 326, 10-beam miniature accelerator-2, 328, 10-beam miniature accelerator-3, 330, 10-beam miniature accelerator-4, 332, 10-beam miniature accelerator-5, 334, 10-beam miniature accelerator-6, 336, and 10-beam miniature accelerator-7, 338. Their combined microbeams meet at the isocenter 333.

These accelerators are used for low energy contact treatment as in low energy Grenz ray therapy to an operatively exposed tumor from multiple angles and with multiple simultaneous beams. Alternatively, their higher energy version is used as multiple external microbeam sources for intraoperative radiation. Their interstitial version is used for simultaneous up to 70 microbeam interstitial brachytherapy with CNT based miniature X-ray tubes. Its other use includes treating skin tumors either as contact-Grenz ray therapy or as interstitial brachytherapy.

FIG. 11 is an illustration of eight units, 10 beams each; external CNT based field emission accelerator based combined 80 microbeams radiation therapy system with all the beams converging at the isocenter. The CNT based 10 beams micro-accelerator 340 and its 10 simultaneous monochromatic microbeams 342 are described under FIG. 4. The simultaneous beams additive dose is at the isocenter 333 where the treating tumor is generally located. Each micro beams passes through the normal tissue towards the isocenter 333. Such microbeam facilitates the broad beam effect at the isocenter and near parallel beam effects at the normal tissue. The single fraction dose that is administered at the isocenter is in the range of 200 to 300 Gy (20,000 to 30,000 cGy). Because of the microbeam radiation and the normal tissue sparing by such microbeam radiation, such single fraction high curative dose to the isocentric tumor with the tumor stem cell can be administered without much toxic effects to normal tissue. It kills the "differentiated" tumor cells and the tumor stem cell that usually survives when radiation is administered at conventional radiation therapy's lower fractionated total dose in the range of 70-80 Gy (7,000 to 8,000 cGy). The normal tissue regeneration towards the space occupied by the former tumor tissue accelerates the healing process. Such intraoperative CNT based X-ray beam's dose rate almost matches and or exceeds the dose rate of synchrotron based micro beams as discussed under "Additive high dose rate intraoperative radiation therapy with multiple simultaneous microbeams from CNT based X-ray tubes" before. This opens the opportunity for organ preserving radiation therapy for number diseases. Whole breast preservation radiation therapy without any major surgeries except for a simple needle biopsy for diagnosis is an important treatment for every woman with breast cancer. There are many such diseases where organ preservation is important.

Figure 13A:
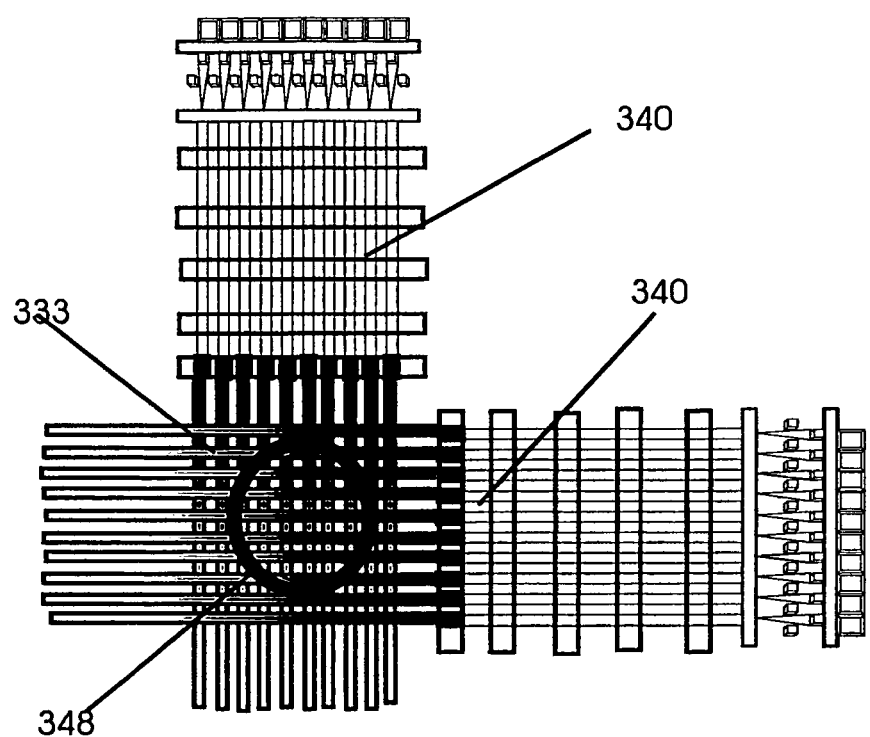
FIG. 13A illustrates two orthogonally placed CNT based 10 microbeams micro-accelerators, one at 0 degree and the other at 90 degrees with their parallel microbeams cross-firing at the isocenter where the planning tumor volume is located.
Figure 13B:
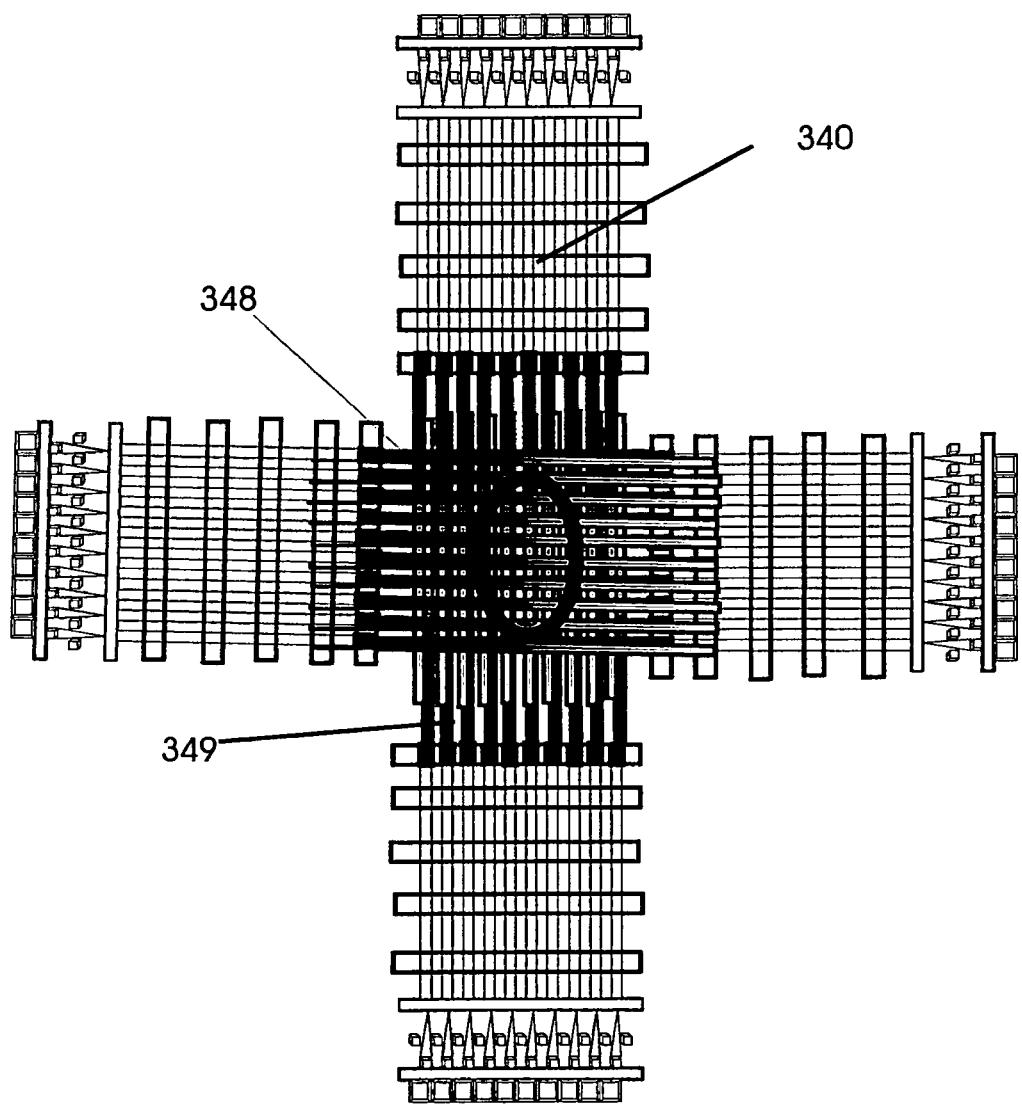
FIG. 13B shows four miniaturized CNT based accelerator's combined 40 parallel opposing microbeams exposing a panning tumor volume bearing region that forms a square radiation field at the isocenter.

FIG. 12, FIGS. 13A and 13B shows miniaturized 10 parallel beams accelerator for interstitial implant. FIG. 12 illustrates the same 10-beam miniaturized electron accelerator based on carbon nanotube field emission as in FIG. 4 but without the detailed descriptions of the structures as in FIG. 4. It is shown here to describe the external and implant radiation with CNT based 10-beam micro-accelerators 340 and their 10 simultaneous parallel microbeams 342. FIG. 13A illustrates two orthogonally placed CNT based 10 microbeams micro-accelerators 340, one at 0 degree and the other at 90 degrees with their parallel microbeams cross-firing at the isocenter where the planning tumor volume 348 is located. The parallel microbeams spaced at 500 µm apart radiates the normal tissue in the peak region at 100% of the dose and spears the valley region from higher dose radiation by having only about 10% or less of the peak radiation. Hence the parallel microbeams with 500 µm spacing in between is used to treat a tumor with curative dose of 500-5,000 Gy without causing much toxicity to the normal tissue. The microbeam valley's radiation at the tumor bearing site at the isocenter 333 is enhanced by the scatter and characteristic radiation and the k, l, m, n shell Auger radiation that is produced by tuning the energy of the X-ray beam to the binding energy of the high Z-element that is bound or implanted to the tumor.

FIG. 13B shows four such miniaturized CNT based accelerator's 340 combined 40 parallel opposing microbeams 349 exposing a panning tumor volume 348 bearing region that forms a square radiation field. The parallel opposing microbeams spaced at 500 µm apart radiates the normal tissue in the peak region but still spears the valley region from higher dose radiation. Hence with such parallel opposed microbeams with 500 µm spacing in between treats a tumor with 100-200 Gy and higher curative dose. The microbeam valleys at the tumor bearing site of the isocenter is enhanced by the scatter and characteristic radiation and the k, l, m, n shell Auger radiation that is produced by tuning the energy of the X-ray beam to the binding energy of the high Z-element that is bound or implanted to the tumor.

FIG. 14A illustrates selectively switched parallel opposing 6 simultaneous beams 341 from four sets of miniaturized CNT based 10 microbeams micro-accelerators 340 that covers the planning tumor volume 348 but with sparing of the isocentric region where no tumor is located. By selectively switching of the microbeams, the spared isocentric region from radiation 347 is created. It functions as a superior collimation of the beams. Six beams from each of the accelerator set's 10 beams are selectively switched on. The beam width is selected as 25-75 µm width. They are spaced at 200-400 µm apart. Its additive broad beam effect at the isocentric tumor site and parallel beam effect in the normal tissue spares the normal tissue while the tumor tissue is treated with high single fraction dose of 100-200 Gy that sterilize both the differentiated tumor cells and its stem cells. The unexposed or minimally radiated normal cell regeneration helps to heal the former tumor cell bearing tissue.

Figure 14B:
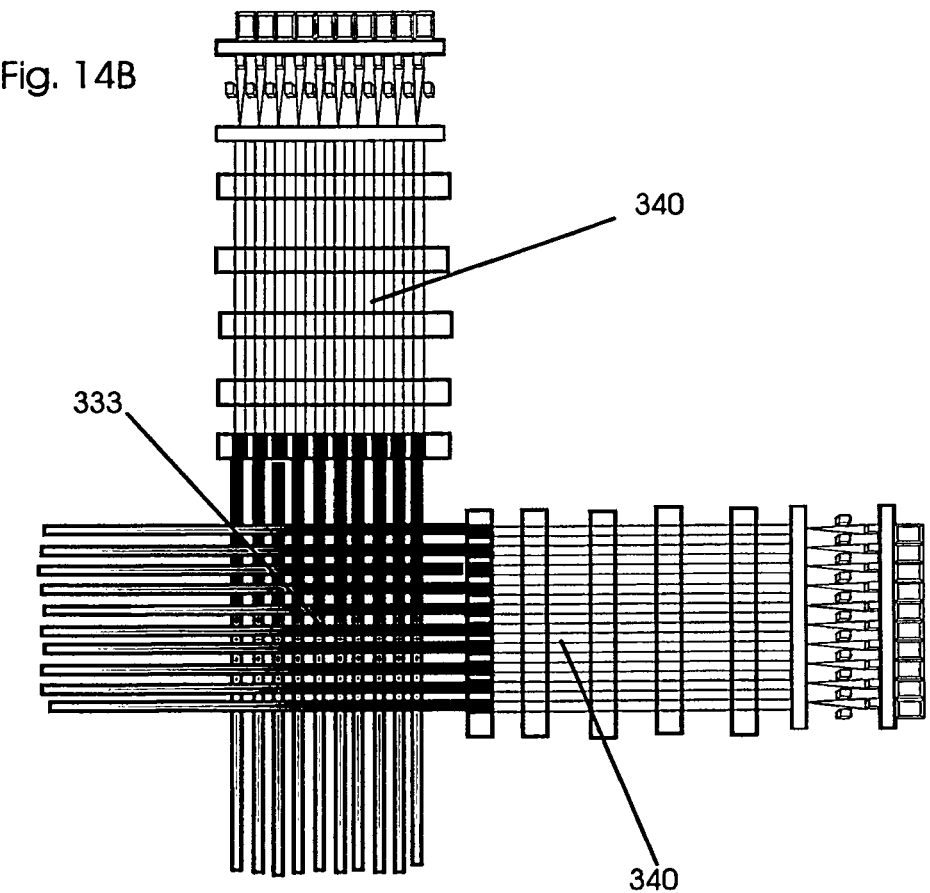
FIG. 14B shows the parallel microbeams from a set of miniaturized accelerators placed at 0 and 90 degrees as these parallel microbeams intersects at the isocenter and these beams not overlapping in the normal tissue outside the isocenter.

FIG. 14B illustrates the parallel microbeams 342 from a set of 0 and 90 degree orthogonal miniaturized accelerators as these parallel microbeams intersecting at the isocenter 333 and these beams not overlapping in the normal tissue outside the isocenter 333. The valley dose outside the isocenter is very low. This spares the normal tissue and hence dose in the range of 500 Gy and higher can be administered to an isocentric tumor.

FIG. 15A, 15B, 15C, 15D, FIG. 16 and FIG. 17 illustrates an early stage breast cancer with microcalcification and treating a tumor with electronic brachytherapy or with CNT based X-ray tube's parallel microbeam radiation therapy. In FIG. 15A, a breast 353 with nipple 355 and an early stage breast cancer 354 with microcalcification 352 is shown. The FIG. 15B shows this early stage breast cancer 354 with microcalcification 352 as treated with a single set electronic brachytherapy X-ray tube 370.

FIG. 15C-1 shows a single micro-X-ray tube assembly for implant 386. The micro-X-ray tube filament cathode 388 and the micro-X-ray tube anode 390 are enclosed within a vacuumed glass tube 396. The cathode lead cable 392 and anode lead cable 394 supplies the electrical power to the cathode and the anode. The X-ray produced from the anode passes through the window 398 in the forward direction of the arrow as is shown in the illustration. The vacuumed glass tube 396 containing the cathode and the anode is enclosed in the vacuumed tube and anode and cathode holding glass container 300. The anode and the cathode are cooled with circulating water that flows through water inlet 302 and water outlet 304. Four such micro-X-ray tubes are put together that makes a single micro-X-ray tube assemblies for the implant 358. Other examples of miniature X-ray sources like those with cold emission cathode is also adapted for interstitial micro-X-ray tube implant. A few mm sized micro-X-ray tubes are used for vascular radiation. Multiple cold emission cathode micro-X-ray tubes of a few mm in size are also assembled together (not shown here) for multiple simultaneous microbeam implant radiation therapy that is described in this invention The FIG. 15C-2 illustrates an early stage breast cancer 354 as treated with a single simultaneous four microbeam beam electronic brachytherapy system 358. The microbeams are spaced at 500 µm from each other. The electronic brachytherapy microbeam peak dose 359A and the electronic brachytherapy microbeam valley dose 359B are shown in the insert. While the electronic brachytherapy microbeam peak dose 359A has 100% of the microbeam dose, the electronic brachytherapy microbeam valley dose 359B is only about 10% of the peak dose. Because of this low valley dose, normal tissue tolerance to radiation is increased significantly, in the range of 500 to 5,000 Gy when the width of the microbeam in the range of 25-75 µm (54, 55).

FIG. 15lD illustrates an early stage breast cancer 354 treatment with four separate simultaneous four microbeam electronic brachytherapy systems 358. The first of the four microbeam electronic brachytherapy systems 358-1 microbeam set is inserted at 0-degree, second 358-2 is inserted at 45-degree, the third 358-3 is inserted at 135-degree and the fourth 358-4 is inserted at 220 degrees. Their combined 16 microbeams are shown as intersecting at the isocentric tumor 354. The electronic brachytherapy microbeam peak dose 359A and the electronic brachytherapy microbeam valley dose 359B are shown in the insert. As described under FIG. 15C, while the electronic brachytherapy microbeam peak dose 359A has 100% of the microbeam dose, the electronic brachytherapy microbeam valley dose 359B has only about 10% of the peak dose. Because of this low valley dose, normal tissue tolerance to radiation is increased significantly, in the range of 500 to 5,000 Gy when the width of the microbeam in the range of 25-75 µm (54, 55). The valley dose in between the 500 µm spaced microbeams where they intersect is enhanced by the scattered and the k, l, m, n shell characteristic and Auger radiation. It is also enhanced by selectively tuning the energy of the microbeam to the binding energies of the k, l, m, n shell of the high Z elements that is locally bound or implanted. The scattered and characteristic X-rays have predominantly low energy radiation, in the range of 10-20 keV. It's RBE is close to that of high LET radiation. This RBE is further enhanced by the sixteen simultaneous beam's additive high dose and dose rate. Single fraction higher dose and dose rate interstitial brachytherapy with 16 simultaneous microbeam with 4 simultaneous four microbeam electronic brachytherapy systems 358 improves the whole breast preservation radiation therapy at doses 100-200 Gy and higher wiout normal tissue toxicity and whole breast preservation without breast deformity and cancer stem cell sterilization that assures no or rare local tumor recurrence. However, due to lower dose rate of individual beams, its relative treatment time is longer than when a tumor is treated with CNT based X-ray tubes with dose rate close to 20,000 Gy/sec.

Figure 16:
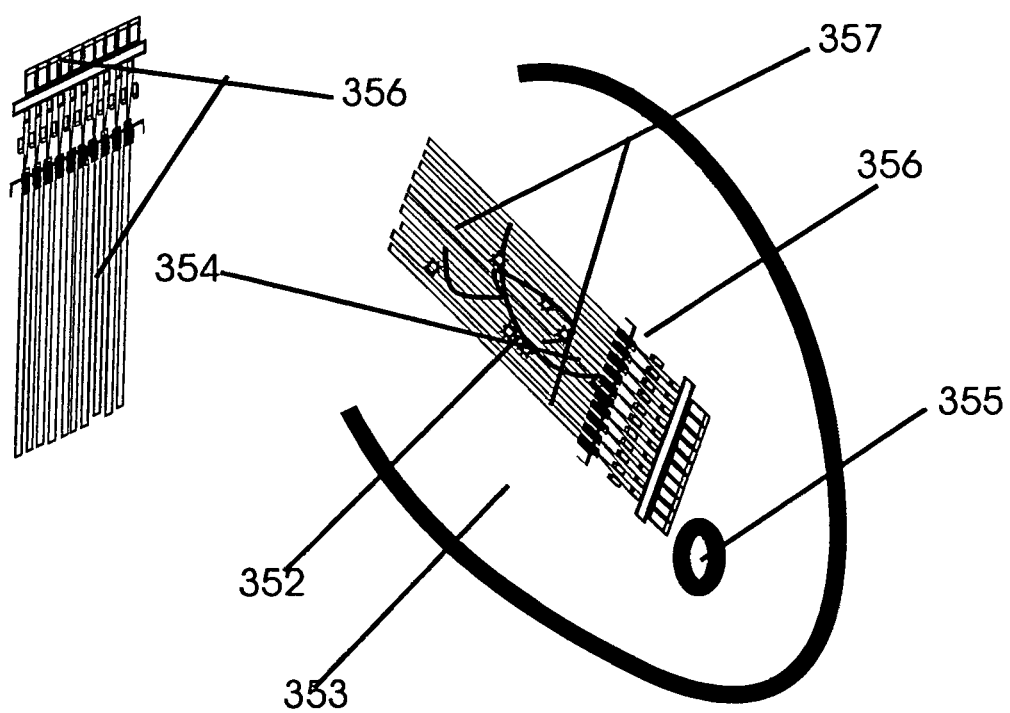
FIG. 16 illustrates treating an early stage breast cancer with microcalcification and with a single beam electronic brachytherapy system
Figure 17:
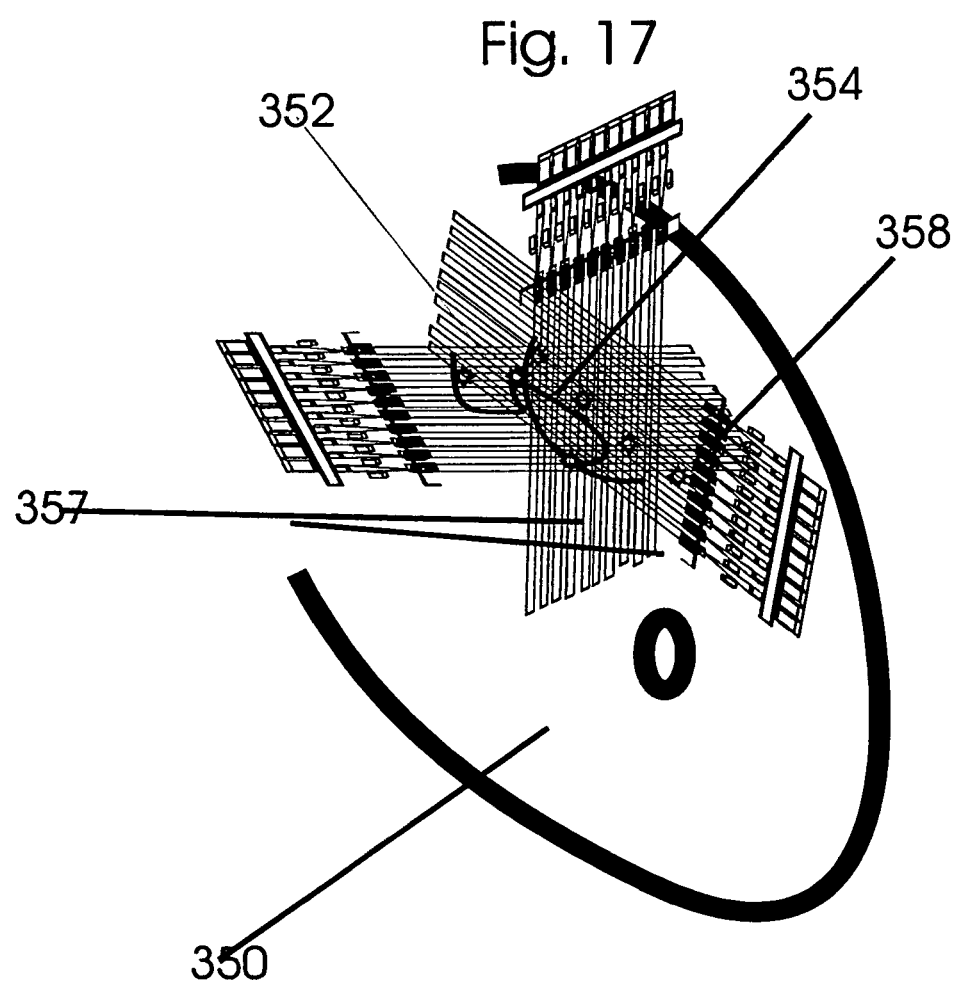
FIG. 17 shows an early stage breast cancer with ductal microcalcification being radiated with 3 sets of miniature interstitial implant, each with 10 parallel microbeams and thus with a total of 30 parallel microbeams
Figure 21:
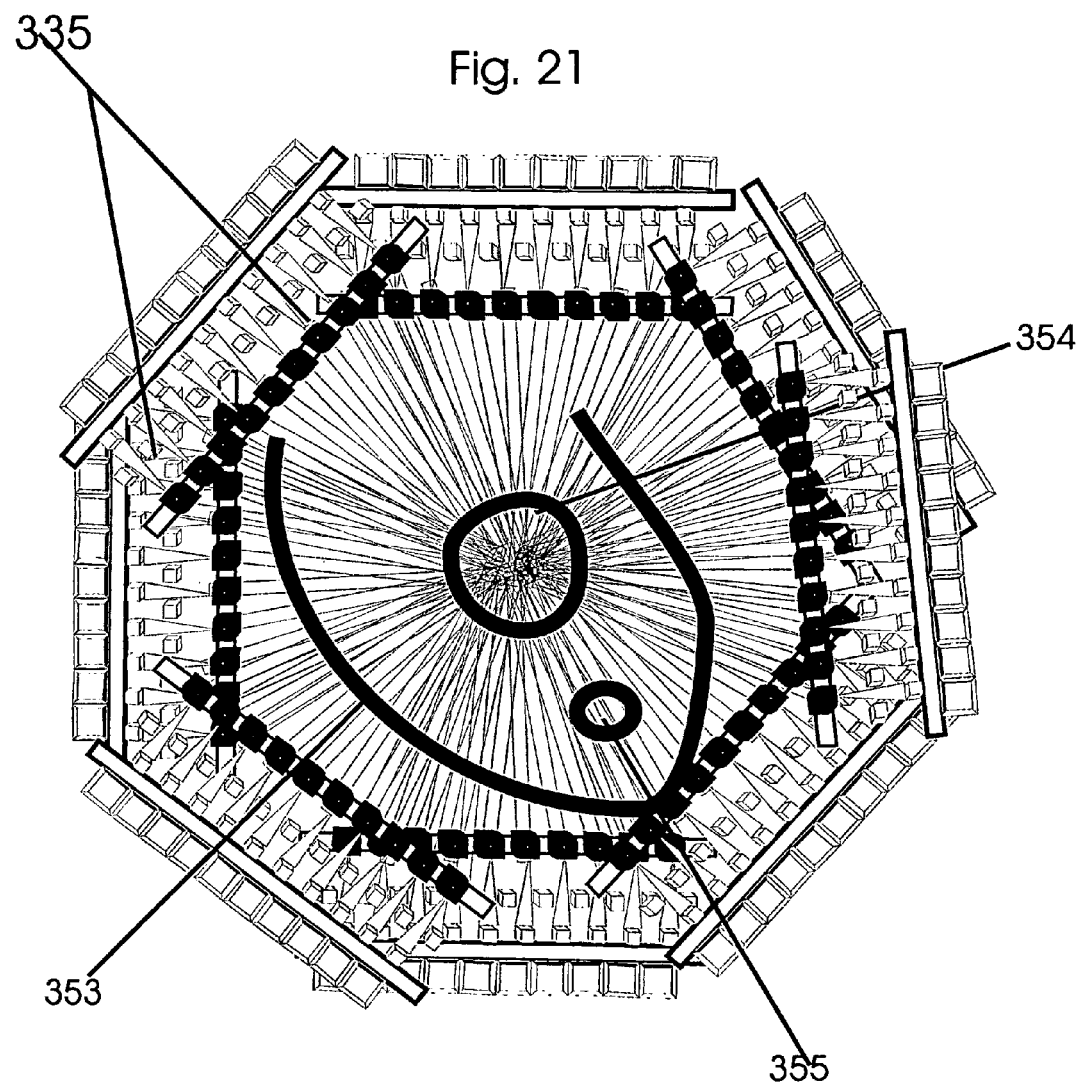
FIG. 21 illustrates the method of whole breast radiation with concomitant high dose to the tumor with eighty focused simultaneous external microbeam from CNT based X-ray tubs and each set's 10 beams as focused to the isocenter and with higher dose to the isocentric tumor from eighty microbeams converging at the isocenter

In FIG. 16 and FIG. 17, the same breast 353 with early stage breast cancer 354 is shown with a CNT based miniature interstitial implant with 10 parallel microbeams 356. This miniature accelerator structures are described in FIG. 3. The simultaneous 10 parallel microbeam 357 is shown as radiating the entire region of micro calcification. The insert shows the interstitial implant 356. Its basic structures are described in detail under FIG. 3. Because of the parallel microbeam that radiates the tumor tissue with high intensity radiation while sparing the adjacent normal tissue much higher single fraction radiation to the tumor bearing region is administered. Such high dose radiation is not feasible with conventional alternative external or electronic brachytherapy or brachytherapy with radioactive isotopes. In FIG. 17, (23), the same early stage breast cancer 354 with ductal microcalcification 352 that is shown in FIG. 21 is illustrated with 3 sets of miniature interstitial implant with 10 parallel microbeams 356, with a total of 30 parallel microbeams 357. This 30 beam parallel microbeams generates a broad beam effect at the tumor site of the implant while in the rest of the tissue thorough which it travels, it is parallel to each other.

Because of the low valley dose, normal tissue tolerance to radiation is increased, in the range of 500 to 5,000 Gy when the width of the microbeam in the range of 25-75 μm (54, 55). The valley dose in between the 200 to 500 μm spaced microbeams where they intersect is enhanced by the scattered and the k, l, m, n shell characteristic and Auger radiation. It is also enhanced by selectively tuning the energy of the microbeam to the binding energies of the k, l, m, n shell of the high Z elements that is locally bound or implanted. The scattered and characteristic X-rays have predominantly low energy radiation, in the range of 10-20 keV. It's RBE is close to that of high LET radiation. This RBE is further enhanced by the high dose rate of CNT based X-ray tubes. The simultaneous three ports, CNT based 30 microbeam brachytherapy improves the whole breast preservation radiation therapy at doses 200-500 Gy and higher without normal tissue toxicity and whole breast preservation without breast deformity and cancer stem cell sterilization. It assures no or rare local tumor recurrence. This method of radiation to the tumor to a dose of 200-500 Gy and over kills both the "differentiated" tumor cell and the dormant tumor stem cells assuring the tumor cure. Because of the very high dose rate of the CNT based microbeam, in the range of 20,000 Gy/sec, such radiation is completed in a fraction of a second. Such radiation with minimal toxic effect to normal tissue is not feasible with present conventional radiation or with present electronic brachytherapy. Since such high curative dose radiation therapy to the tumor is made possible, the need for routine surgical excision of the tumor or mastectomy is eliminated for most breast cancers. It is just a simple needle biopsy followed by curative cosmetically very acceptable intact whole breast preserving radiation therapy.

Figure 18:
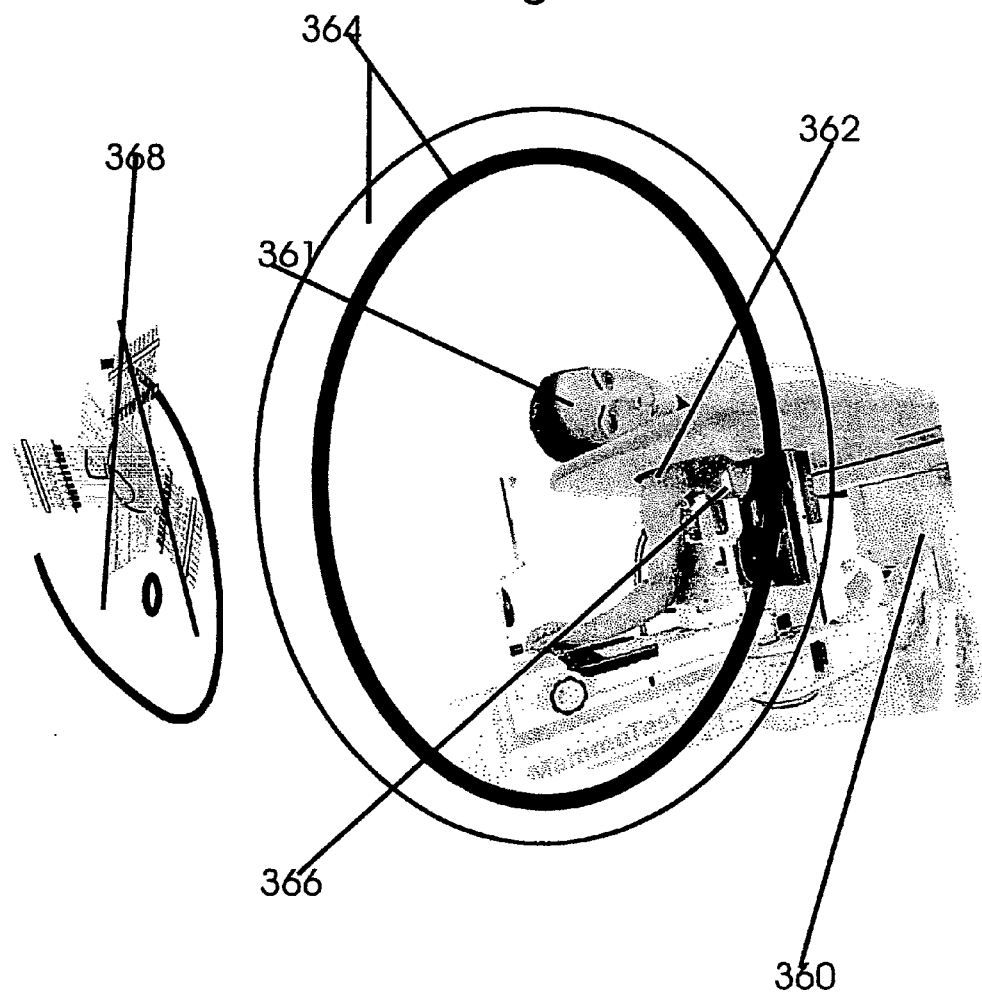
FIG. 18 shows a commercially available stereotactic breast core biopsy system adapted for combined simultaneous biopsy and positron emission tomography (PET) combined with computerized tomography (CT) imaging for CNT based parallel X-ray beam brachytherapy treatment planning and with an insert of three sets, thirty parallel microbeams implant that is performed simultaneously with the stereotactic breast biopsy.

FIG. 18 shows a commercially available stereotactic breast core biopsy system adapted for combined simultaneous biopsy and positron emission tomography (PET) combined with computerized tomography (CT) imaging for CNT based parallel X-ray beam brachytherapy treatment planning and with an insert of three sets, thirty parallel microbeams implant that is performed simultaneously with the stereotactic breast biopsy. After the mammography, any patients with suspected microcalcifications will generally undergo diagnostic biopsy. For those patients wishing to have whole breast preservation with minimal or no cosmetic deformity will be advised to have combined minimally invasive stereotactic breast core biopsy or needle biopsy and if the immediate online, onsite histological analysis of the biopsy specimen shows definitive evidence of carcinoma, then to have immediate, same settings single session interstitial X-ray based brachytherapy to the tumor site alone or combined with whole breast radiation therapy with parallel or converging microbeams. The converging microbeam is almost parallel during its course of travel to the region where the tumor is located. The multiple parallel microbeams from different angles form a broad beam as they cross the tumor.

The treatment with parallel microbeam facilitates treating the tumor at much higher dose, 200-300 Gy and higher that kills the "differentiated tumor cells and the dormant cancer stem cell. In this instance, the question of residual tumor at the tumor bed and or at the resection margin becomes a mute question. The total dose administered by the methods of present conventional fractionated radiation therapy is in the range of 50 to 60 Gy. Hence it does not sterilize all the "differentiated" tumor cells and more importantly, also not the Cancer stem cells. Hence the importance of tumor free tumor bed and resection margin when a patient is treated by the conventional broad beam fractionated low total dose radiation. Treating a tumor with multiple simultaneous parallel microbeams and at much higher dose of 200 to 300 Gy in a single fraction with less toxicity to normal tissue due to rapid healing by the normal tissue proliferation to the former tumor tissue site and leaving no residual cancer stem cells makes such treatment curative. Treating the tumor at the time of its first surgical intervention in the form of stereotactic needle biopsy eliminates the tumor recurrence from the implanted tumor cells in the needle track. By avoiding the biopsy after the first needle biopsy, re-biopsy if the resection margin is positive, avoiding the lumpectomy or segmental mastectomy with the intent to preserve the breast and the present methods of postoperative radiation therapy all leaves cosmetically much deformed breast that no women prefers to have. The single fraction radiation therapy instead of 5 to 6 weeks duration radiation therapy also is most convenient and economically most beneficial to the patient, to the socially concerned community and healthcare planners and providers all alike. Hence the advantages of the concomitant simple stereotactic needle biopsy combined with onsite immediate curative radiation therapy. A patient 361 is shown as lying with her arm stretched and her breast fixed in stereotactic core needle biopsy position 366 below the cut portion of the extended head side of the stereotactic breast core biopsy system's table 362. The stereotactic breast core biopsy system 360 is incorporated with a PET-CT-stereotactic core biopsy system 364. Stereotactic breast core biopsy is taken from the breast fixed in stereotactic breast core needle biopsy position 366. The biopsy specimen is processed immediately. While the specimen is being processed for histology, the stereotactic system's table 363 with the patient 361 is advanced to the PET-CT-stereotactic core biopsy system 364. The treatment planning PET-CT with patient in stereotactic treatment position is taken and a preliminary online treatment planning is done. For those patients strongly suspected to have breast cancer, pre-biopsy $^{18}$F-glucose is administered as the tracer for the PET scan. This PET scan also serves for the future follow up of the patient's disease. If the biopsy specimen confirms the presence of cancer, immediate final treatment planning is completed and the multiple or single set, 10 beams each, parallel microbeam breast implant is performed. In this case, a CNT based 3 sets, 30 parallel microbeams breast implant 368 is shown in the insert which is described in detail in FIG. 17 (23). Alternatively, immediate single session whole breast radiation is rendered. The whole breast radiation may also be rendered with patient stereotactic breast core biopsy position or in supine position with external beams from CNT-based X-ray sources or from microfocus X-ray tubes with or without megavoltage beam from an accelerator.

Figure 19:
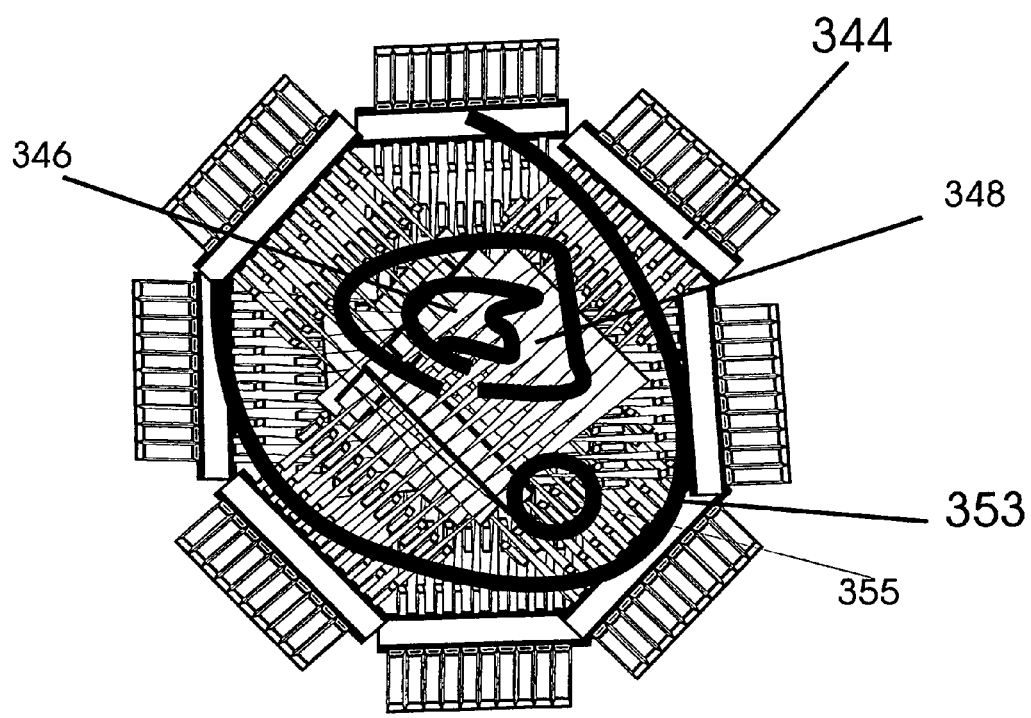
FIG. 19 illustrates a whole breast interstitial radiation therapy with CNT based X-ray tube's microbeams, eight sets, 10 microbeams each and combined total 80 simultaneous microbeams for an early stage breast cancer and the tumor receiving simultaneous boost radiation from the simultaneous beams passing through the isocenter.

FIG. 19 illustrates a whole breast interstitial radiation therapy with CNT based X-ray tube's microbeams, eight sets, 10 parallel microbeams each and combined total 80 simultaneous microbeams for an early stage breast cancer and the tumor receiving simultaneous boost radiation from the simultaneous beams passing through the isocenter. Eight sets of CNT field emission cathodes based 10 beam interstitial implants 344 are shown as partially implanted into the breast 353 from every 45 degree angles. The breast 353 with the gross tumor volumes (GTV), 346 and the planning tumor volume (PTV) 348 are well covered by these 80 simultaneous microbeams. It facilitates concomitant single session whole breast radiation and radiation therapy to the tumor with higher dose.

Figure 20:
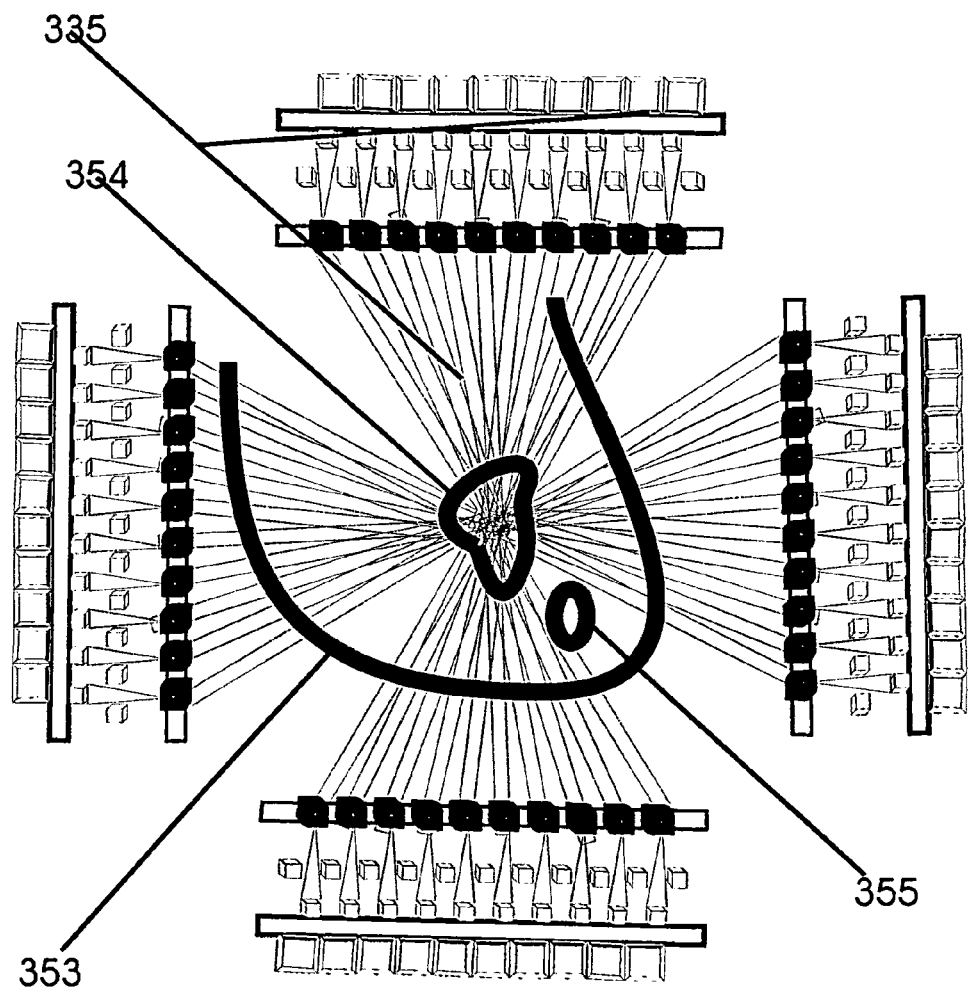
FIG. 20 illustrates a forty focused simultaneous external beam radiation to an early stage breast cancer with four sets of CNT based X-ray tubs and each set's 10 beams as focused to the isocentric tumor.
Figure 22:
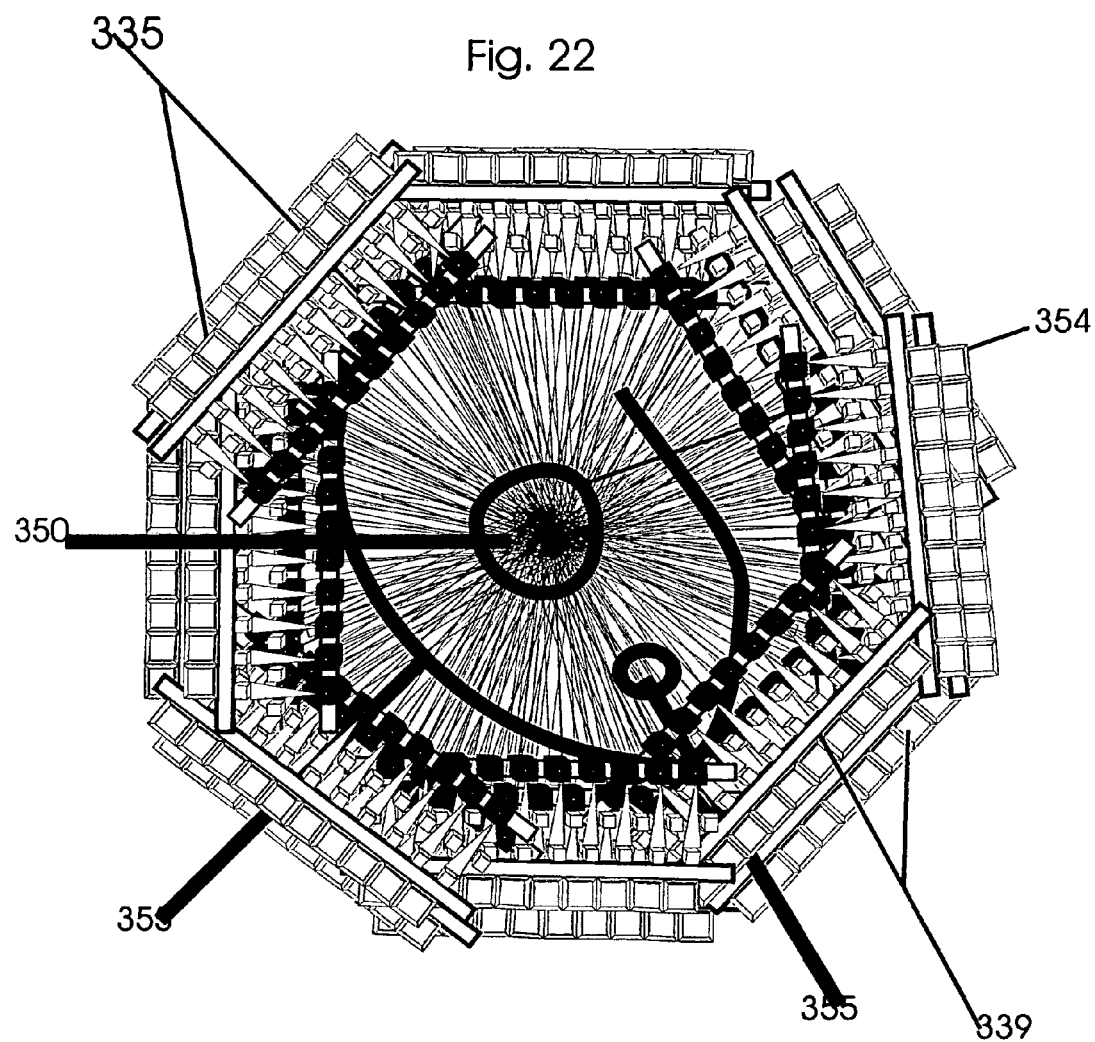
FIG. 22 is similar to that illustrated in FIG. 21 but with 160 external CNT based X-ray microbeams with loss of microbeam-valley sparing of normal tissue

FIG. 20, FIG. 21 and FIG. 22 are another illustration of external microbeam radiation therapy to the breast as an example for the whole organ preserving, minimally toxic and curative radiation therapy. FIG. 20 illustrates a forty focused simultaneous external beam radiation to an early stage breast cancer with four sets of CNT based X-ray tube with converging focused 10 beams 335 and each set's 10 beams as focused to the isocentric tumor 354. Four sets of external CNT based X-ray tubes with converging focused 10 beams 335 are shown as converging into the isocentric tumor 354 in the breast 353 with nipple 355. The forty simultaneous microbeams, all converging at the isocentric tumor renders high additive dose and dose rates but not at high dose as it is possible with treating a tumor with parallel micro beams. It is because the loss of valley dose effect in sparing of the normal tissue. Still, the additive dose of all the beams is so high that it sterilizes the "differentiated" and the dormant tumor stem cells that could otherwise cause later tumor recurrence. It is a simple, single session external curative radiation to the tumor. It could also be used as concomitant boost or as boost radiation after completing the initial whole breast radiation. FIG. 21 illustrates the method of whole breast radiation with concomitant high dose to the tumor with eighty focused simultaneous external microbeam from CNT based X-ray tubs and each set's 10 beams as focused to the isocenter and with higher dose to the isocentric tumor from all the eighty beams converging at the isocenter. This method of microbeam radiation is better tolerated due to the capacity for the normal tissue regeneration and sterilization of the tumor tissue at the isocenter. Eight sets of external CNT based X-ray tubes, each having converging focused 10 beams 335 are shown as converging into the isocentric tumor 354 in the breast 353 with nipple 355 and also diffusely radiating the whole breast. The eighty simultaneous microbeams, all converging at the isocentric tumor renders high additive dose and dose rates that sterilizes the "differentiated" and the dormant tumor stem cells that could otherwise cause later tumor recurrence. It is a simple, single session external CNT based X-ray whole breast radiation and curative dose radiation to the isocentric tumor. FIG. 22 is similar to that illustrated in FIG. 21 but with 160 external CNT based X-ray microbeams.

Figure 23:
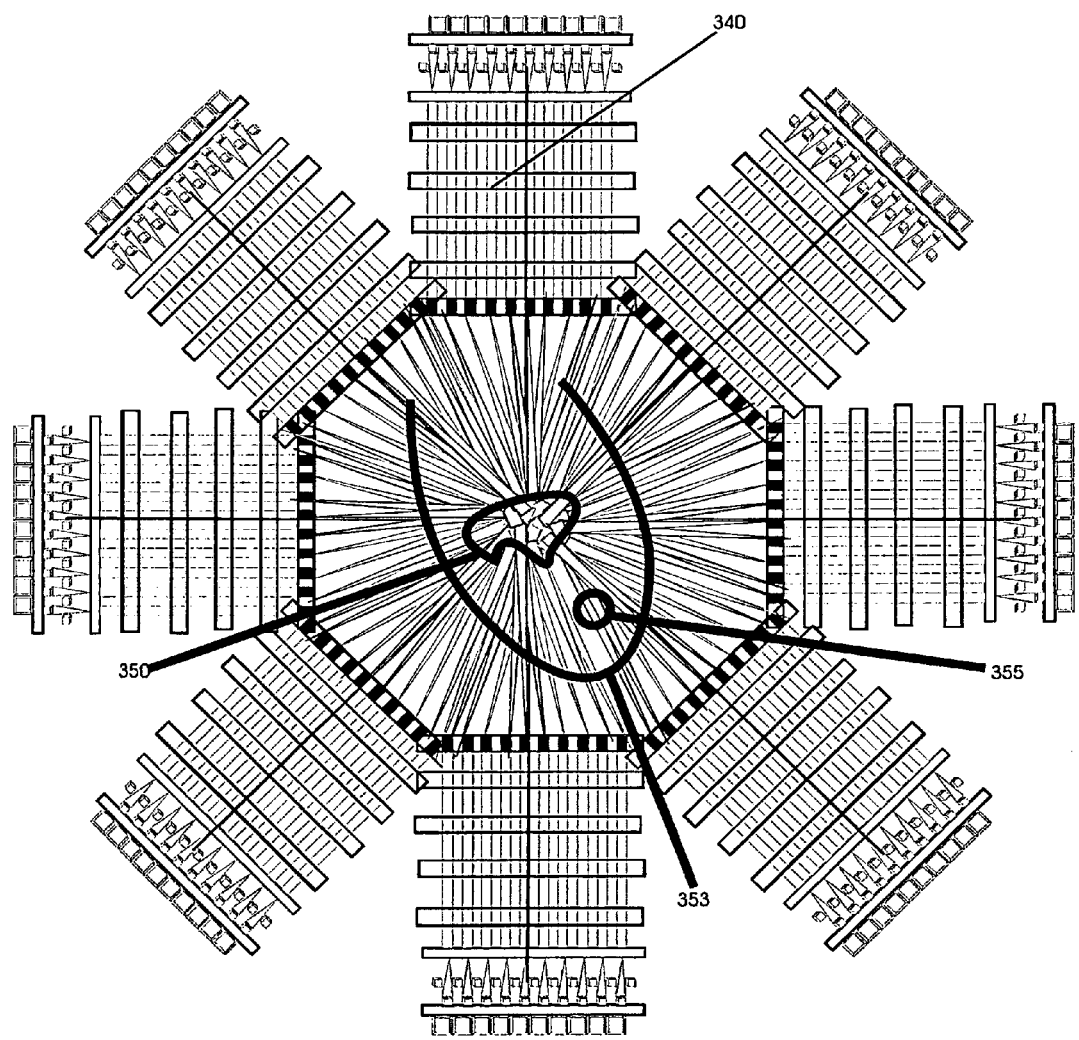
FIG. 23 shows eight sets of CNT based X-ray micro-accelerators, each with 10 minimally diverging microbeams and each accelerator arranged in a circle at 45 degrees apart to radiate a breast cancer with whole breast preservation

FIG. 23 shows eight sets of CNT based X-ray micro-accelerators, each with 10 minimally diverging microbeams and each accelerator arranged in a circle at 45 degrees apart to radiate a breast cancer. Such configured eight micro CNT-based X-ray micro accelerators are described under FIG. 11. In this FIG. 23, their microbeams are directed towards the isocenter where a breast tumor is located. It is shown here as an example of whole organ preserving radiation therapy with multiple simultaneous microbeams, in this instance with combined 80 microbeams. The CNT based micro accelerator is described under FIG. 4. The eight CNT based 10 beams micro-accelerator's 340 eighty microbeams encircles the whole breast 353 and is focused at the isocenter where the early stage breast cancer with microcalcification 350 is located. Because of the microbeams, high additive dose to the tumor that is at the isocenter is delivered, it sterilizes both the "differentiated" and the "tumor stem cell". It prevents the future tumor recurrence. These simultaneous microbeams's additive dose rate can reach close to that of high flux synchrotron that is very effective for tumor sterilization even for those tumors known to be very much resistant to radiation like the glioblastoma multiforme. These beams could be switched on or off individually. It facilitates treating the tumor with desired intensity modulation that conforms to the 3-D shape and configuration of the tumor.

Figure 24:
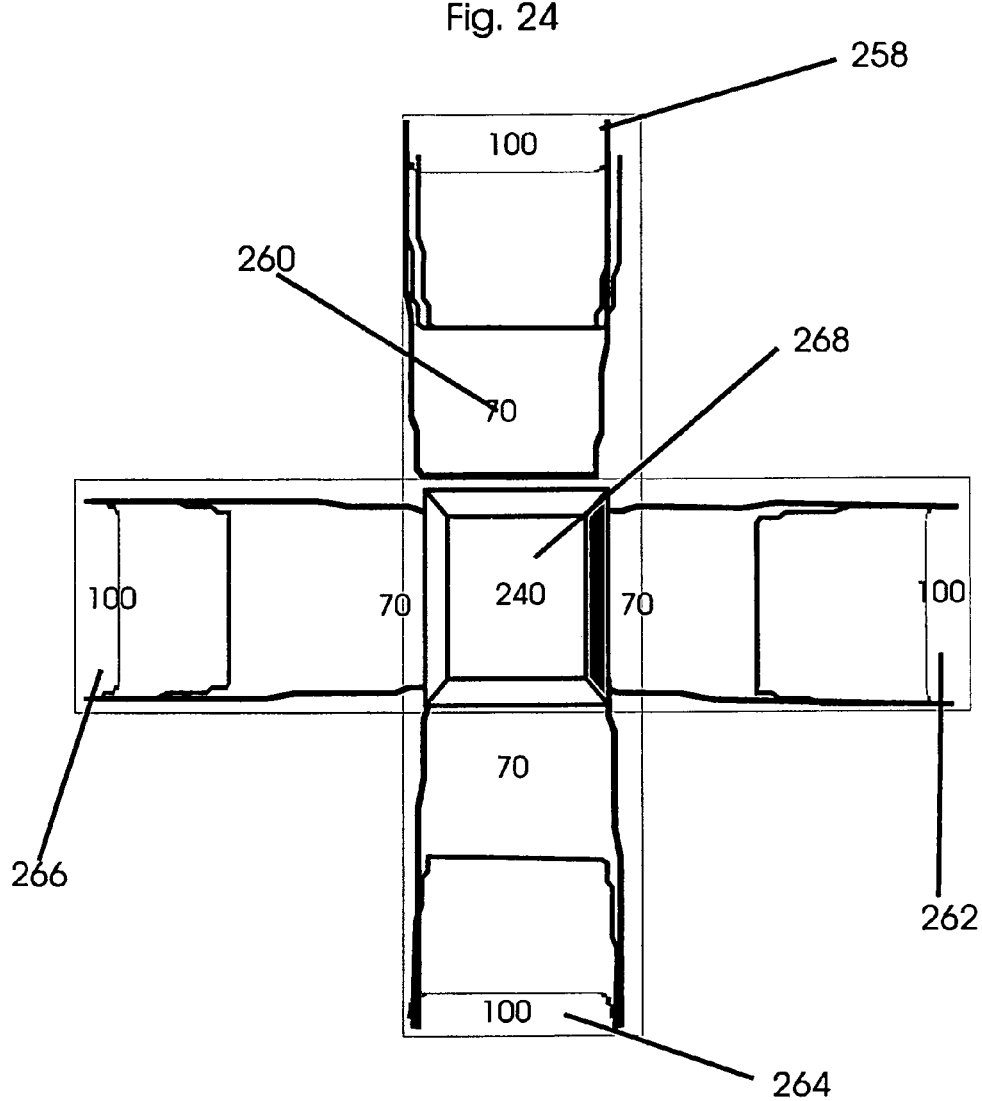
FIG. 24 is a schematic illustration of intensity modulated photon radiation therapy with improved radiobiologic effectiveness with four equally weighed simultaneous beams, each having 100 units at $D_{max}$ and illustrating its high additive biological dose rate where all four beams converge

FIG. 24 is a schematic illustration of intensity modulated photon radiation therapy with improved radiobiologic effectiveness with four equally weighed simultaneous beams, each having 100 units at $D_{max}$ and illustrating its high additive biological dose rate where all four beams converge. Since they are simultaneous beams, this representation of the additive dose from each beam where they converge is a true representation of the isodose as it relates to its biological effectiveness than when such combined isodose is constructed for interrupted beams when each field is treated as one by one at a time. This illustration is an adaptation of the illustration of FIG. 11. 15 C, page 215 from reference (59), The isodose in reference 59, represents an interrupted four field's isodose. If it were a four field simultaneous beam's isodose as it is in this invention, then the four beam's additive dose rate 268 where the beams converge has a peak. This peak rapidly falls off, especially if the beam's energy is low. In this schematic illustration, 100 units are delivered to the $D_{max}$ Single beam's 70% depth dose rate 260 is shown as decreasing to about 70 percent when all the beams converge at the isocenter. Since they are simultaneous beams, these four beams additive dose rate 268 where all the beams converge is biologically more active. It is an "Induced Brag Peak". Because of the additive dose contribution from all the four simultaneous beams, the dose peaks at the point of convergence of all four beams. In this instance, this dose peak is about 240 units Thus by simultaneously delivering 100 units of dose at the $D_{max}$, by four beams, by simultaneous beams 1 from 0-degree 258, simultaneous beam 2 from 90-degree 262, simultaneous beams 3 from 180-degree 264 and simultaneous beams 4 from 270-degree 266 and since they all converge simultaneously at a common pint, their additive dose rate 268 is 240 units. It is 240% higher than that of each single beam's 100 unit $D_{max}$ dose. It is biologically more effective than the conventional delivery of 100 units to each fields as interrupted exposure as one by one field's exposure at a time. With combined monochromatic x-ray from micro focus x-ray tubes and megavoltage photon and electron beam with its combined medical accelerator, additional boost treatment with megavoltage photon and electron with the medical accelerator is elected as needed.

FIG. 25 is a schematic illustration of the Brag-peak like high additive biological dose rate of simultaneous beams that is further enhanced with Auger transformation characteristic radiation which renders intensity modulated photon radiation therapy with improved radiobiologic effectiveness and its comparison with a single beam's dose rate that gradually falls off after the $D_{max}$ dose rate. As in FIG. 7, four simultaneous beams, beams 1 from 0-degree 258, simultaneous beam 2 from 90-degree 262, simultaneous beams 3 from 180-degree 264, simultaneous beams 4 from 270-degree 266 converge at a common point. Hence, their additive dose rate 268 is the combined dose rate at depth for all the four simultaneous beams which is 240 units. It is 240% higher than that of each single beam's 100 unit $D_{max}$ dose. This sharply rising additive dose rate 268 is shown as the rising dose peak. The dose contribution from the interaction of tuned monochromatic x-ray to the k-shell binding energy of the high Z-element nanoparticles bound to the tumor or implanted into it renders additional tumor specific locally confined radiation. This Auger transformation characteristic radiation 270 renders additional locally confined dose peak. The combined Brag-peak like dose peak 272 from the monochromatic x-ray and from the Auger transformation radiation has relatively well defined dose rise and fall within a well defined region like the isocenter. The initial $D_{max}$ dose of the monochromatic radiation from micro focus x-ray tubes and its gradual fall off, insert A, before the sharply rising additive dose rate 268 due to additive dose from all the contributing simultaneous beams and its rapid decrease after the isocenter, insert B, have similarity to the Brag-peak of heavy ion beams. The insert A and the insert B shows the relative dose, RD at Depth. Insert A shows the percent depth dose of a mono chromatic x-ray with dose peak at $D_{max}$ 274. Both have a small tail close to the end of its range. The dose contribution from Auger transformation characteristic radiation 270 is well defined. Both the sharply rising additive dose rate 268 from the simultaneous monochromatic beams and the Auger transformation characteristic radiation 270 from the interaction of monochromatic x-ray that is turned to the k-shell binding energy of the high Z-element nanoparticles bound to the tumor or implanted into it contributes to the combined Brag-peak like dose peak 272. The dose contribution to the normal tissue of the opposite side from exiting beams of parallel opposing beams of lower energy monochromatic x-ray is very minimal. The Auger characteristic x-rays produced by the monochromatic beam's interaction with ligand or implanted nanoparticles high Z-elements is locally confined and absorbed. These effects render a high dose peak at the isocenter where the tumor is located. It falls off rapidly almost like the dose fall off of the Brag-peak. With combined monochromatic x-ray from micro focus x-ray tubes and megavoltage photon and electron beam with its combined medical accelerator, additional boost treatment with megavoltage photon and electron with the medical accelerator is elected as needed.

In present conventional radiation therapy planning with multiple beams, it is a common practice to illustrate the combined isodose from all treatment fields as additive isodose (59). However, it does not represent the additive isodose of simultaneous beams. Examples of multiple filed setup radiation therapy's isodose distribution are illustrated as combined dose from each beam (59). In this instance, each beam's dose contribution is a sequential event and hence its representation as combined additive isodose distribution is not exactly correct. In present practice of conventional radiation therapy, the beams to treat each separate field are switched on sequentially. After treating one field, there is an interruption of time that is taken to rotate the machine and to setup the second field and then to treat the second field. This process is repeated until radiation to the tumor through all the four fields is completed. The Dmax dose gradually decreases as the distance from Dmax to depth increase. Hence, in sequential treatment, the accurate representation of the isodose is not as additive isodose as it is commonly illustrated (59). When additive isodose of such interrupted treatment is illustrated, a correcting notation for the time interval to deliver each beam in sequence and its biological effect is needed.

FIG. 26 is a schematic illustration of the Brag-peak like high additive biological dose rate of simultaneous beams that renders intensity modulated photon radiation therapy with improved radiobiologic effectiveness and its comparison with charged particle beam's Brag-peak and its spread out Brag-peak. Monochromatic charged particle beam's Brag-peak 276 is illustrated in insert C. Initially, its relative dose RD is lower but at a specified depth it sharply increases to its Brag-peak. In insert D, a schematic spread out Brag Peak of carbon ion beam 278 is shown. It is similar to the spread out Brag Peak carbon ion. (92). Insert B and Insert E is a comparative Brag-peak like dose increase of four simultaneous beams 280 as they converge together at a depth distant from the $D_{max}$ dose. It is described in FIG. 7 and FIG. 8. Like in Insert C with monochromatic charged particle beam's Brag-peak 276, in insert B the comparative Brag-peak like dose increase of four simultaneous monochromatic x-ray beams 280 and its relative dose RD at Depth is illustrated. This additive high dose rate effectiveness is much more significant for arrays of 8, 16 or 32 micro focus x-ray tubes. The Brag-peak like high additive dose rate and its associated intensity modulated radiation to the isocentric tumor increase progressively as the number of micro focus x-ray tubes is increased. Likewise, there is a steady increase in RBE as the additive dose rate and LET radiation from multiple simultaneous beams is increased.

The LET of clinically useful monochromatic proton beam is much lower than that of x-ray or Cobalt-60 beams (92) The LET of Cobalt-60, 250-kV x-rays and 150 MeV protons is 0.2, 2.0, and 0.5 respectively (92). With multiple simultaneous beams the energy deposited per unit length of track, keV/μm is higher than that for a single beam. The multiple simultaneous beams will pack per unit length with more deposited energy. Hence the LET of multiple simultaneous beams is higher. The additive very high dose rate of multiple simultaneous beams along with its increased LET improves its RBE. Hence the RBE of multiple simultaneous monochromatic beams is much higher than that of clinical proton beam. The LET of clinically used spread out Brag-peak carbon ion is reported to be as equivalent to clinical neutron beam's LET of 65 keV/μm. The clinical RBE of such spread out carbon ion beam depends on the dose rate and the filed size. In fractionated treatment, the clinical RBE at the center of 10 cm width carbon ion beam was determined as 2.2 (51). Because of the additive super high dose rate and improved LET of multiple simultaneous monochromatic x-ray beams, its RBE for a 10 cm width filed is much higher than that of the proton beam. It would be close to that of 10 cm width spread out carbon ion beam. Among other advantages of radiation therapy with multiple simultaneous monochromatic beams includes its simplicity and safety in operation than those with heavy ion beams. There is no activation of beam shaping collimators with monochromatic x-ray beam as there is with carbon ion beam (91). The combination of micro focus x-ray tube's low energy monochromatic beam's sharp Brag-peak like dose rate increase at the point where all the simultaneous beams meet together and its relatively sharp fall off and its improved LET makes an array of micro focus x-ray tube system is an alternative very cheep radiation therapy system that renders most of the biological advantages of very costly and maintenance intensive heavy ion producing systems like proton or carbon ion producing machines for radiation therapy of cancer.

Figure 27A:
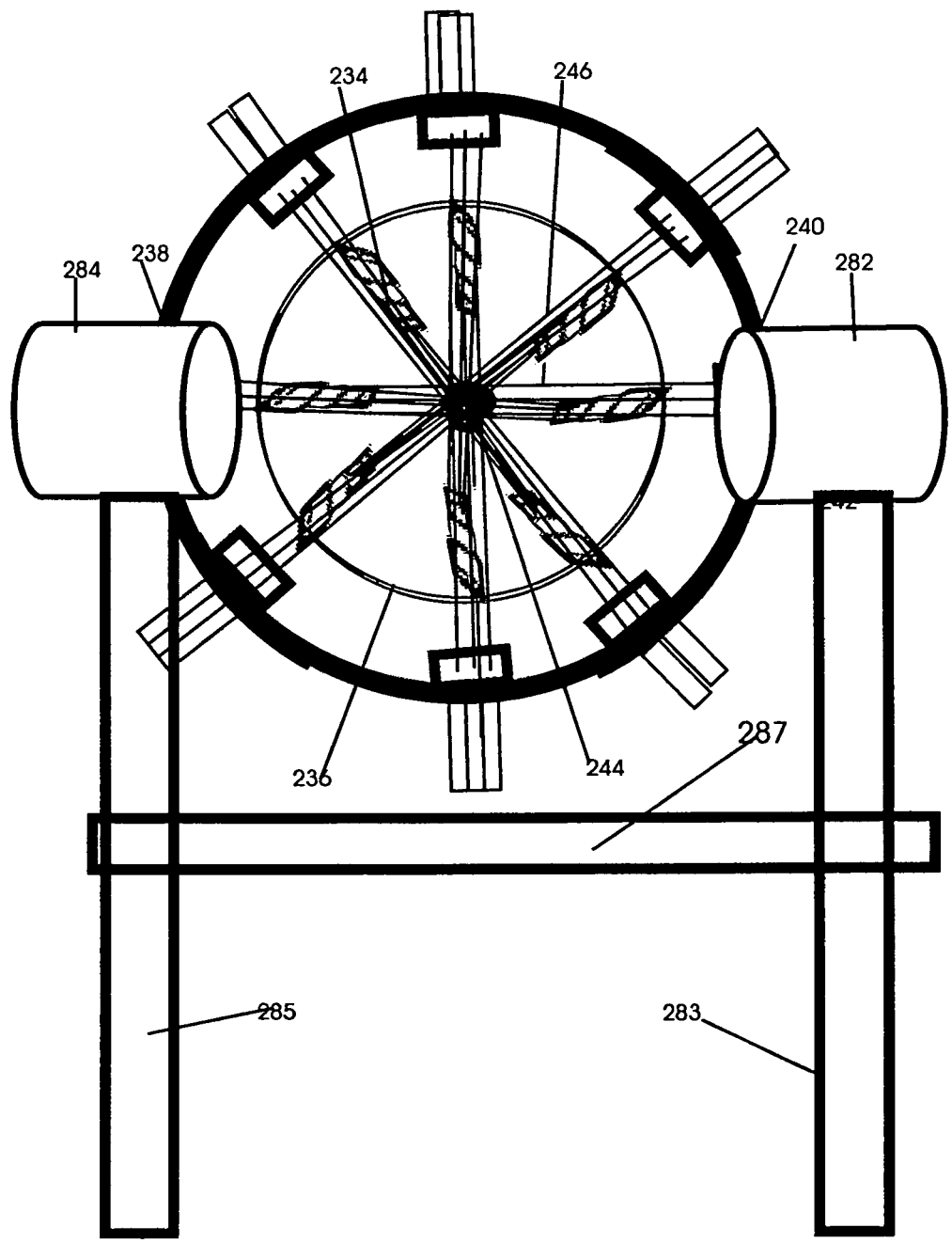
FIG. 27B illustrates an eight micro focus x-ray source system for radiation therapy combined with phase contrast or absorption radiology imaging and a split magnet MRI system.

FIG. 27A and FIG. 27 B illustrates an eight micro focus x-ray system for radiation therapy combined with phase contrast or absorption radiology imaging, and a split magnet MRI system. The exiting divergent beams 246 are shown as exposing the stationary detectors 238 attached to the stationary detector holding ring 240. Any scattered x-ray from the monochromatic x-ray beam 246 from micro focus x-ray sources 234 after its passing through the object and its isocenter 244 are removed by the collimator 236 with pinhole opening for the exiting straight monochromatic x-ray after exposing the object. Portions of the collimator 236 that is not facing the micro focus x-ray source 234 has no pinhole openings for the scattered x-ray to pass through and to reach the detectors. The collimator 236 is made of high atomic number elements like lead or tungsten. In addition collimating beam guides (not shown) also made of high atomic weight elements and coated with x-ray absorbing membrane like silicon is inserted as side cover to the detector to minimize the scatter radiation reaching the stationary detectors 238 from the tilted micro focus x-ray sources. Time sequential sampling of the beams reaching the stationary detector 238 further improves the image quality. The detectors are selected from the group of scintillation based detectors, photon counting detectors or energy discriminating detectors. The scintillation based detector's photodiodes converts the x-ray photon to lower energy charge and to a pixel. It measures the radiation attenuation at each pixel locations. Such data is further processed by the signal processing system 242. With such multiple collimated simultaneous monochromatic beams reaching the detectors after exposing the object and with time sequential sampling of such monochromatic phase contrast x-ray signals improves the image quality several folds than the present image guided radiation therapy with single beam megavoltage or kilovoltage CT, MVCT or kV CT.

In FIG. 27A the two movable segments of a split magnet are shown as moved to above the ground in imaging position for MRI and MRSI. The open magnet segment one 282 and the open magnet segment two 284 are moved from below the ground to above the ground with the aid of motor driven lifting and retrieving piston attached to the magnet segments. The lifting and retracting piston 283 lifts or retracts the open magnet one 282. The lifting and retracting piston 285 lifts or retracts the open magnet one 284. The magnet segments are lifted from below the ground in the treatment room and is brought closer to the patient for MRI of the tumor that is located in the isocenter 244.

Figure 27B:
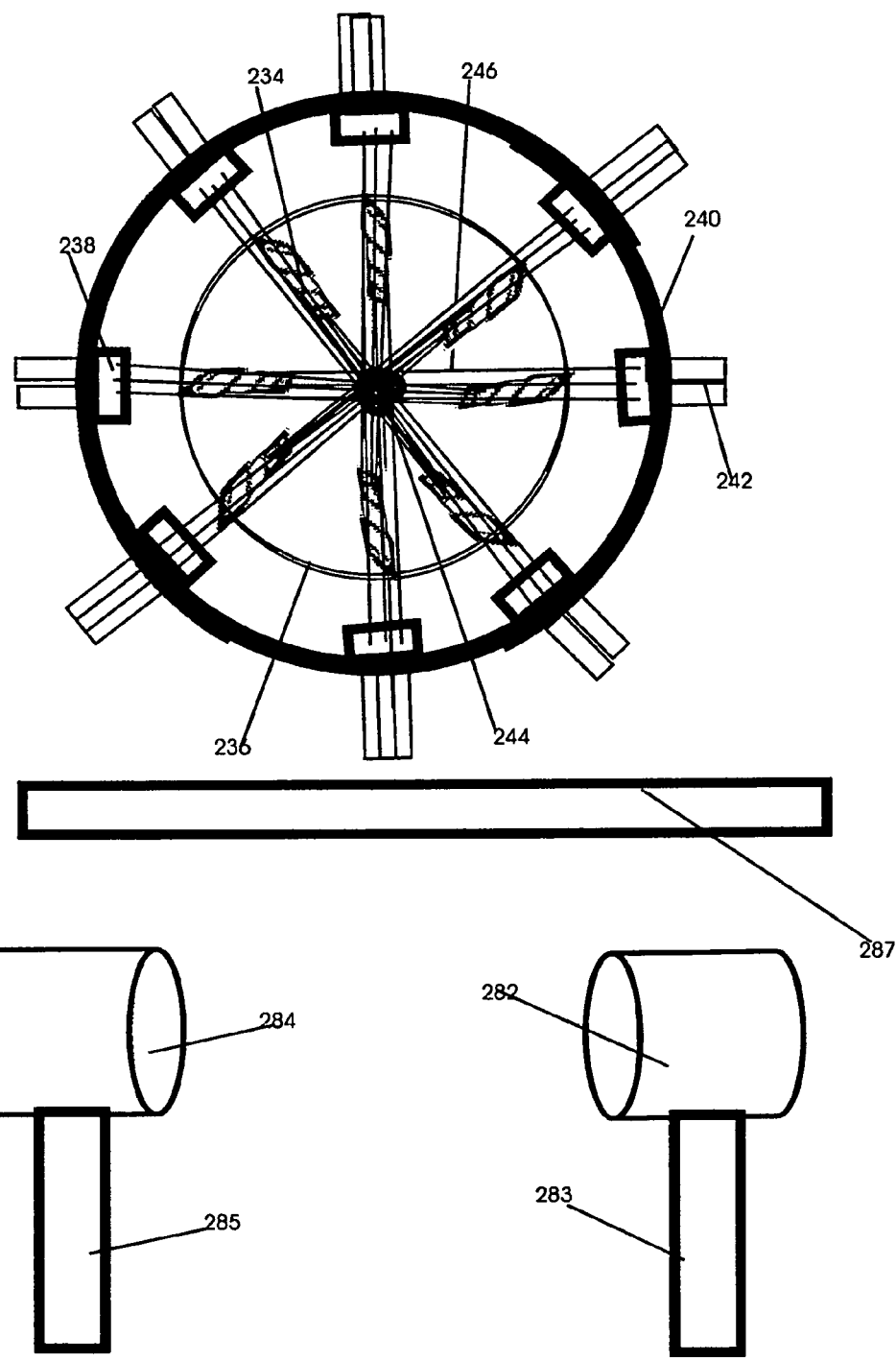

In FIG. 27B, the two movable segments of a split magnet are shown as moved to below the ground after imaging, underneath the floor 287 to avoid interference from the magnetic field during kV CT and or the treatment with the kV beam. It also provides more room to work around the patient who is being treated in the treatment room. If the MRI and MRSI are combined with the radiation therapy, then the magnet segments 282 and magnet segment 284 are kept above the ground. It enables online single session phase contrast and MRI image guided simulation, field-shaping block making, treatment planning, radiation therapy and MRSI during radiation therapy and analysis of events taking place in the cell during radiation therapy.

Methods of Operation

Monochromatic parallel or semi-parallel focused x-ray beam from thermionic micro focus x-ray tubes and field emission carbon nanotube (CNT) cathode based X-ray tubes are used for intraoperative radiation therapy. The source to target optic distance indicator devices is well known in the art of radiation therapy. It is incorporated into this system to indicate the distance from the source to the target that is treated. This distance is also determined by manual measurements with the aid of inspection and palpation of the tumor in relation to the X-ray source. Synchrotron generated microbeam has a dose rate of about 20,000 Gy/min. Such synchrotron microbeams are very effective to sterilize even the most radioresistant tumors like the glioblastoma. However, synchrotron radiation is not readily available to most cancer treatment centers. Hence alternative methods of super high dose rate microbeam radiation therapy systems are used this invention. Depending on the number of current pulses, the dose rate of CNT based x-ray tubes can vary from cGy to $10^4$ Gy/sec. The additive super high dose rate that can be reached with 32 microfocus X-ray tube is about 20 Gy/min. These alternate high dose rate microbeam systems do not have the same high dose rate of synchrotron microbeams; still they are satisfactory alternatives for advanced microbeam radiation therapy. They are capable of tumor cell sterilization and organ preservation with minimal toxicity to normal tissue. Regeneration of normal tissue from the valley of the microbeam replaces the tumor tissue occupied at the peak track of the microbeams. Such high dose rate microbeams are used as alternatives to synchrotron microbeam radiation. It is capable of sterilizing both the "differentiated" tumor cell and dormant tumor stem cells including the most radioresistant tumor cells like the glioblastoma multiforme. It is also used to treat an organ with the intent to maintain its functionality and to preserve its cosmetic appearance like the whole breast preserving radiation therapy with minimal surgery and breast deformity.

The tuned energy from these X-ray sources also generates locally confined Auger transformation characteristic x-ray by its interaction with high z-element bound to the tumor or implanted into it. Such low energy X-ray in the range of 10 to 20 kV is locally absorbed with superior radiobiological effectiveness. The treatment is administered at short distance from the source, as intraoperative, single fraction contact radiation therapy.

Phase Contrast Imaging and MRI Guided Radiation Therapy

The GTV, CTV, PTV that also includes important soft tissue structures are imaged with phase contrast imaging combined with CT, MRI and MRSI. Phase contrast imaging is done by the method of phase shift of the monochromatic parallel X-ray photons. Minimal deviation from the initial path of the incident x-ray beam occurs as it interacts with the atom of the object that it radiates as it passes through the soft tissue. This phase shift is also known as small angle scattering the incident beam within the object that it radiates. The deflected x-ray is registered as pixels in the detector. More image details, especially the microscopic details is imaged by phase contrast imaging with low energy, longer wave length beams. Thus the 10 to 50 kV beams that are also used for intraoperative radiation therapy in this invention are capable of soft tissue imaging with its microscopic details. It is incorporated into radiation therapy planning and clinical investigations of events taking place in radiated tissue before, during and after radiation therapy alone or when it is combined with hyperthermia.

The monochromatic x-ray beam from micro focus x-ray sources is used for radiation therapy combined with phase contrast or absorption imaging. Imaging with multiple simultaneous monochromatic x-rays is performed. In simultaneous x-ray beam imaging mode, all the segments of the mostly monochromatic x-ray beams are deflected towards the imaging target in a patient. Any scattered radiation is absorbed by the arced collimator 236. The 5-50 micro spot monochromatic x-ray beam with nearly no scatter improves the image quality 100 to 1000 times more than that for bremsstrahlung x-rays. It enhances the details in an image. Molecular imaging is done with the hybrid molecular imaging device like PET scan, SPECT scan, contrast enhanced ultrasound and or with similar hybrid molecular imaging devices incorporated with micro focus multiple simultaneous beam x-ray sources. Methods of Simultaneous Several Ports Microbeam Radiation Therapy Combined with Clinical Research The radiation therapy is usually combined with single fraction radiosurgery. For single fraction simultaneous several ports microbeam radiosurgery combined with phase contrast imaging and molecular imaging MRI, the patient is set up with minimum required immobilization needs. For MRI, the split magnet is lifted from below the ground where the treatment table is located with the aid of the magnet lifting pistons and brought close to the table where the patient is resting. After the MRI imaging, the magnet is retracted back to below the ground. Since the radiation lasts only a few seconds or a fraction of a second, the organ movements associated with breathing or peristalsis etc is much reduced. The extensive treatment set ups with complex immobilization is not needed. The microbeam miniaturized microfocus thermionic X-ray tubes or field emission CNT-based X-ray tubes are attached to the surgical table or they are implanted into the tumor. Alternatively, the gantry mounted microfocus X-ray tubes are used. If the radiation therapy is combined with surgery and hyperthermia, the patient is anesthetized. On line visualization of treatment region by combined phase contrast or absorption radiology facilitates improving the target directed external radiation therapy. The ligand-receptor or antibody bound or implanted higher atomic weight elements and tuned monochromatic x-ray to the binding energies of the k, l, m, n shell facilitates characteristic photon and Auger electron for based imaging and radiation therapy. For Auger transformation-radioimmunotherapy and gene targeted therapy the metallic nano particle bound monoclonal antibodies is administered before radiation. Radiation therapy and sufficient time is allowed to reach the maximum concentration of such ligands in the tumor as determined by phase contrast and molecular imaging MRI. With high dose rate in the range of 20,000 Gy/sec and multiple simultaneous monochromatic microbeams and scattered and Auger transformation 10-20 kV X-rays filling the valley in between the microbeams within the tumor and with its high $\alpha/\beta$ ratio and its sublethal damage repair inhibition, the effectiveness of radioimmunotherapy and gene targeted therapy is much improved. The beam energy is tuned to the tumor bound high Z-elements. The peak and valley dose differential of the monochromatic beam and taking its advantage to spare the normal tissue while radiation a tumor at dose in the range of 200-5,000 Gy is described at various points in this invention. The non-cross firing microbeam radiation by orthogonal X-ray tube configuration and or placement of the miniaturized X-ray tubes at least at 45 degree angle apart improves the peak and valley-normal tissue sparing principle microbeam radiation therapy with least toxicity to normal tissue. It induces tumor cell's single and double stand DNA breaks leading to tumor specific radiation and tumor specific cell kill. The pencil beam characteristics of monochromatic x-ray and the surgically exposed tumor and the radiating sourced brought very close to the tumor facilitates high dose rate and also sufficient penetration of the kV X-rays into the tumor. The radiation field shaping methods includes those with multileaf collimators or with tungsten powder or Cerrobend blocks as was described by this inventor in previous patent application Ser. No. 11/974,876 (3) and in Ser. No. 11/998,063 (5). When it is a single fraction radiation therapy, custom field shaping during the treatment process is made. The field shaping with tungsten powder or Cerrobend further decreases the capital cost for the equipments than when it is done with multileaf collimators.

A treatment-planning computer is loaded with the 3-D phase contrast image or the 2D absorption radiology images. It does the segmentations of such images for the treatment planning. Its 3-D VR format is used for treatment planning and dose calculations. Live interactive surface and internal anatomy of the treatment site is projected as 3D-VR-image format with superimposed isodose curves onto the stereoscopic monitor and as 3-D beam's eye view onto the 2-D monitor. Live interactive necessary adjustments are made to the beam's energy, dose rate and weights with the patient in treatment position and ready to be treated. The computer generated treatment plan defines field size and the beam weight for each of the beam.

The radiation therapy and clinical research is combined with XRD and single wavelength anomalous diffraction SAD phasing for soft tissue protein analysis. It facilitates clinical research that was not possible before. With dual source micro focus x-ray tubes like those with copper and chromium de novo laboratory and clinical protein analysis are made. Varying energy simultaneous X-ray beams from multiple micro focus x-ray tubes equipped with monochromating optics and microbeam collimators are used for low molecular weight soft tissue analysis. It also facilitates further expansion of studies on normal and diseased soft tissue components. SAD phasing for protein analysis, XRD of crystalline biomaterials, its use for tissue-receptor bound drug delivery and drug discovery, XRD methods to follow up of a disease and its treatment all are utilized as a tool for clinical research.

For intraoperative radiosurgery, multiple miniaturized X-ray units of the size of a dime are brought close to surgically exposed tumor. They also includes CNT based miniaturized accelerators. They are fixed on to a flexible but firm X-ray unit holder that is shaped in conformity with the tumor. Transverse, coronal and or sagital gantries hold the miniaturized X-ray tubes. The radiating field is configured according to the 3D shape of the surgically exposed tumor. If this configuration's online treatment planning indicates the need for boost dose to a region, then CNT based interstitial implant X-ray units are also implanted into the region to boost the low dose regions as per treatment planning isodose distributions. Online treatment plan is generated per surgical findings and per on line 3-D CT, MRI or phase contrast imaging that are described in the past patent applications by this inventor (5, 7. 8, 9, and 11). If surgical exposure is not needed as in the case of organ preserving whole breast preservation, similar external or interstitial implant treatment procedures are followed.
Whole Breast Preservation Radiosurgery for Breast Cancer For whole breast preservation radiosurgery for breast cancer, the same method of external or interstitial CNT based X-ray tube implant is combined with stereotactic radiosurgery. As an alternative, multiple simultaneous beam electronic brachytherapy systems as described under FIGS. 15 to 23, whole breast preserving radiation therapy. Preoperatively, the patients are prepared for combined CT/PET imaging. After the patient is positioned on to the stereotactic core needle biopsy table, the CT/PET imaging is taken by advancing the stereotactic core needle biopsy table with the patient so fixed to the CT/PET imaging unit. After the CT/PET imaging is taken, the stereotactic core needle biopsy table with the patient is brought back in stereotactic core needle biopsy position and stereotactic core needle biopsies are taken. Immediate, onsite histological examination of the biopsy tissue so obtained is performed. While waiting for the histological results, a tentative treatment planning with the patient in the same stereotactic core biopsy position as in the treatment position is taken. If the diagnosis of cancer is made, then the whole breast preserving Grenz ray contact radiation with CNT based X-ray tubes or accelerators or interstitial implant is done as described above. The whole breast receives radiation from the cross firing peak and valley of the microbeams. The regeneration capabilities of the normal tissue in the valley of the microbeams, the cosmoses of the breast is preserved while the tumor is sterilized by the broad beam effect where all the cross firing simultaneous beams meets. In the case of parallel microbeams, it forms a square intense radiation filed at the isocentric tumor site. It results in a broad beam effect. With dose rate close to that of synchrotron microbeams, both the "differentiated" and the dormant stem cells are sterilized both in the tumor bed and in the breast. Hence no additional treatment may be needed. Patients are kept under tamoxifen for a period to assure additional precaution from tumor recurrence. If the periodic PET/CT imaging and mammograms, at about 6 months intervals, initially and later at yearly mammograms and at two year interval PET/CT imaging shows suspicious regions for tumor recurrence, then surgical biopsy is taken from that region and if there is tumor recurrence, then surgical excision and re-radiation or mastectomy is elected as per the patient's desire and clinical findings.

The ligand-receptor or antibody bound or directly implanted higher atomic weight elements and tuned monochromatic x-ray to the binding energies of the k, l, m, n shell facilitates locally confined Auger transformation characteristic x-ray radiation therapy. Higher atomic weight iodine tagged ligands or implanted gold or titanium or similar high z-element nanoparticles into the tumor are radiated with monochromatic x-ray that is tuned to the k-shell binding energies. For Auger transformation-radioimmunotherapy and gene targeted therapy the metallic nano particle bound monoclonal antibodies that are made as metalloprotein is administered before radiation. Radiation therapy is rendered after the maximum concentration of such ligands has reached in the tumor as determined by phase contrast and molecular imaging described in above referenced pending patent applications, (5, 7, 8, 9 and 11). The 20,000 Gy/sec dose rate microbeam radiation and the additive LET of multiple simultaneous beam has a steeper cell survival curve with high $\alpha/\beta$ ratio and sublethal damage repair inhibition and hence much improved RBE. It is further improved with 10-20 kV scattered and Auger radiation. Hence the effectiveness of tumor specific radioimmunotherapy and gene targeted therapy is also much improved. It induces increased tumor cell's single and double strand DNA breaks leading to tumor specific radiation and tumor specific cell kill. Toleration mouse skin for microbeam radiation is in the range of 500 to 5,000 Gy. The surgical exposure, decreased SSD from the microfocus X-ray tubes and the pencil beam characteristics of monochromatic microbeam X-ray provide sufficient penetration of the radiation in breast tissue to allow treating a deeper seated tumor. A breast tumor can be easily treated with orthogonal microfocus X-ray tubes than with the conventional tangential megavoltage radiation therapy. Orthogonal microbeam spears the normal tissue since its valley dose is so low and it allows regeneration of the radiated tissue. Hence the whole breast preserving radiation with microbeam causes minimal skin damage or sclerosis. It maintains the breast cosmoses intact. If extended field radiation is needed to treat distant lymph node metastasis and it cannot be administered with kV radiation, additional radiation with megavoltage accelerator combined with microfocus x-ray system as described in the U.S. patent application Ser. No. 12/799,949 (11) by this applicant is an added option.

A treatment-planning computer is loaded with the 3-D CT/MRI or phase contrast image or the 2D absorption radiology images. It does the segmentations of such images for the treatment planning computations. Its 3-D virtual reality (VR) image rendering is used for treatment planning and dose calculations. Live interactive surface and internal anatomy of the treatment site is projected as 3D-VR-image format with superimposed isodose curves onto stereoscopic monitors and as 3-D beam's eye view onto the 2-D monitor. Live interactive adjustments are made to the beam's energy, dose rate and weights with the patient in treatment position and ready to be treated. The computer generated treatment plan defines field size and the beam weight for each of the beam.

The present preferred embodiments of this invention are described here; however other modifications could be made without departing from the scope of this invention. The apparatus, methods, procedures and treatments are exemplary and are not intended as limitations on the scope of the invention. Other variations will appear to those skilled in the art and are contemplated to be within the scope of the appended claims.

| | | | Table of Contents |
|---|---|---|---|
| # | Page # | Line # | Title |
| | | 1 | Image Guided Intraoperative Simultaneous Several Ports Microbeam Radiation Therapy with Microfocus X-Ray Tubes |
| 1 | | 1 | Background |
| 2 | | 2 | Simultaneous Several Ports Microbeam Radiation Therapy with Monochromatic X-Ray Beams |
| 3 | | 8 | Electronic Brachytherapy X-ray Tubes (ERT-Tubes) and Simultaneous Multi-Bam Brachytherapy |
| 4 | | 10 | Carbon Nanotube Field Emission X-ray Tubes (CNT-FE-X-ray Tubes) and Its Additive Dose Rate close to that of Synchrotron Radiation |
| 5 | | 12 | Miniaturized Accelerators Based on Carbon Nanotube Field Emission (CNT-FE Accelerator) with additive Dose Rate close to that of Synchrotron Dose Rate |
| 6 | | 13 | Radiation Therapy with CNT-FE Accelerators with additive Dose Rate close to that of Synchrotron |
| 7 | | 15 | High dose rate synchrotron microbeam radiation therapy |
| 8 | | 16 | Microbeam Contact Radiation Therapy With Microfocus X-ray Tubes and Its Additive High Dose Rate Mimicking to that of Synchrotron Radiation |
| 9 | | 17 | Boost radiation to Residual Malignant Stem Cells with Additive High Dose Rate that Mimics Synchrotron Radiation |
| 10 | | 17 | Valley Dose Fill-in and Induced "Brag Peak" |
| 11 | | 18 | Advantages of Intraoperative Radiation Therapy with Additive High Dose Rate Radiation |
| 12 | | 19 | Intraoperative Radiation Therapy with Multiple Simultaneous Miniature X-ray Tubes |
| 13 | | 20 | Oxygen Enhancement Ratio of Single Session Radiation Therapy with Oxygen Diffusion to Tumor |
| 14 | | 21 | Minimally Invasive Breast Cancer Treatment with Multiple Simultaneous Beams from Electronic Brachytherapy X-ray Tubes |
| 15 | | 24 | Cosmetic Whole Breast Preserving Stereotactic Core Biopsy Combined with Simultaneous Electronic Brachytherapy and a Course of Tamoxifen Before Invasive Surgical Biopsies |
| 16 | | 29 | Cosmetic Whole Breast Preserving Single Fraction Radiation Therapy Without Breast Deforming Surgeries Combined with Tamoxifen for Early Stage Breast Cancer |
| 17 | | 30 | The 10-20 KeV Scatter Radiation and its RBE |
| 18 | | 34 | Lethal and Sublethal Damage Repair Inhibition with Additive, close to 200 Gy/sc Dose Rate that Mimics Synchrotron Radiation |

-continued

Table of Contents

Figure 4B:
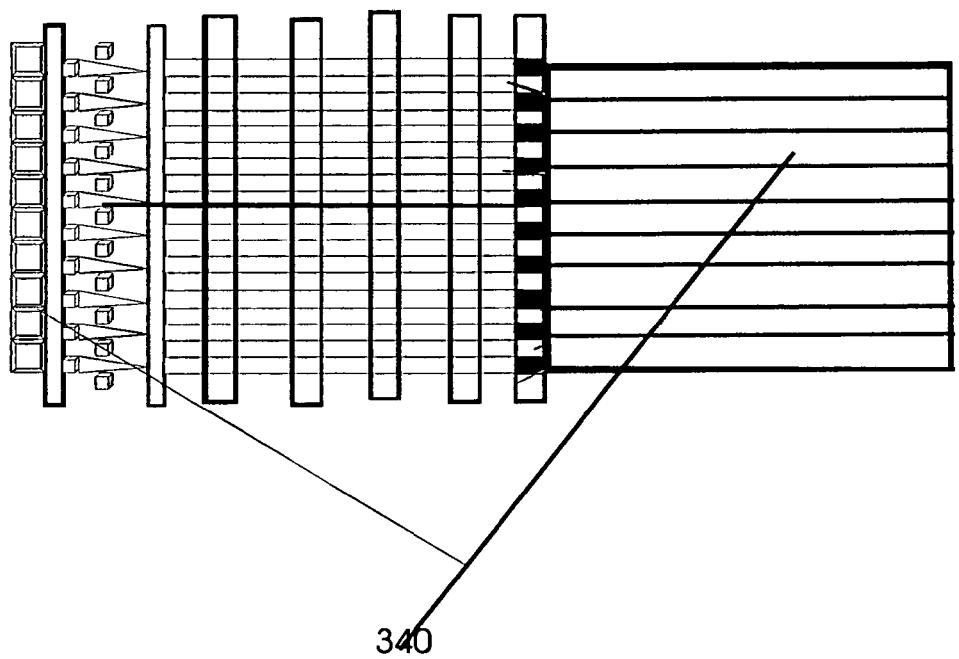

| Page # | Line # | Title |
|---|---|---|
| 19 | 34 | Iodinated Steroids and Iodine k, l, m, n Shell Characteristic Photon and Auger Electron for Imaging and Radiation Therapy |
| 20 | 35 | Contact Intraoperative Radiation Therapy and Its enhanced K-shell Characteristic Photon and Auger Resonant Electron Radiation |
| 21 | 36 | Tumor Specific K-Shell Electron Radiation Therapy and Imaging of Estrogen Receptor Positive and Negative Breast and Testosterone Receptor Positive and Negative Prostate Cancer |
| 22 | 38 | Low-cost advanced Intraoperative Radiation Therapy and Global Oncology |
| 23 | 39 | Cellular Radiation Therapy for benign diseases with Parallel Microbeams from CNT-FE X-Ray Tubes, CNT-FE Accelerators and CNT-FEI X-Ray Tubes |
| 24 | 40 | Cellular Radiation Therapy for Parkinson's disease with Parallel Microbeams from CNT-FE X-Ray Tubes, CNT-FE Accelerators and CNT-FEI X-Ray Tubes |
| 25 | 42 | Phase contrast Imaging and MRI Guided Radiation Therapy |
| 26 | 44 | Brief Summary of the Invention |
| 27 | 46 | Brief description of the drawings |
| 28 | 49 | Reference Numerals |
| 29 | 52 | Description of the Preferred Embodiments |
| 30 | 51 | FIG. 1, Microfocus X-ray tube |
| 31 | 53 | FIG. 2, CNT based single set, 10 simultaneous converging beams X-ray tube |
| 32 | 54 | FIG. 3, Basic structures of a CNT based single set, 10 simultaneous parallel beams CNT based X-ray tube |
| 33 | 54 | FIG. 4 A single set, 10 beam miniaturized electron accelerator based on carbon nanotube field emission (CNT-FE Accelerator) |
| 34 | 55 | FIG. 5, FIG. 6 and FIG. 7A illustrate the left and right halves and a full circle field radiation therapy device. |
| 35 | 57 | FIG. 7B illustrates intraoperative multiple simultaneous beam radiation therapy to a tumor with multiple thermionic miniature X-ray tubes |
| 36 | 57 | Fig 7C illustrates intraoperative radiation to a tumor as shown in FIG. 7B but with CNT based X-ray parallel microbeam |
| 37 | 58 | FIG. &D and 7E shows four sets of CNT based micro-accelerators and their simultaneous 10 parallel microbeams radiating a surgically exposed tumor |
| 38 | 58 | FIG. 8, four sets of CNT based parallel X-ray microbeams X-ray tubes 312 all arranged within a circle and each X-ray tube having 10 parallel microbeams |
| 39 | 59 | FIG. 9 and FIG. 10 miniaturized interstitial implant 10 and 4 beam CNT based X-ray tube with their basic structures |
| 40 | 60 | FIG. 11, eight units, 10 beams each; external CNT based field emission accelerator based combined 80 microbeams radiation therapy system with all the beams converging at the isocenter |
| 41 | 61 | FIG. 12, FIG. 13 and FIG. 13B miniaturized 10 parallel beams accelerator for interstitial implant |
| 42 | 62 | FIG. 14A illustrates selectively switched parallel opposing 6 simultaneous beams from four sets of miniaturized CNT based 10 microbeams micro-accelerators |
| 43 | 62 | FIG. 14B illustrates the parallel microbeams from set of 0 and 90 degree orthogonal miniaturized accelerators |
| 44 | 62 | FIG. 15A, FIG. 15B, FIG. 15D and FIG. and FIG. 16 and FIG. 17, illustrates an early stage breast cancer with microcalcification and treating a tumor with electronic brachytherapy or CNT based X-ray tube's parallel microbeam radiation therapy |
| 45 | 63 | FIG. 15C-1 shows a single micro X-ray tube assembly for implant |
| 46 | 63 | FIG. 15C-2 illustrates an early stage breast cancer as treated with a single simultaneous four microbeam electronic brachytherapy system |
| 47 | 63 | FIG. 15D illustrates an early stage breast cancer treatment with four separate simultaneous microbeam electronic brachytherapy system |
| 48 | 64 | FIG. 16 and FIG. 17, the same breast with early stage breast cancer is shown with CNT based breast implant with 10 parallel microbeams |
| 49 | 65 | FIG. 18, stereotactic breast core biopsy system adapted with PET and CT for CNT based parallel X-ray beam brachytherapy |
| 50 | 67 | FIG. 19, whole breast interstitial radiation therapy with CNT based X-ray tube's microbeams, eight sets |
| 51 | 67 | FIG. 20, 21, 22, external microbeam radiation therapy to the breast as an example for the whole organ preserving, minimally toxic and curative radiation therapy. |
| 52 | 68 | FIG. 23, eight sets of CNT based X-ray micro-accelerators, each with 10 minimally diverging microbeams and each accelerator arranged in a circle at 45 degrees apart, |
| 53 | 69 | FIG. 24, schematic illustration of intensity modulated photon radiation therapy with improved radiobiologic effectiveness with four equally weighed simultaneous beams |
| 54 | 70 | FIG. 25, schematic illustration of the Brag-peak like high additive dose rate of simultaneous beams that is further enhanced with Auger transformation characteristic radiation, |
| 55 | 71 | FIG. 26, schematic illustration of the Brag-peak like high additive biological dose rate of simultaneous beams that renders intensity modulated photon radiation therapy with improved radiobiologic effectiveness, |
| 56 | 73 | FIG. 27A and FIG. 27B illustrates an eight micro focus x-ray system for radiation therapy combined with phase contrast or absorption radiology imaging, and a split magnet MRI system, |
| 57 | 73 | FIG. 27A, two movable segments of a split magnet are shown as moved to above the ground in imaging position for MRI and MRSI |
| 58 | 74 | FIG. 27B, the two movable segments of a split magnet are shown as moved to below the ground after imaging |
| 59 | 74 | Methods of Operation |
| 60 | 75 | Phase contrast Imaging and MRI Guided Radiation Therapy |
| 61 | 70 | Methods of All Field Simultaneous Radiation Therapy combined with clinical research |
| 62 | 76 | Methods of All Field Simultaneous Radiation Therapy combined with clinical research |
| 63 | 78 | Whole breast preservation radiosurgery for breast cancer |
| 63 | 82 | What is claimed is: |
| 64 | 88 | Abstract |

What is claimed is:

1. An apparatus for high additive dose and dose rate conformal radiation therapy comprising:
   a plurality of X-ray producing microfocus X-ray sources configured to simultaneously emit parallel microbeams of radiation that pass through an isocentric tumor in a patient and wherein the intensity of each X-ray source is modulated;
   a plurality of adjustable and dismountable coronal, sagittal, and transverse circular miniature gantries configured to hold the plurality of X-ray sources at different angles; and a plurality of electronic brachytherapy X-ray sources combined with a stereotactic breast core biopsy system.

2. The apparatus of claim 1, wherein the plurality of microfocus X-ray sources are four to ten miniature microfocus X-ray tubes.

3. The apparatus of claim 1, wherein the plurality of microfocus X-ray sources comprises four to eight miniaturized electron accelerator configured to simultaneously emit 10 beams each based on microfocus carbon nanotube field emission for external radiation therapy.

4. The apparatus of claim 1, wherein the plurality of microfocus X-ray sources comprises four to eight miniaturized electron accelerator configured to simultaneously emit 10 beams each based on microfocus carbon nanotube field emission for interstitial implant radiation therapy.

5. The apparatus of claim 1, wherein the plurality of microfocus X-ray sources are four to eight parallel micro-beam generating carbon nanotubes configured to deliver ten microbeams each, and in combination the nanotubes simultaneously deliver forty to eighty microbeams of radiation to the isocentric tumor in one emission period of radiation.

6. The apparatus of claim 4, wherein the stereotactic breast core biopsy system is combined with a positron emission tomography system and the electron accelerators for combined positron emission tomography image guided stereotactic breast core biopsy and interstitial implant radiation therapy.

7. The apparatus of claim 4, wherein the stereotactic breast core biopsy system is combined with a computerized tomography system and the electron accelerators for combined computerized tomography image guided stereotactic breast core biopsy and interstitial implant radiation therapy.

8. The apparatus of claim 1, where the plurality of microfocus X-ray sources are configured to deliver a total prescribed radiation dose to the isocentric tumor in one emission of radiation.

9. The apparatus of claim 1, wherein the plurality of microfocus X-ray sources is one of:
   four to ten X-ray producing microfocus X-ray sources or
   four to eight miniaturized electron accelerators based on microfocus carbon nanotube and configured to simultaneously beams emit 10 beams each, or a combined forty or eighty microbeams of radiation at the isocentric tumor in one emission period for external radiation therapy or interstitial radiation therapy;
   wherein the stereotactic breast core biopsy system is combined with a positron emission tomography system or a computerized tomography system and the microfocus carbon nanotube based electron micro-accelerators for combined positron emission tomography and computerized tomography image guided stereotactic breast core biopsy and interstitial implant radiation therapy.

* * * * *